United States Patent
Bunker et al.

(10) Patent No.: US 6,977,261 B2
(45) Date of Patent: Dec. 20, 2005

(54) AZAISOQUINOLINE DERIVATIVES AS MATRIX METALLOPROTEINASE INHIBITORS

(75) Inventors: Amy Mae Bunker, Ann Arbor, MI (US); Joseph Armand Picard, Canton, MI (US)

(73) Assignee: Warner-Lambert Company LLC, Morris Plains, NJ (US)

( * ) Notice: Subject to any disclaimer, the term of this patent is extended or adjusted under 35 U.S.C. 154(b) by 3 days.

(21) Appl. No.: 10/634,289

(22) Filed: Aug. 5, 2003

(65) Prior Publication Data

US 2004/0038961 A1 Feb. 26, 2004

Related U.S. Application Data

(60) Provisional application No. 60/403,219, filed on Aug. 13, 2002.

(51) Int. Cl.[7] .................. A61K 31/4375; C07D 471/04; A61P 29/00
(52) U.S. Cl. .................. 514/300; 514/210.21; 514/243; 514/247; 514/264.1; 546/122; 544/184; 544/236; 544/279
(58) Field of Search ........................... 546/122; 514/300

(56) References Cited

U.S. PATENT DOCUMENTS

| | | | |
|---|---|---|---|
| 5,367,078 A | * | 11/1994 | Ohno et al. .................. 546/122 |
| 6,008,243 A | | 12/1999 | Bender et al. |
| 6,245,778 B1 | * | 6/2001 | Hadley et al. .............. 514/300 |
| 6,656,932 B2 | | 12/2003 | Picard et al. |
| 2002/0151555 A1 | | 10/2002 | Barvian et al. |
| 2002/0151558 A1 | | 10/2002 | Andrianjara et al. |
| 2002/0156061 A1 | | 10/2002 | Barvian et al. |
| 2002/0156069 A1 | | 10/2002 | Picard et al. |
| 2002/0161000 A1 | | 10/2002 | Barvian et al. |
| 2002/0193377 A1 | | 12/2002 | Andrianjara et al. |
| 2003/0004172 A1 | | 1/2003 | Harter et al. |
| 2003/0078276 A1 | | 4/2003 | Andrianjara et al. |
| 2003/0087924 A1 | | 5/2003 | Sorenson |
| 2003/0130278 A1 | | 7/2003 | Gaudilliere et al. |
| 2003/0144274 A1 | | 7/2003 | Bunker et al. |
| 2003/0216402 A1 | | 11/2003 | Gaudilliere et al. |
| 2003/0220355 A1 | | 11/2003 | Gaudilliere et al. |
| 2004/0006077 A1 | | 1/2004 | Gaudilliere et al. |

FOREIGN PATENT DOCUMENTS

| | | |
|---|---|---|
| EP | 0935963 | 8/1999 |
| EP | 1138680 A1 | 10/2001 |
| WO | WO 00/09485 | 2/2000 |
| WO | WO 01/12611 | 2/2001 |
| WO | WO 01/63244 | 8/2001 |
| WO | WO 02/34726 A3 | 5/2002 |
| WO | WO 02/34753 | 5/2002 |
| WO | WO 02/064080 A3 | 8/2002 |
| WO | WO 02/064080 A2 | 8/2002 |
| WO | WO 02/064547 A2 | 8/2002 |
| WO | WO 02/064547 A3 | 8/2002 |
| WO | WO 02/064568 A1 | 8/2002 |
| WO | WO 02/064571 A1 | 8/2002 |
| WO | WO 02/064572 A1 | 8/2002 |
| WO | WO 02/064578 A1 | 8/2002 |
| WO | WO 02/064595 A1 | 8/2002 |
| WO | WO 02/064598 A1 | 8/2002 |
| WO | WO 02/064599 A1 | 8/2002 |
| WO | WO 03/032999 A1 | 4/2003 |
| WO | WO 03/033478 A1 | 4/2003 |
| WO | WO 03/076417 A3 | 9/2003 |
| WO | WO 03/076417 A2 | 9/2003 |
| WO | WO 04/000322 A1 | 12/2003 |

OTHER PUBLICATIONS

Morphy et al. Current Medicinal Chemistry, 1995, 2(3): 743–762.*

(Continued)

Primary Examiner—Evelyn Mei Huang
(74) Attorney, Agent, or Firm—Charles W. Ashbrook; Claude F. Purchase, Jr.; Pfizer Inc.

(57) ABSTRACT

This invention provides compounds defined by Formula I

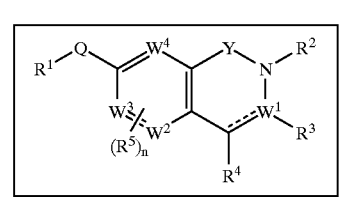

or a pharmaceutically acceptable salt thereof, wherein $R^1$, Q, Y, $R^2$, $R^3$, $R^4$, $R^5$, and n are as defined in the specification. The invention also provides pharmaceutical compositions comprising a compound of Formula I, or a pharmaceutically acceptable salt thereof, as defined in the specification, together with a pharmaceutically acceptable carrier, diluent, or excipient. The invention also provides methods of inhibiting an MMP-13 enzyme in an animal, comprising administering to the animal a compound of Formula I, or a pharmaceutically acceptable salt thereof. The invention also provides methods of treating a disease mediated by an MMP-13 enzyme in a patient, comprising administering to the patient a compound of Formula I, or a pharmaceutically acceptable salt thereof, either alone or in a pharmaceutical composition. The invention also provides methods of treating diseases such as heart disease, multiple sclerosis, osteo- and rheumatoid arthritis, arthritis other than osteo- or rheumatoid arthritis, cardiac insufficiency, inflammatory bowel disease, heart failure, age-related macular degeneration, chronic obstructive pulmonary disease, asthma, periodontal diseases, psoriasis, atherosclerosis, and osteoporosis in a patient, comprising administering to the patient a compound of Formula I, or a pharmaceutically acceptable salt thereof, either alone or in a pharmaceutical composition. The invention also provides combinations, comprising a compound of Formula I, or a pharmaceutically acceptable salt thereof, together with another pharmaceutically active component as described in the specification.

11 Claims, No Drawings

OTHER PUBLICATIONS

From PCT/IB03/03485 International Search Report.

Office Action from 10/264,764, mailed Jun. 16, 2003.

Chen et al., "Structure–Based Design of a Novel, Potent, and Selective Inhibitor for MMP–13 Utiliziing NMR Spectroscopy and Computer–Aided Molecular Design", JACS, 2000; 122: 9648–9654.

Lovejoy, et al., "Crystal structures of MMP–1 and –13 reveal the stuctural basis for selectivity of collagenase inhibitors", Nature Structual Biol., 1999; 6; 217–221.

Moy, et al., "High–resolution Solution Structure of the Catalytic Fragment of Human Collagenase–3 (MMP–13) Complexed with a Hydroxamic Acid Inhibitor", J. Mol. Biol., 2000; 302:671–689.

Mitchell, et al., "Cloning, Expression, and Type II Collagenolytic Activity of Matrix Metalloproteinase–13 from Human Osteoarthritic Cartilage", J. Clin. Invest., 1996; 97(3):761–768.

Neuhold, et al., "Postnatal expression in hyaline cartilage of constituitively active human collagenase–3 (MMP–13) induces osteoarthritis in mice", J. Clin. Invest., 2001; 107(1):35–44.

Dahlberg, et al., "Selective Enhancement of Collagenase–Mediated Cleavage of Resident Type II Collagen in Cultured Osteoarthritic Cartilage Arrest with a Synthetic Inhibitor That Spares Collagenase 1 (Matrix Metalloproteinase 1)" Arthrit. & Rheum., 2000; 43(3):673–682.

Billinghurst, et al., "Comparison of the Degradation of Type II Collagen and Proteoglycan in Nasal and Articular Cartilages Induced by Interleukin–1 and the Selective Inhibition of Type II Collagen Cleavage by Collagenase", Arthrit. & Rheum., 2000; 43(3):664–672.

Billinghurst, et al., "Enhanced Cleavage of Type II Collagen by Collagenase in Osteoarthritic Articular Cartilage", J. Clin. Invest., 1997; 99(7):1534–1545.

Hirota, et al., "Novel Synthesis of Pyrido[3,4–d]Pyrimidines, Pyridol[2,3–d]–Pyrimidines, And Quinazolines Via Palladium–Catalyzed Oxidative Coupling", Heterocycles, 1994: 37(1):563–570.

Wernicke, et al., "Cloning of Collagenase 3 from the Synovial Membrane and Its Expression in Rheumatiod Arthritis and Osteoarthritis", J. Rheum., 1996; 23:590–595

Reboul, et al., "The New Collagenase, Collagenase–3, Is Expressed and Synthesized by Human Chondrocytes but not by Synoviocytes", J. Clin. Invest., 1996; 97:2011–2019.

Freemont, et al., "In situ zymographic localisation of type II collagen degrading activity in osteoarthritic human articular cartilage", Ann. Rheum, Dis., 1999; 58:357–365.

U.S. Appl. No. 10/071,032, filed Feb. 8, 2002, Dyer et al.
U.S. Appl. No. 10/634,531, filed Aug. 5, 2003, Johnson.
U.S. Appl. No. 10/634,709, filed Aug. 5, 2003, Bunker et al.
U.S. Appl. No. 10/634,162, filed Aug. 5, 2003, Wilson.
U.S. Appl. No. 10/634,473, filed Aug. 5, 2003, Bunker et al.
U.S. Appl. No. 10/634,180, filed Aug. 5, 2003, Bunker et al.
U.S. Appl. No. 10/634,712, filed Aug. 5, 2003, Hicks et al.
U.S. Appl. No. 10/634,181, filed Aug. 5, 2003, Li.
U.S. Appl. No. 10/634,489, filed Aug. 5, 2003, Roark.
U.S. Appl. No. 10/634,420, filed Aug. 5, 2003, Roark.
U.S. Appl. No. 10/634,716, filed Aug. 5, 2003, Nahara et al.
U.S. Appl. No. 10/634,288, filed Aug. 5, 2003, O'Brien.
U.S. Appl. No. 10/634,717, filed Aug. 5, 2003, Nahra et al.
U.S. Appl. No. 10/634,177, filed Aug. 5, 2003, Wilson.
U.S. Appl. No. 10/634,290, filed Aug. 5, 2003, Wilson.
U.S. Appl. No. 10/634,182, filed Aug. 5, 2003, Li.
U.S. Appl. No. 10/634,419, filed Aug. 5, 2003, Hicks et al.
U.S. Appl. No. 10/634,713, filed Aug. 5, 2003, Picard.
U.S. Appl. No. 10/634,225, filed Aug. 5, 2003, Picard et al.
U.S. Appl. No. 10/634,718, filed Aug. 5, 2003, Ortwine.
U.S. Appl. No. 10/739,261, filed Dec. 18, 2003, Bunker.

* cited by examiner

AZAISOQUINOLINE DERIVATIVES AS MATRIX METALLOPROTEINASE INHIBITORS

CROSS-REFERENCE TO RELATED APPLICATIONS

This application claims benefit of priority from U.S. Provisional Patent Application No. 60/403,219, filed Aug. 13, 2002.

FIELD OF THE INVENTION

This invention relates to azaisoquinoline derivatives which inhibit matrix metalloproteinase enzymes and thus are useful for treating diseases resulting from MMP-mediated tissue breakdown such as heart disease, cardiac insufficiency, inflammatory bowel disease, multiple sclerosis, osteo- and rheumatoid arthritis, arthritis other than osteo- or rheumatoid arthritis, heart failure, age-related macular degeneration, chronic obstructive pulmonary disease, asthma, periodontal diseases, psoriasis, atherosclerosis, and osteoporosis.

BACKGROUND OF THE INVENTION

Matrix metalloproteinases (sometimes referred to as MMPs) are naturally occurring enzymes found in most mammals. Over-expression and activation of MMPs, or an imbalance between MMPs and inhibitors of MMPs, have been suggested as factors in the pathogenesis of diseases characterized by the breakdown of extracellular matrix or connective tissues.

Stromelysin-1 and gelatinase A are members of the MMP family. Other members include fibroblast collagenase (MMP-1), neutrophil collagenase (MMP-8), gelatinase B (92 kDa gelatinase) (MMP-9), stromelysin-2 (MMP-10), stromelysin-3 (MMP-11), matrilysin (MMP-7), collagenase 3 (MMP-13), TNF-alpha converting enzyme (TACE), and other newly discovered membrane-associated matrix metalloproteinases (Sato H., Takino T., Okada Y., Cao J., Shinagawa A., Yamamoto E., and Seiki M., *Nature*, 1994;370:61–65). These enzymes have been implicated with a number of diseases which result from breakdown of connective tissue, including such diseases as rheumatoid arthritis, osteoarthritis, osteoporosis, periodontitis, multiple sclerosis, gingivitis, corneal epidermal and gastric ulceration, atherosclerosis, neointimal proliferation which leads to restenosis and ischemic heart failure, and tumor metastasis. A method for preventing and treating these and other diseases is now recognized to be by inhibiting matrix metalloproteinase enzymes, thereby curtailing and/or eliminating the breakdown of connective tissues that results in the disease states.

There is a catalytic zinc domain in matrix metalloproteinases that is typically the focal point for inhibitor design. The modification of substrates by introducing zinc-chelating groups has generated potent inhibitors such as peptide hydroxamates and thiol-containing peptides. Peptide hydroxamates and the natural endogenous inhibitors of MMPs (TIMPs) have been used successfully to treat animal models of cancer and inflammation. MMP inhibitors have also been used to prevent and treat congestive heart failure and other cardiovascular diseases, U.S. Pat. No. 5,948,780.

A major limitation on the use of currently known MMP inhibitors is their lack of specificity for any particular enzyme. Recent data has established that specific MMP enzymes are associated with some diseases, with no effect on others. The MMPs are generally categorized based on their substrate specificity, and indeed the collagenase subfamily of MMP-1, MMP-8, and MMP-13 selectively cleave native interstitial collagens, and thus are associated only with diseases linked to such interstitial collagen tissue. This is evidenced by the recent discovery that MMP-13 alone is over expressed in breast carcinoma, while MMP-1 alone is over expressed in papillary carcinoma (see Chen et al., *J. Am. Chem. Soc.*, 2000;122:9648–9654).

Selective inhibitors of MMP-13 include a compound named WAY-170523, which has been reported by Chen et al., supra., 2000, and other compounds are reported in PCT International Patent Application Publication numbers WO 01/63244; WO 00/09485; WO 01/12611; WO 02/34726; and WO 02/34753, and European Patent Application numbers EP 935,963 and EP 1,138,680. Further, U.S. Pat. No. 6,008,243 discloses inhibitors of MMP-13. However, no selective or nonselective inhibitor of MMP-13 has been approved and marketed for the treatment of any disease in any mammal. Accordingly, the need continues to find new low molecular weight compounds that are potent and selective MMP inhibitors, and that have an acceptable therapeutic index of toxicity/potency to make them amenable for use clinically in the prevention and treatment of the associated disease states. An object of this invention is to provide a group of selective MMP-13 inhibitor compounds characterized as being azaisoquinoline derivatives.

SUMMARY OF THE INVENTION

This invention provides an azaisoquinoline derived compound defined by Formula I.

Accordingly, embodiments of the invention include:
1. A compound of Formula I

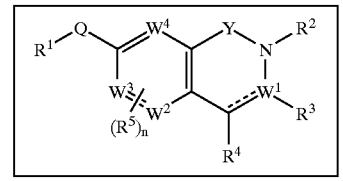

I or a pharmaceutically acceptable salt thereof,
wherein:
$R^1$ is independently selected from:
  $C_5$ or $C_6$ cycloalkyl-($C_1$–$C_8$ alkylenyl);
  Substituted $C_5$ or $C_6$ cycloalkyl-($C_1$–$C_8$ alkylenyl);
  $C_8$–$C_{10}$ bicycloalkyl-($C_1$–$C_8$ alkylenyl);
  Substituted $C_8$–$C_{10}$ bicycloalkyl-($C_1$–$C_8$ alkylenyl);
  5- or 6-membered heterocycloalkyl-($C_1$–$C_8$ alkylenyl);
  Substituted 5- or 6-membered heterocycloalkyl-($C_1$–$C_8$ alkylenyl);
  8- to 10-membered heterobicycloalkyl-($C_1$–$C_8$ alkylenyl);
  Substituted 8- to 10-membered heterobicycloalkyl-($C_1$–$C_8$ alkylenyl);
  Phenyl-($C_1$–$C_8$ alkylenyl);
  Substituted phenyl-($C_1$–$C_8$ alkylenyl);
  Naphthyl-($C_1$–$C_8$ alkylenyl);
  Substituted naphthyl-($C_1$–$C_8$ alkylenyl);
  5- or 6-membered heteroaryl-($C_1$–$C_8$ alkylenyl);
  Substituted 5- or 6-membered heteroaryl-($C_1$–$C_8$ alkylenyl);

8- to 10-membered heterobiaryl-($C_1$–$C_8$ alkylenyl);
Substituted 8- to 10-membered heterobiaryl-($C_1$–$C_8$ alkylenyl);
Phenyl;
Substituted phenyl;
Naphthyl;
Substituted naphthyl;
5- or 6-membered heteroaryl;
Substituted 5- or 6-membered heteroaryl;
8- to 10-membered heterobiaryl; and
Substituted 8- to 10-membered heterobiaryl;
$R^2$ is independently selected from:
  H;
  $C_1$–$C_6$ alkyl;
  Phenyl-($C_1$–$C_8$ alkylenyl);
  Substituted phenyl-($C_1$–$C_8$ alkylenyl);
  Naphthyl-($C_1$–$C_8$ alkylenyl);
  Substituted naphthyl-($C_1$–$C_8$ alkylenyl);
  5- or 6-membered heteroaryl-($C_1$–$C_8$ alkylenyl);
  Substituted 5- or 6-membered heteroaryl-($C_1$–$C_8$ alkylenyl);
  8- to 10-membered heterobiaryl-($C_1$–$C_8$ alkylenyl);
  Substituted 8- to 10-membered heterobiaryl-($C_1$–$C_8$ alkylenyl);
  Phenyl-O—($C_1$–$C_8$ alkylenyl);
  Substituted phenyl-O—($C_1$–$C_8$ alkylenyl);
  Phenyl-S—($C_1$–$C_8$ alkylenyl);
  Substituted phenyl-S—($C_1$–$C_8$ alkylenyl);
  Phenyl-S(O)—($C_1$–$C_8$ alkylenyl);
  Substituted phenyl-S(O)—($C_1$–$C_8$ alkylenyl);
  Phenyl-S(O)$_2$—($C_1$–$C_8$ alkylenyl); and
  Substituted phenyl-S(O)$_2$—($C_1$–$C_8$ alkylenyl);
Each substituted $R^1$ and $R^2$ group contains from 1 to 4 substituents, each independently on a carbon or nitrogen atom, independently selected from:
  $C_1$–$C_6$ alkyl;
  CN;
  $CF_3$;
  HO;
  ($C_1$–$C_6$ alkyl)-O;
  ($C_1$–$C_6$ alkyl)-S(O)$_2$;
  $H_2N$;
  ($C_1$–$C_6$ alkyl)-N(H);
  ($C_1$–$C_6$ alkyl)$_2$-N;
  ($C_1$–$C_6$ alkyl)-C(O)O—($C_1$–$C_8$ alkylenyl)$_m$;
  ($C_1$–$C_6$ alkyl)-C(O)O—(1- to 8-membered heteroalkylenyl)$_m$;
  ($C_1$–$C_6$ alkyl)-C(O)N(H)—($C_1$–$C_8$ alkylenyl)$_m$;
  ($C_1$–$C_6$ alkyl)-C(O)N(H)-(1- to 8-membered heteroalkylenyl)$_m$;
  $H_2NS(O)_2$—($C_1$–$C_8$ alkylenyl);
  ($C_1$–$C_6$ alkyl)-N(H)S(O)$_2$—($C_1$–$C_8$ alkylenyl)$_m$;
  ($C_1$–$C_6$ alkyl)$_2$-NS(O)$_2$—($C_1$–$C_8$ alkylenyl)$_m$;
  3- to 6-membered heterocycloalkyl-(G)$_m$;
  Substituted 3- to 6-membered heterocycloalkyl-(G)$_m$;
  5- or 6-membered heteroaryl-(G)$_m$;
  Substituted 5- or 6-membered heteroaryl-(G)$_m$;
  ($C_1$–$C_6$ alkyl)-S(O)$_2$—N(H)—C(O)—($C_1$–$C_8$ alkylenyl)$_m$; and
  ($C_1$–$C_6$ alkyl)-C(O)—N(H)—S(O)$_2$—($C_1$–$C_8$ alkylenyl)$_m$;
wherein each substituent on a carbon atom may further be independently selected from:
  Halo; and
  $HO_2C$;
wherein 2 substituents may be taken together with a carbon atom to which they are both bonded to form the group C=O;
wherein two adjacent, substantially $sp^2$ carbon atoms may be taken together with a diradical substituent to form a cyclic diradical selected from:

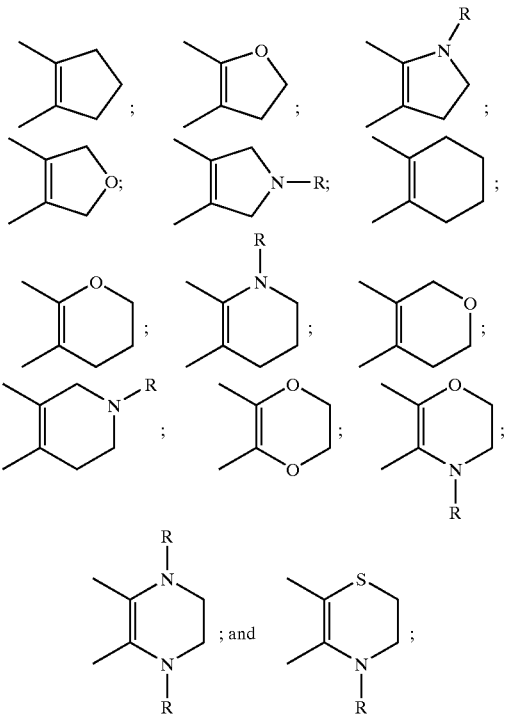

R is H or $C_1$–$C_6$ alkyl;
G is $CH_2$; O, S, S(O); or S(O)$_2$;
Each m is an integer of 0 or 1;
$R^3$ and $R^4$ are independently selected from the groups:
  H;
  $C_1$–$C_6$ alkyl;
  Substituted $C_1$–$C_6$ alkyl;
  $C_2$–$C_6$ alkenyl;
  Substituted $C_2$–$C_6$ alkenyl;
  $C_2$–$C_6$ alkynyl;
  Substituted $C_2$–$C_6$ alkynyl;
  $C_3$–$C_6$ cycloalkyl;
  Substituted $C_3$–$C_6$ cycloalkyl;
  $C_3$–$C_6$ cycloalkyl-($C_1$–$C_8$ alkylenyl);
  Substituted $C_3$–$C_6$ cycloalkyl-($C_1$–$C_8$ alkylenyl);
  Phenyl;
  Substituted phenyl;
  Phenyl-($C_1$–$C_8$ alkylenyl);
  Substituted phenyl-($C_1$–$C_8$ alkylenyl);
  Naphthyl;
  Substituted Naphthyl;
  Naphthyl-($C_1$–$C_8$ alkylenyl);

Substituted naphthyl-($C_1$–$C_8$ alkylenyl);
3- to 6-membered heterocycloalkyl;
Substituted 3- to 6-membered heterocycloalkyl;
3- to 6-membered heterocycloalkyl-($C_1$–$C_8$ alkylenyl);
Substituted 3- to 6-membered heterocycloalkyl-($C_1$–$C_8$ alkylenyl)
HO;
($C_1$–$C_6$ alkyl)-O;
$H_2N$;
($C_1$–$C_6$ alkyl)-N(H);
($C_1$–$C_6$ alkyl)$_2$-N;

Each substituted $R^3$ and $R^4$ group contains from 1 to 4 substituents, each independently on a carbon or nitrogen atom, independently selected from:
  $H_2N$;
  $C_1$–$C_6$ alkyl;
  CN;
  $CF_3$;
  ($C_1$–$C_6$ alkyl)-OC(O);
  HO;
  ($C_1$–$C_6$ alkyl)-O;
  HS; and
  ($C_1$–$C_6$ alkyl)-S;

wherein each substituent on a carbon atom may further be independently selected from:
  Halo; and
  $HO_2C$;

wherein 2 substituents may be taken together with a carbon atom to which they are both bonded to form the group C═O;

$R^5$ is H, $C_1$–$C_6$ alkyl, $H_2N$, HO, or halo;
n is an integer of from 0 to 3;
Q is selected from:
  OC(O);
  CH($R^6$)C(O);
  OC($NR^6$);
  CH($R^6$)C($NR^6$);
  N($R^6$)C(O);
  N($R^6$)C(S);
  N($R^6$)C($NR^6$);
  N($R^6$)$CH_2$;
  SC(O);
  CH($R^6$)C(S);
  SC($NR^6$);
  trans-(H)C═C(H);
  cis-(H)C═C(H);
  C≡C;
  $CH_2$C≡C;
  C≡$CCH_2$;
  $CF_2$C≡C; and
  C≡$CCF_2$;

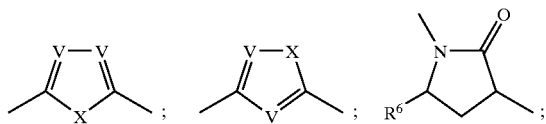

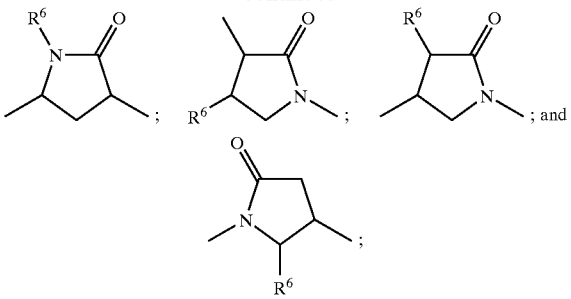

$R^6$ is H, $C_1$–$C_6$ alkyl, $C_3$–$C_6$ cycloalkyl; 3- to 6-membered heterocycloalkyl;
  phenyl; benzyl; or 5- or 6-membered heteroaryl;
X is O, S, N(H), or N($C_1$–$C_6$ alkyl);
Each V is independently C(H) or N;
Y is C(═O), $CH_2$; C(H)($R^7$), C($R^7$)$_2$; O; S; S(O); or S(O)$_2$;
Each $R^7$ is independently $C_1$–$C_6$ alkyl, $H_2N$; HO; or halo;
——— means a bond which is optionally present or absent;
$W^1$ is independently N—$R^5$ or C(H)$R^5$ when ——— is absent, wherein $R^5$ is as defined above;
$W^1$ is independently N or C—$R^5$ when ——— is a bond, wherein $R^5$ is as defined above;
Each $W^2$, $W^3$, and $W^4$ is independently N or C—$R^5$, wherein $R^5$ is as defined above;
wherein at least 1 of $W^1$, $W^2$, $W^3$, and $W^4$ is N;
wherein each $C_8$–$C_{10}$ bicycloalkyl is a bicyclic carbocyclic ring that contains 8-, 9-, or 10-member carbon atoms which are 5,5-fused, 6,5-fused, or 6,6-fused bicyclic rings, respectively, and wherein the ring is saturated or optionally contains one carbon-carbon double bond;
wherein each 8- to 10-membered heterobicycloalkyl is a bicyclic ring that contains carbon atoms and from 1 to 4 heteroatoms independently selected from 2 O, 1 S, 1 S(O), 1 S(O)$_2$, 1 N, 4 N(H), and 4 N($C_1$–$C_6$ alkyl), and wherein when two O atoms or one O atom and one S atom are present, the two O atoms or one O atom and one S atom are not bonded to each other, and wherein the ring is saturated or optionally contains one carbon-carbon or carbon-nitrogen double bond, and wherein the heterobicycloalkyl is a 5,5-fused, 6,5-fused, or 6,6-fused bicyclic ring, respectively,
wherein each heterocycloalkyl is a ring that contains carbon atoms and from 1 to 4 heteroatoms independently selected from 2 O, 1 S, 1 S(O), 1 S(O)$_2$, 1 N, 4 N(H), and 4 N($C_1$–$C_6$ alkyl), and wherein when two O atoms or one O atom and one S atom are present, the two O atoms or one O atom and one S atom are not bonded to each other, and wherein the ring is saturated or optionally contains one carbon-carbon or carbon-nitrogen double bond;
wherein each 5-membered heteroaryl contains carbon atoms and from 1 to 4 heteroatoms independently selected from 2 O, 1 S, 1 N(H), 1 N($C_1$–$C_6$ alkyl), and 4 N, and each 6-membered heteroaryl contains carbon atoms and 1 or 2 heteroatoms independently selected from N, N(H), and N($C_1$–$C_6$ alkyl), and 5- and 6-membered heteroaryl are monocyclic rings;
wherein each heterobiaryl contains carbon atoms and from 1 to 4 heteroatoms independently selected from 2 O, 1 S, 1 N(H), 1 N($C_1$–$C_6$ alkyl), and 4 N, and where the 8-, 9-, and 10-membered heterobiaryl are 5,5-fused, 6,5-fused, and 6,6-fused bicyclic rings, respectively, and wherein at least 1 of the 2 fused rings of a bicyclic ring is aromatic, and wherein when the O and S atoms both are present, the O and S atoms are not bonded to each other;

wherein with any (C₁–C₆ alkyl)₂-N group, the $C_1$–$C_6$ alkyl groups may be optionally taken together with the nitrogen atom to which they are attached to form a 5- or 6-membered heterocycloalkyl;

wherein each group and each substituent recited above is independently selected; and wherein the compound named 4-[1-oxo-7-(3-[1,2,3]triazol-1-ylprop-1-ynyl)-1H-isoquinolin-2-ylmethyl]benzoic acid is excluded.

2. The compound according to Embodiment 1, or a pharmaceutically acceptable salt thereof, wherein Y is C(=O).

3. The compound according to Embodiment 1, or a pharmaceutically acceptable salt thereof, wherein Y is $CH_2$.

4. The compound according to Embodiment 1, or a pharmaceutically acceptable salt thereof, wherein Y is $C(H)(R^7)$, wherein $R^7$ is $C_1$–$C_6$ alkyl, $H_2N$, HO, or halo.

5. The compound according to Embodiment 1, or a pharmaceutically acceptable salt thereof, wherein Y is $C(R^7)_2$, wherein each $R^7$ is independently $C_1$–$C_6$ alkyl, $H_2N$, HO, or halo.

6. The compound according to Embodiment 1, or a pharmaceutically acceptable salt thereof, wherein Y is O.

7. The compound according to Embodiment 1, or a pharmaceutically acceptable salt thereof, wherein Y is S.

8. The compound according to Embodiment 1, or a pharmaceutically acceptable salt thereof, wherein Y is S(O).

9. The compound according to Embodiment 1, or a pharmaceutically acceptable salt thereof, wherein Y is $S(O)_2$.

10. The compound according to any one of Embodiments 1 to 9, or a pharmaceutically acceptable salt thereof, wherein Q is OC(O).

11. The compound according to any one of Embodiments 1 to 9, or a pharmaceutically acceptable salt thereof, wherein Q is $CH(R^6)C(O)$.

12. The compound according to any one of Embodiments 1 to 9, or a pharmaceutically acceptable salt thereof, wherein Q is $OC(NR^6)$.

13. The compound according to any one of Embodiments 1 to 9, or a pharmaceutically acceptable salt thereof, wherein Q is $CH(R^6)C(NR^6)$.

14. The compound according to any one of Embodiments 1 to 9, or a pharmaceutically acceptable salt thereof, wherein Q is $N(R^6)C(O)$.

15. The compound according to any one of Embodiments 1 to 9, or a pharmaceutically acceptable salt thereof, wherein Q is $N(R^6)C(NR^6)$.

16. The compound according to any one of Embodiments 1 to 9, or a pharmaceutically acceptable salt thereof, wherein Q is $N(R^6)CH_2$.

17. The compound according to any one of Embodiments 1 to 9, or a pharmaceutically acceptable salt thereof, wherein Q is SC(O).

18. The compound according to any one of Embodiments 1 to 9, or a pharmaceutically acceptable salt thereof, wherein Q is $CH(R^6)C(S)$.

19. The compound according to any one of Embodiments 1 to 9, or a pharmaceutically acceptable salt thereof, wherein Q is $SC(NR^6)$.

20. The compound according to any one of Embodiments 1 to 9, or a pharmaceutically acceptable salt thereof, wherein Q is C≡C, $CH_2$C≡C, C≡$CCH_2$, $CF_2$C≡C, or C≡$CCF_2$.

21. The compound according to any one of Embodiments 1 to 9, or a pharmaceutically acceptable salt thereof, wherein n is 0.

22. The compound according to any one of Embodiments 1 to 9, or a pharmaceutically acceptable salt thereof, wherein n is 1.

23. The compound according to any one of Embodiments 1 to 9, or a pharmaceutically acceptable salt thereof, wherein n is 2.

24. The compound according to any one of Embodiments 1 to 9, or a pharmaceutically acceptable salt thereof, wherein n is 3.

25. The compound according to any one of Embodiments 1 to 24, or a pharmaceutically acceptable salt thereof, wherein $R^5$ is H.

26. The compound according to any one of Embodiments 1 to 24, or a pharmaceutically acceptable salt thereof, wherein $R^5$ is halo.

27. The compound according to any one of Embodiments 1 to 24, or a pharmaceutically acceptable salt thereof, wherein $R^5$ is $H_2N$.

28. The compound according to any one of Embodiments 1 to 24, or a pharmaceutically acceptable salt thereof, wherein $R^5$ is HO.

29. The compound according to any one of Embodiments 1 to 24, or a pharmaceutically acceptable salt thereof, wherein $R^5$ is $CH_3$.

30. The compound according to any one of Embodiments 1 to 29, or a pharmaceutically acceptable salt thereof, wherein $R^3$ and $R^4$ is H.

31. The compound according to any one of Embodiments 1 to 29, or a pharmaceutically acceptable salt thereof, wherein one of the groups $R^3$ and $R^4$ is H and the other group is $CH_3$.

32. The compound according to any one of Embodiments 1 to 29, or a pharmaceutically acceptable salt thereof, wherein the groups $R^3$ and $R^4$ are taken together to form O—$CH_2$—O.

33. The compound according to any one of Embodiments 1 to 29, or a pharmaceutically acceptable salt thereof, wherein one of the groups $R^3$ and $R^4$ is H and the other group is HO.

34. The compound according to any one of Embodiments 1 to 29, or a pharmaceutically acceptable salt thereof, wherein one of the groups $R^3$ and $R^4$ is H and the other group is $CH_3O$.

35. The compound according to any one of Embodiments 1 to 34, or a pharmaceutically acceptable salt thereof, wherein at least one of $R^1$ and $R^2$ is independently selected from:

Phenyl-($C_1$–$C_8$ alkylenyl); and

Substituted phenyl-($C_1$–$C_8$ alkylenyl);

wherein each group and each substituent is independently selected.

36. The compound according to any one of Embodiments 1 to 34, or a pharmaceutically acceptable salt thereof, wherein each of $R^1$ and $R^2$ are independently selected from:

Phenyl-($C_1$–$C_8$ alkylenyl); and

Substituted phenyl-($C_1$–$C_8$ alkylenyl);

wherein each group and each substituent is independently selected.

37. The compound according to any one of Embodiments 1 to 34, or a pharmaceutically acceptable salt thereof, wherein at least one of $R^1$ and $R^2$ is independently selected from:

5- or 6-membered heteroaryl-($C_1$–$C_8$ alkylenyl); and

Substituted 5- or 6-membered heteroaryl-($C_1$–$C_8$ alkylenyl);

wherein each group and each substituent is independently selected.

38. The compound according to any one of Embodiments 1 to 34, or a pharmaceutically acceptable salt thereof, wherein at least one of $R^1$ and $R^2$ is independently selected from:

8- to 10-membered heterobiaryl-($C_1$–$C_8$ alkylenyl); and

Substituted 8- to 10-membered heterobiaryl-($C_1$–$C_8$ alkylenyl);

wherein each group and each substituent is independently selected.

39. The compound according to any one of Embodiments 1 to 34, or a pharmaceutically acceptable salt thereof, wherein each of $R^1$ and $R^2$ is independently selected from:
   5- or 6-membered heteroaryl-($C_1$–$C_8$ alkylenyl);
   Substituted 5- or 6-membered heteroaryl-($C_1$–$C_8$ alkylenyl);
   8- to 10-membered heterobiaryl-($C_1$–$C_8$ alkylenyl); and
   Substituted 8- to 10-membered heterobiaryl-($C_1$–$C_8$ alkylenyl);
wherein each group and each substituent is independently selected.

40. The compound according to any one of Embodiments 1 to 34, or a pharmaceutically acceptable salt thereof, wherein each of $R^1$ and $R^2$ is independently selected from:
   5- or 6-membered heteroaryl-($C_1$–$C_8$ alkylenyl); and
   Substituted 5- or 6-membered heteroaryl-($C_1$–$C_8$ alkylenyl);
wherein each group and each substituent is independently selected.

41. The compound according to any one of Embodiments 1 to 34, 35, and 37, or a pharmaceutically acceptable salt thereof, wherein one of $R^1$ and $R^2$ is independently selected from:
   5- or 6-membered heteroaryl-($C_1$–$C_8$ alkylenyl);
   Substituted 5- or 6-membered heteroaryl-($C_1$–$C_8$ alkylenyl);
   8- to 10-membered heterobiaryl-($C_1$–$C_8$ alkylenyl); and
   Substituted 8- to 10-membered heterobiaryl-($C_1$–$C_8$ alkylenyl); and
the other one of $R^1$ and $R^2$ is independently selected from:
   Phenyl-($C_1$–$C_8$ alkylenyl); and
   Substituted phenyl-($C_1$–$C_8$ alkylenyl);
   wherein each group and each substituent is independently selected.

42. The compound according to any one of Embodiments 1 to 34, 35, and 37, or a pharmaceutically acceptable salt thereof, wherein $R^1$ is independently selected from:
   5- or 6-membered heteroaryl-($C_1$–$C_8$ alkylenyl);
   Substituted 5- or 6-membered heteroaryl-($C_1$–$C_8$ alkylenyl);
   8- to 10-membered heterobiaryl-($C_1$–$C_8$ alkylenyl);
   Substituted 8- to 10-membered heterobiaryl-($C_1$–$C_8$ alkylenyl);
   Phenyl-($C_1$–$C_8$ alkylenyl); and
   Substituted phenyl-($C_2$–$C_8$ alkylenyl); and
$R^2$ is independently selected from:
   Phenyl-($C_1$–$C_8$ alkylenyl); and
   Substituted phenyl-($C_1$–$C_8$ alkylenyl);
   wherein each group and each substituent is independently selected.

43. The compound according to any one of Embodiments 1 to 34, 35, 37, and 42, or a pharmaceutically acceptable salt thereof, wherein $R^1$ is independently selected from:
   5- or 6-membered heteroaryl-($C_1$–$C_8$ alkylenyl);
   Substituted 5- or 6-membered heteroaryl-($C_1$–$C_8$ alkylenyl);
   Phenyl-($C_1$–$C_8$ alkylenyl); and
   Substituted phenyl-($C_1$–$C_8$ alkylenyl); and
$R^2$ is independently selected from:
   Phenyl-($C_1$–$C_8$ alkylenyl); and
   Substituted phenyl-($C_1$–$C_8$ alkylenyl);
wherein each group and each substituent is independently selected.

44. The compound according to any one of Embodiments 1 to 34, or a pharmaceutically acceptable salt thereof, wherein at least one of $R^1$ and $R^2$ is independently selected from:
   3- to 6-membered heterocycloalkyl-($C_1$–$C_8$ alkylenyl); and
   Substituted 3- to 6-membered heterocycloalkyl-($C_1$–$C_8$ alkylenyl) and
wherein each group and each substituent recited above is independently selected.

45. The compound according to any one of Embodiments 1 to 34, or a pharmaceutically acceptable salt thereof, wherein at least one of $R^3$ and $R^4$ is independently selected from:
   $C_2$–$C_6$ alkenyl; and
   Substituted $C_2$–$C_6$ alkenyl.

46. The compound according to any one of Embodiments 1 to 34, or a pharmaceutically acceptable salt thereof, wherein at least one of $R^3$ and $R^4$ is independently selected from:
   $C_1$–$C_6$ alkyl; and
   Substituted $C_1$–$C_6$ alkyl.

47. The compound according to any one of Embodiments 1 to 34, or a pharmaceutically acceptable salt thereof, wherein at least one of $R^3$ and $R^4$ is independently selected from:
   $C_2$–$C_6$ alkynyl; and
   Substituted $C_2$–$C_6$ alkynyl.

48. The compound according to any one of Embodiments 1 to 34, or a pharmaceutically acceptable salt thereof, wherein at least one of $R^1$ and $R^2$ is independently selected from:
   $C_3$–$C_6$ cycloalkyl-($C_1$–$C_8$ alkylenyl); and
   Substituted $C_3$–$C_6$ cycloalkyl-($C_1$–$C_8$ alkylenyl).

49. The compound according to any one of Embodiments 1 to 34, or a pharmaceutically acceptable salt thereof, wherein at least one of $R^1$ and $R^2$ is independently selected from:
   $C_3$–$C_6$ cycloalkyl;
   Substituted $C_3$–$C_6$ cycloalkyl
   3- to 6-membered heterocycloalkyl;
   Substituted 3- to 6-membered heterocycloalkyl;
   Phenyl;
   Substituted phenyl;
   Naphthyl;
   Substituted naphthyl;
   5- or 6-membered heteroaryl;
   Substituted 5- or 6-membered heteroaryl;
   8- to 10-membered heteroaryl; and
   Substituted 8- to 10-membered heteroaryl.

50. The compound according to any one of Embodiments 1 to 9 and 21 to 49, or a pharmaceutically acceptable salt thereof, wherein Q is selected from:

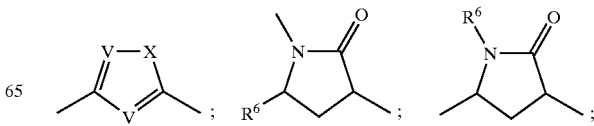

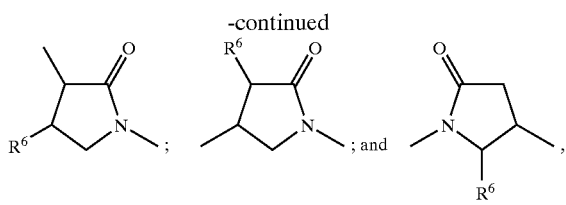

wherein V, X, and $R^6$ are as defined above.

51. The compound according to any one of Embodiments 1 to 50, or a pharmaceutically acceptable salt thereof, wherein each $C_1$–$C_8$ alkylenyl is $CH_2$, $C(CH_3)_2$, $C(=O)$, or $CF_2$.

52. The compound according to any one of Embodiments 1 to 51, or a pharmaceutically acceptable salt thereof, wherein each $C_1$–$C_8$ alkylenyl is $CH_2$.

53. The compound according to any one of Embodiments 1 to 52, or a pharmaceutically acceptable salt thereof, wherein at least one substituent is selected from the groups:

$CO_2H$;
$CO_2CH_3$;
F;
Cl;
CN;
$CF_3$;
$H_2NS(O)_2$; or wherein at least two substituents are each F, or
wherein at least three substituents are 2 F and 1 HO.

54. A compound of Formula II

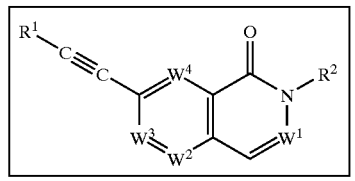

II or a pharmaceutically acceptable salt thereof,
wherein:
$R^1$ is independently selected from:
$C_5$ or $C_6$ cycloalkyl-($C_1$–$C_8$ alkylenyl);
Substituted $C_5$ or $C_6$ cycloalkyl-($C_1$–$C_8$ alkylenyl);
$C_8$–$C_{10}$ bicycloalkyl-($C_1$–$C_8$ alkylenyl);
Substituted $C_8$–$C_{10}$ bicycloalkyl-($C_1$–$C_8$ alkylenyl);
5- or 6-membered heterocycloalkyl-($C_1$–$C_8$ alkylenyl);
Substituted 5- or 6-membered heterocycloalkyl-($C_1$–$C_8$ alkylenyl);
8- to 10-membered heterobicycloalkyl-($C_1$–$C_8$ alkylenyl);
Substituted 8- to 10-membered heterobicycloalkyl-($C_1$–$C_8$ alkylenyl);
Phenyl-($C_1$–$C_8$ alkylenyl);
Substituted phenyl-($C_1$–$C_8$ alkylenyl);
Naphthyl-($C_1$–$C_8$ alkylenyl);
Substituted naphthyl-($C_1$–$C_8$ alkylenyl);
5- or 6-membered heteroaryl-($C_1$–$C_8$ alkylenyl);
Substituted 5- or 6-membered heteroaryl-($C_1$–$C_8$ alkylenyl);
8- to 10-membered heterobiaryl-($C_1$–$C_8$ alkylenyl);
Substituted 8- to 10-membered heterobiaryl-($C_1$–$C_8$ alkylenyl);
Phenyl;
Substituted phenyl;
Naphthyl;
Substituted naphthyl;
5- or 6-membered heteroaryl;
Substituted 5- or 6-membered heteroaryl;
8- to 10-membered heterobiaryl; and
Substituted 8- to 10-membered heterobiaryl;

$R^2$ is independently selected from:
H;
$C_1$–$C_6$ alkyl;
Phenyl-($C_1$–$C_8$ alkylenyl);
Substituted phenyl-($C_1$–$C_8$ alkylenyl);
Naphthyl-($C_1$–$C_8$ alkylenyl);
Substituted naphthyl-($C_1$–$C_8$ alkylenyl);
5- or 6-membered heteroaryl-($C_1$–$C_8$ alkylenyl);
Substituted 5- or 6-membered heteroaryl-($C_1$–$C_8$ alkylenyl);
8- to 10-membered heterobiaryl-($C_1$–$C_8$ alkylenyl);
Substituted 8- to 10-membered heterobiaryl-($C_1$–$C_8$ alkylenyl);
Phenyl-O-($C_1$–$C_8$ alkylenyl);
Substituted phenyl-O-($C_1$–$C_8$ alkylenyl);
Phenyl-S-($C_1$–$C_8$ alkylenyl);
Substituted phenyl-S-($C_1$–$C_8$ alkylenyl);
Phenyl-S(O)-($C_1$–$C_8$ alkylenyl);
Substituted phenyl-S(O)-($C_1$–$C_8$ alkylenyl);
Phenyl-S(O)$_2$-($C_1$–$C_8$ alkylenyl); and
Substituted phenyl-S(O)$_2$-($C_1$–$C_8$ alkylenyl);

Each substituted $R^1$ and $R^2$ group contains from 1 to 4 substituents, each independently on a carbon or nitrogen atom, independently selected from:
$C_1$–$C_6$ alkyl;
CN;
$CF_3$;
HO;
($C_1$–$C_6$ alkyl)-O;
($C_1$–$C_6$ alkyl)-S(O)$_2$;
$H_2N$;
($C_1$–$C_6$ alkyl)-N(H);
($C_1$–$C_6$ alkyl)$_2$-N;
($C_1$–$C_6$ alkyl)-C(O)O-($C_1$–$C_8$ alkylenyl)$_m$;
($C_1$–$C_6$ alkyl)-C(O)O-(1- to 8-membered heteroalkylenyl)$_m$;
($C_1$–$C_6$ alkyl)-C(O)N(H)—($C_1$–$C_8$ alkylenyl)$_m$;
($C_1$–$C_6$ alkyl)-C(O)N(H)-(1- to 8-membered heteroalkylenyl)$_m$;
$H_2NS(O)_2$—($C_1$–$C_8$ alkylenyl);
($C_1$–$C_6$ alkyl)-N(H)S(O)$_2$($C_1$–$C_8$ alkylenyl)$_m$;
($C_1$–$C_6$ alkyl)$_2$-NS(O)$_2$—($C_1$–$C_8$ alkylenyl)$_m$;
3- to 6-membered heterocycloalkyl-(G)$_m$;
Substituted 3- to 6-membered heterocycloalkyl-(G)$_m$;
5- or 6-membered heteroaryl-(G)$_m$;
Substituted 5- or 6-membered heteroaryl-(G)$_m$;
($C_1$–$C_6$ alkyl)-S(O)$_2$—N(H)—C(O)—($C_1$–$C_8$ alkylenyl)$_m$; and
($C_1$–$C_6$ alkyl)-C(O)—N(H)—S(O)$_2$—($C_1$–$C_8$ alkylenyl)$_m$;

wherein each substituent on a carbon atom may further be independently selected from:
  Halo; and
  $HO_2C$;
wherein 2 substituents may be taken together with a carbon atom to which they are both bonded to form the group C=O;
wherein two adjacent, substantially $sp^2$ carbon atoms may be taken together with a diradical substituent to form a cyclic diradical selected from:

[chemical structures]

R is H or $C_1-C_6$ alkyl;
G is $CH_2$; O, S, S(O); or $S(O)_2$;
Each m is an integer of 0 or 1;
$W^1$ is independently N or C—$R^5$, wherein $R^5$ is as defined above;
Each W2, W3, and $W^4$ is independently N or C—$R^5$, wherein $R^5$ is as defined above;
wherein at least 1 of $W^1$, $W^2$, $W^3$, and $W^4$ is N;
wherein each $C_8-C_{10}$ bicycloalkyl is a bicyclic carbocyclic ring that contains 8-, 9-, or 10-member carbon atoms which are 5,5-fused, 6,5-fused, or 6,6-fused bicyclic rings, respectively, and wherein the ring is saturated or optionally contains one carbon-carbon double bond;
wherein each 8- to 10-membered heterobicycloalkyl is a bicyclic ring that contains carbon atoms and from 1 to 4 heteroatoms independently selected from 2 O, 1 S, 1 S(O), 1 $S(O)_2$, 1 N, 4 N(H), and 4 N($C_1-C_6$ alkyl), and wherein when two O atoms or one O atom and one S atom are present, the two O atoms or one O atom and one S atom are not bonded to each other, and wherein the ring is saturated or optionally contains one carbon-carbon or carbon-nitrogen double bond, and wherein the heterobicycloalkyl is a 5,5-fused, 6,5-fused, or 6,6-fused bicyclic ring, respectively,
wherein each heterocycloalkyl is a ring that contains carbon atoms and from 1 to 4 heteroatoms independently selected from 2 O, 1 S, 1 S(O), 1 $S(O)_2$, 1 N, 4 N(H), and 4 N($C_1-C_6$ alkyl), and wherein when two O atoms or one O atom and one S atom are present, the two O atoms or one O atom and one S atom are not bonded to each other, and wherein the ring is saturated or optionally contains one carbon-carbon or carbon-nitrogen double bond;
wherein each 5-membered heteroaryl contains carbon atoms and from 1 to 4 heteroatoms independently selected from 2 O, 1 S, 1 N(H), 1 N($C_1-C_6$ alkyl), and 4 N, and each 6-membered heteroaryl contains carbon atoms and 1 or 2 heteroatoms independently selected from N, N(H), and N($C_1-C_6$ alkyl), and 5- and 6-membered heteroaryl are monocyclic rings;
wherein each heterobiaryl contains carbon atoms and from 1 to 4 heteroatoms independently selected from 2 O, 1 S, 1 N(H), 1 N($C_1-C_6$ alkyl), and 4 N, and where the 8-, 9-, and 10-membered heterobiaryl are 5,5-fused, 6,5-fused, and 6,6-fused bicyclic rings, respectively, and wherein at least 1 of the 2 fused rings of a bicyclic ring is aromatic, and wherein when the O and S atoms both are present, the O and S atoms are not bonded to each other;
wherein with any ($C_1-C_6$ alkyl)$_2$-N group, the $C_1-C_6$ alkyl groups may be optionally taken together with the nitrogen atom to which they are attached to form a 5- or 6-membered heterocycloalkyl;
wherein each group and each substituent recited above is independently selected; and
wherein the compound named 4-[1-oxo-7-(3-[1,2,3]triazol-1-ylprop-1-ynyl)-1H-isoquinolin-2-ylmethyl]benzoic acid is excluded.

55. The compound according to Embodiment 54, or a pharmaceutically acceptable salt thereof, wherein at least one of $R^1$ and $R^2$ is independently selected from:
  Phenyl-($C_1-C_8$ alkylenyl); and
  Substituted phenyl-($C_1-C_8$ alkylenyl);
wherein each group and each substituent is independently selected.

56. The compound according to any one of Embodiments 54 and 55, or a pharmaceutically acceptable salt thereof, wherein each of $R^1$ and $R^2$ are independently selected from:
  Phenyl-($C_1-C_8$ alkylenyl); and
  Substituted phenyl-($C_1-C_8$ alkylenyl);
wherein each group and each substituent is independently selected.

57. The compound according to Embodiment 54, or a pharmaceutically acceptable salt thereof, wherein at least one of $R^1$ and $R^2$ is independently selected from:
  5- or 6-membered heteroaryl-($C_1-C_8$ alkylenyl); and
  Substituted 5- or 6-membered heteroaryl-($C_1-C_8$ alkylenyl);
wherein each group and each substituent is independently selected.

58. The compound according to Embodiment 54, or a pharmaceutically acceptable salt thereof, wherein at least one of $R^1$ and $R^2$ is independently selected from:
  8- to 10-membered heterobiaryl-($C_1-C_8$ alkylenyl); and
  Substituted 8- to 10-membered heterobiaryl-($C_1-C_8$ alkylenyl);
wherein each group and each substituent is independently selected.

59. The compound according to any one of Embodiments 54, 57, and 58, or a pharmaceutically acceptable salt thereof, wherein each of $R^1$ and $R^2$ is independently selected from:
  5- or 6-membered heteroaryl-($C_1-C_8$ alkylenyl);
  Substituted 5- or 6-membered heteroaryl-($C_1-C_8$ alkylenyl);
  8- to 10-membered heterobiaryl-($C_1-C_8$ alkylenyl); and
  Substituted 8- to 10-membered heterobiaryl-($C_1-C_8$ alkylenyl);

wherein each group and each substituent is independently selected.

60. The compound according to any one of Embodiments 54, 57, and 59, or a pharmaceutically acceptable salt thereof, wherein each of $R^1$ and $R^2$ is independently selected from:
  5- or 6-membered heteroaryl-($C_1$–$C_8$ alkylenyl); and
  Substituted 5- or 6-membered heteroaryl-($C_1$–$C_8$ alkylenyl);
wherein each group and each substituent is independently selected.

61. The compound according to any one of Embodiments 54, 55, 57, and 58, or a pharmaceutically acceptable salt thereof, wherein one of $R^1$ and $R^2$ is independently selected from:
  5- or 6-membered heteroaryl-($C_1$–$C_8$ alkylenyl);
  Substituted 5- or 6-membered heteroaryl-($C_1$–$C_8$ alkylenyl);
  8- to 10-membered heterobiaryl-($C_1$–$C_8$ alkylenyl); and
  Substituted 8- to 10-membered heterobiaryl-($C_1$–$C_8$ alkylenyl); and
the other one of $R^1$ and $R^2$ is independently selected from:
  Phenyl-($C_1$–$C_8$ alkylenyl); and
  Substituted phenyl-($C_1$–$C_8$ alkylenyl);
  wherein each group and each substituent is independently selected.

62. The compound according to any one of Embodiments 54, 55, 57, 58, and 59, or a pharmaceutically acceptable salt thereof, wherein $R^1$ is independently selected from:
  5- or 6-membered heteroaryl-($C_1$–$C_8$ alkylenyl);
  Substituted 5- or 6-membered heteroaryl-($C_1$–$C_8$ alkylenyl);
  8- to 10-membered heterobiaryl-($C_1$–$C_8$ alkylenyl);
  Substituted 8- to 10-membered heterobiaryl-($C_1$–$C_8$ alkylenyl);
  Phenyl-($C_1$–$C_8$ alkylenyl); and
  Substituted phenyl-($C_1$–$C_8$ alkylenyl); and
$R^2$ is independently selected from:
  Phenyl-($C_1$–$C_8$ alkylenyl); and
  Substituted phenyl-($C_1$–$C_8$ alkylenyl);
  wherein each group and each substituent is independently selected.

63. The compound according to any one of Embodiments 54, 55, 57, 58, 59, and 60, or a pharmaceutically acceptable salt thereof, wherein $R^1$ is independently selected from:
  5- or 6-membered heteroaryl-($C_1$–$C_8$ alkylenyl);
  Substituted 5- or 6-membered heteroaryl-($C_1$–$C_8$ alkylenyl);
  Phenyl-($C_1$–$C_8$ alkylenyl); and
  Substituted phenyl-($C_1$–$C_8$ alkylenyl); and
$R^2$ is independently selected from:
  Phenyl-($C_1$–$C_8$ alkylenyl); and
  Substituted phenyl-($C_1$–$C_8$ alkylenyl);
wherein each group and each substituent is independently selected.

64. The compound according to Embodiment 54, or a pharmaceutically acceptable salt thereof, wherein at least one of $R^1$ and $R^2$ is independently selected from:
  3- to 6-membered heterocycloalkyl-($C_1$–$C_8$ alkylenyl); and
  Substituted 3- to 6-membered heterocycloalkyl-($C_1$–$C_8$ alkylenyl) and
wherein each group and each substituent recited above is independently selected.

65. The compound according to Embodiment 54, or a pharmaceutically acceptable salt thereof, wherein at least one of $R^3$ and $R^4$ is independently selected from:
  $C_2$–$C_6$ alkenyl; and
  Substituted $C_2$–$C_6$ alkenyl.

66. The compound according to Embodiment 54, or a pharmaceutically acceptable salt thereof, wherein at least one of $R^3$ and $R^4$ is independently selected from:
  $C_2$–$C_6$ alkynyl; and
  Substituted $C_2$–$C_6$ alkynyl.

67. The compound according to any one of Embodiments 54 to 68, or a pharmaceutically acceptable salt thereof, wherein each $C_1$–$C_8$ alkylenyl is $CH_2$.

68. The compound according to Embodiment 54, selected from:
  4-[1-Oxo-7-(3-phenyl-prop-1-ynyl)-1H-3-azaisoquinolin-2-ylmethyl]benzoic acid tert-butyl ester;
  4-[1-Oxo-7-(3-phenyl-prop-1-ynyl)-1H-3-azaisoquinolin-2-ylmethyl]benzoic acid;
  2-(3,5-Difluoro-4-hydroxybenzyl)-7-[3-(4H-[1,2,3]triazol-4-yl)prop-1-ynyl]-2H-3-azaisoquinolin-1-one; or
  a pharmaceutically acceptable salt thereof.

69. The compound according to Embodiment 54, selected from:
  7-(3-Phenyl-prop-1-ynyl)-2-(4-trifluoromethylbenzyl)-2H-5-azaisoquinolin-1-one;
  2-(3-Fluorobenzyl)-7-(3-phenyl-prop-1-ynyl)-2H-5-azaisoquinolin-1-one;
  4-[7-(3-Imidazol-1-ylprop-1-ynyl)-1-oxo-1H-5-azaisoquinolin-2-ylmethyl]benzoic acid tert-butyl ester;
  4-[7-(3-Imidazol-1-ylprop-1-ynyl)-1-oxo-1H-5-azaisoquinolin-2-ylmethyl]benzoic acid; or
  a pharmaceutically acceptable salt thereof.

70. The compound according to Embodiment 54, selected from:
  3-[1-Oxo-7-(3-phenyl-prop-1-ynyl)-1H-6-azaisoquinolin-2-ylmethyl]benzonitrile;
  4-[1-Oxo-7-(3-phenyl-prop-1-ynyl)-1H-6-azaisoquinolin-2-ylmethyl]benzenesulfonamide;
  4-[1-Oxo-7-(3-[1,2,3]triazol-1-ylprop-1-ynyl)-1H-6-azaisoquinolin-2-ylmethyl]benzoic acid tert-butyl ester;
  4-[1-Oxo-7-(3-[1,2,3]triazol-1-ylprop-1-ynyl)-1H-6-azaisoquinolin-2-ylmethyl]benzoic acid; or
  a pharmaceutically acceptable salt thereof.

71. The compound according to Embodiment 54, selected from:
  4-[1-Oxo-7-(3-phenyl-prop-1-ynyl)-1H-8-azaisoquinolin-2-ylmethyl]benzoic acid methyl ester;
  3-[1-Oxo-7-(3-phenyl-prop-1-ynyl)-1H-8-azaisoquinolin-2-ylmethyl]benzoic acid methyl ester; or
  a pharmaceutically acceptable salt thereof.

72. The compound according to Embodiment 54, named:
  2-(4-Fluorobenzyl)-7-3-phenylprop-1-ynyl-2H-3,5-diazaisoquinolin-1-one; or
  a pharmaceutically acceptable salt thereof.

73. The compound according to Embodiment 54, named:
7-(3-Phenylprop-1-ynyl)-2-(3-trifluoromethylbenzyl)-2H-3,6-diazaisoquinolin-1-one; or
a pharmaceutically acceptable salt thereof.

74. The compound according to Embodiment 54, named:
2-(3-Chlorobenzyl)-7-(3-phenylprop-1-ynyl)-2H-3,8-diazaisoquinolin-1-one; or
a pharmaceutically acceptable salt thereof.

75. The compound according to Embodiment 54, named:
2-(3,4-Difluorobenzyl)-7-(3-phenylprop-1-ynyl)-2H-5,8-diazaisoquinolin-1-one; or
a pharmaceutically acceptable salt thereof.

76. The compound according to Embodiment 54, named:
4-[1-Oxo-7-(3-[1,2,4]triazol-1-ylprop-1-ynyl)-1H-3,5,8-triazaisoquinolin-2-ylmethyl]benzoic acid tert-butyl ester; or
a pharmaceutically acceptable salt thereof.

77. A pharmaceutical composition, comprising a compound of Formula I according to Embodiment 1, or a pharmaceutically acceptable salt thereof, admixed with a pharmaceutically acceptable carrier, excipient, or diluent.

78. The pharmaceutical composition according to Embodiment 77, comprising a compound of Formula I according to any one of Embodiments 2 to 76, or a pharmaceutically acceptable salt thereof, admixed with a pharmaceutically acceptable carrier, excipient, or diluent.

79. A method for inhibiting an MMP-13 enzyme in an animal, comprising administering to the animal an MMP-13 inhibiting amount of a compound of Formula I according to Embodiment 1, or a pharmaceutically acceptable salt thereof.

80. The method according to Embodiment 79, wherein the compound of Formula I is according to any one of Embodiments 2 to 76, or a pharmaceutically acceptable salt thereof.

81. A method for treating a disease mediated by an MMP-13 enzyme, comprising administering to a patient suffering from such a disease a nontoxic effective amount of a compound of Formula I according to Embodiment 1, or a pharmaceutically acceptable salt thereof.

82. The method according to Embodiment 81, wherein the compound of Formula I is according to any one of Embodiments 2 to 76, or a pharmaceutically acceptable salt thereof.

83. A method for treating arthritis, comprising administering to a patient suffering from an arthritis disease a nontoxic antiarthritic effective amount of a compound of Formula I according to Embodiment 1, or a pharmaceutically acceptable salt thereof.

84. The method according to Embodiment 83, wherein the compound of Formula I is according to any one of Embodiments 2 to 76, or a pharmaceutically acceptable salt thereof.

85. A method for treating osteoarthritis, comprising administering to a patient suffering from osteoarthritis a nontoxic effective amount of a compound of Formula I according to Embodiment 1, or a pharmaceutically acceptable salt thereof.

86. The method according to Embodiment 85, wherein the compound of Formula I is according to any one of Embodiments 2 to 76, or a pharmaceutically acceptable salt thereof.

87. A method for treating rheumatoid arthritis, comprising administering to a patient suffering from rheumatoid arthritis a nontoxic effective amount of a compound of Formula I according to Embodiment 1, or a pharmaceutically acceptable salt thereof.

88. The method according to Embodiment 87, wherein the compound of Formula I is according to any one of Embodiments 2 to 76, or a pharmaceutically acceptable salt thereof.

89. A method for treating psoriatic arthritis, comprising administering to a patient suffering from psoriatic arthritis a nontoxic effective amount of a compound of Formula I according to Embodiment 1, or a pharmaceutically acceptable salt thereof.

90. The method according to Embodiment 89, wherein the compound of Formula I is according to any one of Embodiments 2 to 76, or a pharmaceutically acceptable salt thereof.

91. A method for treating a cancer, comprising administering to a patient suffering from a cancer a nontoxic anti-cancer effective amount of a compound of Formula I according to Embodiment 1, or a pharmaceutically acceptable salt thereof.

92. The method according to Embodiment 91, wherein the compound of Formula I is according to any one of Embodiments 2 to 76, or a pharmaceutically acceptable salt thereof.

93. A method for treating breast carcinoma, comprising administering to a patient suffering from breast carcinoma a nontoxic effective amount of a compound of Formula I according to Embodiment 1, or a pharmaceutically acceptable salt thereof.

94. The method according to Embodiment 93, wherein the compound of Formula I is according to any one of Embodiments 2 to 76, or a pharmaceutically acceptable salt thereof.

95. A method for treating atherosclerosis, comprising administering to a patient suffering from atherosclerosis a nontoxic effective amount of a compound of Formula I according to Embodiment 1, or a pharmaceutically acceptable salt thereof.

96. The method according to Embodiment 95, wherein the compound of Formula I is according to any one of Embodiments 2 to 76, or a pharmaceutically acceptable salt thereof.

97. A method for treating inflammation, comprising administering to a patient suffering from inflammation a nontoxic effective amount of a compound of Formula I according to Embodiment 1, or a pharmaceutically acceptable salt thereof.

98. The method according to Embodiment 97, wherein the compound of Formula I is according to any one of Embodiments 2 to 76, or a pharmaceutically acceptable salt thereof.

99. A method for treating heart failure, comprising administering to a patient suffering from heart failure a nontoxic effective amount of a compound of Formula I according to Embodiment 1, or a pharmaceutically acceptable salt thereof.

100. The method according to Embodiment 99, wherein the compound of Formula I is according to any one of Embodiments 2 to 76, or a pharmaceutically acceptable salt thereof.

101. A method for treating age-related macular degeneration, comprising administering to a patient suffering from age-related macular degeneration a nontoxic effective amount of a compound of Formula I according to Embodiment 1, or a pharmaceutically acceptable salt thereof.

102. The method according to Embodiment 101, wherein the compound of Formula I is according to any one of Embodiments 2 to 76, or a pharmaceutically acceptable salt thereof.

103. A method for treating chronic obstructive pulmonary disease, comprising administering to a patient suffering from chronic obstructive pulmonary disease a nontoxic effective amount of a compound of Formula I according to Embodiment 1, or a pharmaceutically acceptable salt thereof.

104. The method according to Embodiment 103, wherein the compound of Formula I is according to any one of Embodiments 2 to 76, or a pharmaceutically acceptable salt thereof.

105. A method for treating heart disease, comprising administering to a patient suffering from heart disease a nontoxic effective amount of a compound of Formula I according to Embodiment 1, or a pharmaceutically acceptable salt thereof.

106. The method according to Embodiment 105, wherein the compound of Formula I is according to any one of Embodiments 2 to 76, or a pharmaceutically acceptable salt thereof.

107. A method for treating multiple sclerosis, comprising administering to a patient suffering from multiple sclerosis a nontoxic effective amount of a compound of Formula I according to Embodiment 1, or a pharmaceutically acceptable salt thereof.

108. The method according to Embodiment 107, wherein the compound of Formula I is according to any one of Embodiments 2 to 76, or a pharmaceutically acceptable salt thereof.

109. A method for treating psoriasis, comprising administering to a patient suffering from psoriasis a nontoxic effective amount of a compound of Formula I according to Embodiment 1, or a pharmaceutically acceptable salt thereof.

110. The method according to Embodiment 109, wherein the compound of Formula I is according to any one of Embodiments 2 to 76, or a pharmaceutically acceptable salt thereof.

111. A method for treating asthma, comprising administering to a patient suffering from asthma a nontoxic effective amount of a compound of Formula I according to Embodiment 1, or a pharmaceutically acceptable salt thereof.

112. The method according to Embodiment 111, wherein the compound of Formula I is according to any one of Embodiments 2 to 76, or a pharmaceutically acceptable salt thereof.

113. A method for treating cardiac insufficiency, comprising administering to a patient suffering from cardiac insufficiency a nontoxic effective amount of a compound of Formula I according to Embodiment 1, or a pharmaceutically acceptable salt thereof.

114. The method according to Embodiment 113, wherein the compound of Formula I is according to any one of Embodiments 2 to 76, or a pharmaceutically acceptable salt thereof.

115. A method for treating inflammatory bowel disease, comprising administering to a patient suffering from inflammatory bowel disease a nontoxic effective amount of a compound of Formula I according to Embodiment 1, or a pharmaceutically acceptable salt thereof.

116. The method according to Embodiment 115, wherein the compound of Formula I is according to any one of Embodiments 2 to 76, or a pharmaceutically acceptable salt thereof.

117. A method for treating osteoporosis, comprising administering to a patient suffering from osteoporosis a nontoxic effective amount of a compound of Formula I according to Embodiment 1, or a pharmaceutically acceptable salt thereof.

118. The method according to Embodiment 117, wherein the compound of Formula I is according to any one of Embodiments 2 to 76, or a pharmaceutically acceptable salt thereof.

119. A method for treating periodontal diseases, comprising administering to a patient suffering from periodontal diseases a nontoxic effective amount of a compound of Formula I according to Embodiment 1, or a pharmaceutically acceptable salt thereof.

120. The method according to Embodiment 119, wherein the compound of Formula I is according to any one of Embodiments 2 to 76, or a pharmaceutically acceptable salt thereof.

121. The method according to any one of Embodiments 79 to 120, wherein the compound of Formula I according to Embodiment 1, or a pharmaceutically acceptable salt thereof, is administered as a pharmaceutical composition according to Embodiment 77 or 78.

122. The compound according to Embodiment 1, wherein $W^3$ is N and Q is N(H)C(O).

123. The compound according to Embodiment 1, wherein $W^4$ is N and Q is N(H)C(O).

DETAILED DESCRIPTION OF THE INVENTION

This invention provides compounds defined by Formula I $$I$$

[Structure of Formula I showing a ring system with substituents $R^1$, Q, $W^4$, Y, $R^2$, N, $W^1$, $R^3$, $R^4$, $W^2$, $(R^5)_n$, $W^3$]

or a pharmaceutically acceptable salt thereof,
wherein $R^1$, Q, Y, $R^2$, $R_3$, $R^4$, $R^5$, and n are as defined above.

The invention also provides pharmaceutical compositions comprising a compound of Formula I, or a pharmaceutically acceptable salt thereof, as defined above, together with a pharmaceutically acceptable carrier, diluent, or excipient.

The invention also provides methods of inhibiting an MMP-13 enzyme in an animal, comprising administering to the animal a compound of Formula I, or a pharmaceutically acceptable salt thereof.

The invention also provides methods of treating a disease mediated by an MMP-13 enzyme in a patient, comprising administering to the patient a compound of Formula I, or a pharmaceutically acceptable salt thereof, either alone or in a pharmaceutical composition.

The invention also provides methods of treating diseases such as heart disease, multiple sclerosis, osteo- and rheumatoid arthritis, arthritis other than osteo- or rheumatoid arthritis, cardiac insufficiency, inflammatory bowel disease, heart failure, age-related macular degeneration, chronic obstructive pulmonary disease, asthma, periodontal diseases, psoriasis, atherosclerosis, and osteoporosis in a patient, comprising administering to the patient a compound of Formula I, or a pharmaceutically acceptable salt thereof, either alone or in a pharmaceutical composition.

The invention also provides combinations, comprising a compound of Formula I, or a pharmaceutically acceptable salt thereof, together with another pharmaceutically active component as described.

As seen above, the groups of Formula I include "$C_1$–$C_6$ alkyl" groups. $C_1$–$C_6$ alkyl groups are straight and branched carbon chains having from 1 to 6 carbon atoms. Examples of $C_1$–$C_6$ alkyl groups include methyl, ethyl, 1-propyl, 2-propyl, 1-butyl, 2-butyl, 2,2-dimethylethyl, 1-pentyl, 2-pentyl, 2,2-dimethylpropyl, and 1-hexyl.

The phrase "substituted $C_1$–$C_6$ alkyl" means a $C_1$–$C_6$ alkyl group as defined above that is substituted with from 1 to 4 substituents independently selected from the list above. Illustrative examples of substituted $C_1$–$C_6$ alkyl groups include $CH_2OH$, $CF_2OH$, $CH_2C(CH_3)_2CO_2CH_3$, $CF_3$, $C(O)CF_3$, $C(O)$—$CH_3$, $(CH_2)_4$—S—$CH_3$, $CH(CO_2H)CH_2CH_2C(O)NMe_2$, $(CH_2)_5NH$—$C(O)$—$NH_2$, $CH_2$—$CH_2$—$C(H)$-(4-fluorophenyl), $CH(OCH_3)CH_2CH_3$, $CH_2SO_2NH_2$, and $CH(CH_3)CH_2CH_2OC(O)CH_3$.

The term "$C_2$–$C_6$ alkenyl" means a straight or branched, unsubstituted hydrocarbon group having from 2 to 6 carbon atoms and 1 or 2 carbon-carbon double bonds, and include allenyl groups. Typical examples of $C_2$–$C_6$ alkenyl groups include ethenyl, 1-propen-1-yl, 1-propen-2-yl, 2-propen-1-yl, 1-buten-3-yl, 2-penten-2-yl, and 1-hexen-6-yl.

The phrase "substituted $C_2$–$C_6$ alkenyl" means a $C_2$–$C_6$ alkenyl as defined above, which is substituted with from 1 to 4 substituents independently selected from the list above. Illustrative examples of substituted $C_2$–$C_6$ alkenyl groups include C(H)=C(H)CH$_2$OH, CH=CF$_2$, CH$_2$C(H)=C(H)—(CH$_2$)$_2$CF$_2$OH, CH$_2$C(=CH$_2$)CO$_2$CH$_3$, C(H)=C(H)—CF$_3$, CH$_2$—CH$_2$—C(H)=C(H)—C(O)—CH$_3$, C(H)=C(CH$_3$)—S—CH$_3$, C(H)=C(H)—C(H)=C(CH$_3$)—CO$_2$Me, and C(H)=C=C(H)OC(O)CH$_3$.

The term "$C_2$–$C_6$ alkynyl" means a straight or branched, unsubstituted hydrocarbon group having from 2 to 6 carbon atoms and 1 or 2 carbon-carbon triple bonds. Typical examples of $C_2$–$C_6$ alkynyl groups include ethenyl, 1-propyn-1-yl, 1-propyn-3-yl, 1-butyn-3-yl, 2-pentyn-1-yl, and 1-hexyn-6-yl.

The phrase "substituted $C_2$–$C_6$ alkynyl" means a $C_2$–$C_6$ alkynyl as defined above, which is substituted with from 1 to 4 substituents independently selected from the list above. Illustrative examples of substituted $C_2$–$C_6$ alkynyl groups include C≡CCH$_2$OH, C≡CF, CH$_2$C≡C—(CH$_2$)$_2$CF$_2$OH, C≡C—CH$_2$CO$_2$CH$_3$, CH$_2$C≡C—CF$_3$, CH$_2$—CH$_2$—C≡C—C(O)—CH$_3$, C≡C—S—CH$_3$, and C≡C—C(O)OC(O)CH$_3$.

The term "$C_3$–$C_6$ cycloalkyl" means an unsubstituted cyclic hydrocarbon group having from 3 to 6 carbon atoms. $C_3$–$C_6$ cycloalkyl may optionally contain one carbon-carbon double bond. The group $C_3$–$C_6$ cycloalkyl includes cyclopropyl, cyclobutyl, cyclopentyl, cyclopenten-1-yl, cyclopenten-4-yl, and cyclohexyl.

The phrase "substituted $C_3$–$C_6$ cycloalkyl" means a $C_3$–$C_6$ cycloalkyl as defined above, which is substituted with from 1 to 4 substituents independently selected from the list above. Illustrative examples of substituted $C_3$–$C_6$ cycloalkyl groups include 1-hydroxy-cyclopropyl, cyclobutanon-3-yl, 3-(3-phenyl-ureido)-cyclopent-1-yl, and 4-Carboxy-cyclohexyl.

The phrase "3- to 6-membered heterocycloalkyl" means an unsubstituted saturated cyclic group having carbon atoms and 1 or 2 heteroatoms independently selected from 2 O, 1 S, 1 S(O), 1 S(O)$_2$, 1 N, 2 N(H), and 2 N($C_1$–$C_6$ alkyl), wherein when two O atoms or one O atom and one S atom are present, the two O atoms or one O atom and one S atom are not bonded to each other. Optionally, a 3- to 6-membered heterocycloalkyl may contain one carbon-carbon or carbon-nitrogen double bond. Illustrative examples of 3- to 6-membered heterocycloalkyl includes aziridin-1-yl, 1-oxacyclobutan-2-yl, tetrahyrdofuran-3-yl, morpholin-4-yl, 2-thiacyclohex-1-yl, 2-oxo-2-thiacyclohe-1-yl, 2,2-dioxo-2-thiacyclohex-1-yl, and 4-methyl-piperazin-2-yl.

The phrase "substituted 3- to 6-membered heterocycloalkyl" means a 3- to 6-membered heterocycloalkyl as defined above, which is substituted with from 1 to 4 substituents independently selected from the list above. Illustrative examples of substituted 3- to 6-membered heterocycloalkyl include 2-hydroxy-aziridin-1-yl, 3-oxo-1-oxacyclobutan-2-yl, 2,2-dimethyl-tetrahydrofuran-3-yl, 3-Carboxy-morpholin-4-yl, and 1-Cyclopropyl-4-methyl-piperazin-2-yl.

The term "$C_1$–$C_8$ alkylenyl" means a saturated hydrocarbon diradical that is straight or branched and has from 1 to 8 carbon atoms. $C_1$–$C_8$ alkylenyl having from 2 to 8 carbon atoms may optionally independently contain one carbon-carbon double bond. Illustrative examples of $C_1$–$C_8$ alkylenyl include CH$_2$, CH$_2$CH$_2$, C(CH$_3$)H, C(H)(CH$_3$)CH$_2$CH$_2$, and CH$_2$C(H)=C(H)CH$_2$CH$_2$CH$_2$CH$_2$.

The term "1- to 8-membered heteroalkylenyl" means a saturated diradical chain that is straight or branched and contains from 1 to 7 carbon atoms and 1 heteroatom selected from O, S, N(H), and N($C_1$–$C_6$ alkyl). 2- to 8-membered heteroalkylenyl, having from 2 to 8 chain atoms, may optionally independently contain one carbon-carbon double bond. Illustrative examples of 1- to 8-membered heteroalkylenyl include OCH$_2$, CH$_2$CH$_2$O, C(CH$_3$)HS, and CH$_2$C(H)=C(H)CH$_2$N(H)CH$_2$CH$_2$CH$_2$.

The phrase "$C_3$–$C_6$ cycloalkyl-($C_1$–$C_8$ alkylenyl)" means a $C_3$–$C_6$ cycloalkyl, as defined above, bonded through a $C_1$–$C_8$ alkylenyl, as defined above. Illustrative examples of $C_3$–$C_6$ cycloalkyl-($C_1$–$C_8$ alkylenyl include cyclopropylmethyl, 1-Cyclopentyl-hex-2-yl, and 2-Cyclobutyl-but-2-yl.

The phrase "Substituted $C_3$–$C_6$ cycloalkyl-($C_1$–$C_8$ alkylenyl)" means a $C_3$–$C_6$ cycloalkyl-($C_1$–$C_8$ alkylenyl), as defined above, substituted on $C_3$–$C_6$ cycloalkyl and/or $C_1$–$C_8$ alkylenyl with from 1 to 4 substituents, as defined above. Illustrative examples of substituted $C_3$–$C_6$ cycloalkyl-($C_1$–$C_8$ alkylenyl include cyclopropylcarbonyl and 1-(1-aminomethyl-cyclopentyl)-hex-2-yl.

The phrase "$C_5$ or $C_6$ cycloalkyl-($C_1$–$C_8$ alkylenyl)" means a cyclopentyl or cyclohexyl bonded through a $C_1$–$C_8$ alkylenyl, as defined above, wherein the cycloalkyl optionally contains 1 carbon-carbon double bond.

The phrase "Substituted $C_5$ or $C_6$ cycloalkyl-($C_1$–$C_8$ alkylenyl)" means a substituted cyclopentyl or cyclohexyl, wherein the substituents are as defined above, bonded through a $C_1$–$C_8$ alkylenyl, as defined above, wherein the cycloalkyl optionally contains 1 carbon-carbon double bond.

The phrase "$C_8$–$C_{10}$ bicycloalkyl-($C_1$–$C_8$ alkylenyl)" means a cyclopentyl or cyclohexyl fused to another cyclopentyl or cyclohexyl to give a 5,5-, 5,6-, or 6,6-fused bicyclic carbocyclic group, which is bonded through a $C_1$–$C_8$ alkylenyl, as defined above, wherein the bicycloalkyl optionally contains 1 carbon-carbon double bond.

The phrase "Substituted $C_8$–$C_{10}$ bicycloalkyl-($C_1$–$C_8$ alkylenyl)" means a $C_8$–$C_{10}$ bicycloalkyl, as defined above, substituted with from 1 to 4 substituents, as defined above, bonded through a $C_1$–$C_8$ alkylenyl, as defined above.

The phrase "5- or 6-membered heterocycloalkyl-($C_1$–$C_8$ alkylenyl)" means a 5- or 6-membered ring containing carbon atoms and 1 or 2 heteroatoms selected from 2 O, 1 S, 1 N, 2 N(H), and 2 N($C_1$–$C_6$ alkyl), bonded through a $C_1$–$C_8$ alkylenyl, as defined above.

The phrase "Substituted 5- or 6-membered heterocycloalkyl-($C_1$–$C_6$ alkylenyl)" means a 5- or 6-membered heterocycloalkyl, as defined above, substituted with from 1 to 4 substituents, as defined above, bonded through a $C_1$–$C_8$ alkylenyl, as defined above.

The phrase "8- to 10-membered heterobicycloalkyl-($C_1$–$C_8$ alkylenyl)" means a 5- or 6-membered ring fused to another 5- or 6-membered ring to give a 5,5-, 5,6-, or 6,6-fused bicyclic group containing carbon atoms and from 1 to 4 heteroatoms independently selected from 2 O, 1 S, 1 S(O), 1 S(O)$_2$, 1 N, 4 N(H), and 4 N($C_1$–$C_6$ alkyl), bonded through a $C_1$–$C_8$ alkylenyl, as defined above, wherein the bicycloalkyl optionally contains 1 carbon-carbon double bond or 1 carbon-nitrogen double bond.

The phrase "Substituted 8- to 10-membered heterobicycloalkyl-($C_1$–$C_6$ alkylenyl)" means an 8- to 10-membered heterobicycloalkyl, as defined above, substituted with from 1 to 4 substituents, as defined above, bonded through a $C_1$–$C_8$ alkylenyl, as defined above.

The phrase "3- to 6-membered heterocycloalkyl-($C_1$–$C_8$ alkylenyl)" means a 3- to 6-membered heterocycloalkyl, as defined above, bonded through a $C_1$–$C_8$ alkylenyl, as defined above.

The phrase "Substituted 3- to 6-membered heterocycloalkyl-($C_1$–$C_8$ alkylenyl)" means a substituted 3- to 6-membered heterocycloalkyl, as defined above, bonded through a $C_1$–$C_8$ alkylenyl, as defined above.

The phrase "Phenyl-($C_1$–$C_8$ alkylenyl)" means a phenyl group bonded through a $C_1$–$C_8$ alkylenyl diradical, wherein $C_1$–$C_8$ alkylenyl is as defined above. Illustrative examples of phenyl-($C_1$–$C_8$ alkylenyl) include benzyl, 2-phenylethyl, 1-phenyl-prop-1-yl, and 3-phenyl-heptyl.

The phrase "Substituted phenyl-($C_1$–$C_8$ alkylenyl)" means a phenyl-($C_1$–$C_8$ alkylenyl) as defined above, which is substituted on phenyl and/or $C_1$–$C_8$ alkylenyl with from 1 to 4 substituents independently selected from the list above. Illustrative examples of substituted phenyl-($C_1$–$C_8$ alkylenyl) include 4-fluoro-phenylmethyl, 2-(4-Carboxy-phenyl)-ethyl, 1-(2,4-dimethoxy-phenyl)-2-oxo-propyl, and 1-phenyl-5,5-difluoro-oct-3-yl.

The term "naphthyl" includes 1-naphthyl and 2-napthyl.

The phrase "Naphthyl-($C_1$–$C_8$ alkylenyl)" means a naphthyl group as defined above bonded through a $C_1$–$C_8$ alkylenyl diradical, wherein $C_1$–$C_8$ alkylenyl is as defined above. Illustrative examples of naphthyl-($C_1$–$C_8$ alkylenyl) include naphth-1-ylmethyl, 2-(napth-1-yl)ethyl, and 3-(naphth-2-yl)-1-heptyl.

The phrase "Substituted naphthyl-($C_1$–$C_8$ alkylenyl)" means a naphthyl-($C_1$–$C_8$ alkylenyl) as defined above, which is substituted on naphthyl and/or $C_1$–$C_8$ alkylenyl with from 1 to 4 substituents independently selected from the list above. Illustrative examples of substituted phenyl-($C_1$–$C_8$ alkylenyl) include 4-fluoro-(naphth-1-yl)methyl, 2-(4-Carboxy-(naphth-1-yl))-ethyl, 1-(2,4-dimethoxy-(naphth-1-yl))-2-oxo-propyl, and 1-(naphth-2-yl)-5,5-difluorohept-2-yl.

The phrase "5- or 6-membered heteroaryl" means a 5-membered, monocyclic heteroaryl having carbon atoms and from 1 to 4 heteroatoms independently selected from 2 O, 1 S, 1 N(H), 1 N($C_1$–$C_6$ alkyl), and 4 N, or a 6-membered, monocyclic heteroaryl having carbon atoms and 1 or 2 heteroatoms selected from 2 N, and wherein:

(i) The phrase "5-membered, monocyclic heteroaryl" means a 5-membered, monocyclic, aromatic ring group as defined above having carbon atoms and from 1 to 4 heteroatoms selected from 2 O, 1 S, 1 N(H), 1 N($C_1$–$C_6$ alkyl), and 4 N. Illustrative examples of a 5-membered, monocyclic heteroaryl include thiophen-2-yl, furan-2-yl, pyrrol-3-yl, pyrrol-1-yl, imidazol-4-yl, isoxazol-3-yl, oxazol-2-yl, thiazol-4-yl, tetrazol-1-yl, 1,2,4-oxadiazol-3-yl, 1,2,4-triazol-1-yl, and pyrazol-3-yl; and (ii) The phrase "6-membered, monocyclic heteroaryl" means a 6-membered, monocyclic, aromatic ring group as defined above having carbon atoms and 1 or 2 N. Illustrative examples of a 6-membered, monocyclic heteroaryl include pyridin-2-yl, pyridin-4-yl, pyrimidin-2-yl, pyridazin-4-yl, and pyrazin-2-yl.

The phrase "8- to 10-membered heterobiaryl" means an 8-membered, 5,5-fused bicyclic heteroaryl, a 9-membered, 6,5-fused bicyclic heteroaryl, or a 10-membered, 6,6-fused bicyclic heteroaryl, having carbon atoms and from 1 to 4 heteroatoms independently selected from 2 O, 1 S, 1 N(H), 1 N($C_1$–$C_6$ alkyl), and 4 N, wherein at least one of the 2 fused rings is aromatic, and wherein when the O and S atoms both are present, the O and S atoms are not bonded to each other, which are as defined below:

(i) The phrase "8-membered, 5,5-fused bicyclic heteroaryl" means a an 8-membered aromatic, fused-bicyclic ring group as defined above having carbon atoms and from 1 to 4 heteroatoms selected from 2 O, 1 S, 1 N(H), 1 N($C_1$–$C_6$ alkyl), and 4 N. Illustrative examples of an 8-membered, fused-bicyclic heteroaryl include

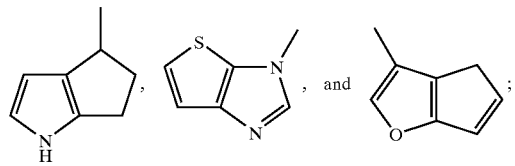

(ii) The phrase "9-membered, 6,5-fused bicyclic heteroaryl" means a 9-membered aromatic, fused-bicyclic ring group as defined above having carbon atoms and from 1 to 4 heteroatoms selected from 2 O, 1 S, 1 N(H), 1 N($C_1$–$C_6$ alkyl), and 4 N. Illustrative examples of a 9-membered, fused-bicyclic heteroaryl include indol-2-yl, indol-6-yl, iso-indol-2-yl, benzimidazol-2-yl, benzimidazol-1-yl, benztriazol-1-yl, benztriazol-5-yl, benzoxazol-2-yl, benzothiophen-5-yl, and benzofuran-3-yl; and (iii) The phrase "10-membered, 6,5-fused bicyclic heteroaryl" means a 10-membered aromatic, fused-bicyclic ring group as defined above having carbon atoms and from 1 to 4 heteroatoms selected from 2 O, 1 S, 1 N(H), 1 N($C_1$–$C_6$ alkyl), and 4 N. Illustrative examples of a 10-membered, fused-bicyclic heteroaryl include quinolin-2-yl, isoquinolin-7-yl, and benzopyrimidin-2-yl.

The phrases "substituted 5- or 6-membered heteroaryl" and "substituted 8- to 10-membered heterobiaryl" means a 5- or 6-membered heteroaryl, as defined above, or an 8- to 10-membered heterobiaryl, as defined above, respectively, which is substituted on a carbon (CH) atom, and/or nitrogen [N(H)] atom in the case of 5-, 8- to 10-membered heterobiaryl, with from 1 to 4 substituents independently selected from the list above.

Illustrative examples of substituted 5-membered, monocyclic heteroaryl groups include 2-hydroxy-oxoazol-4-yl, 5-Chloro-thiophen-2-yl, 1-methylimidazol-5-yl, 1-propyl-pyrrol-2-yl, 1-acetyl-pyrazol-4-yl, 1-methyl-1,2,4-triazol-3-yl, and 2-hexyl-tetrazol-5-yl.

Illustrative examples of substituted 6-membered, monocyclic heteroaryl groups include 4-acetyl-pyridin-2-yl, 3-fluoro-pyridin-4-yl, 5-Carboxy-pyrimidin-2-yl, 6-tertiary butyl-pyridazin-4-yl, and 5-hdyroxymethyl-pyrazin-2-yl.

Illustrative examples of substituted 8-membered, 5,5-fused bicyclic heteroaryl include:

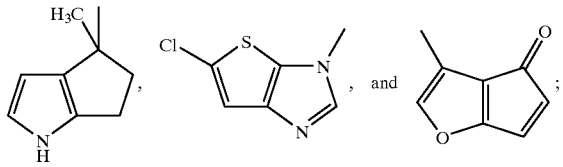

Illustrative examples of substituted 9-membered, 5,6-fused bicyclic heteroaryl include 3-(2-aminomethyl)-indol-2-yl, 2-Carboxy-indol-6-yl, 1-(methanesulfonyl)-iso-indol-2-yl, 5-trifluorometyl-6,7-difluoro-4-hydroxymethyl-benzimidazol-2-yl, 4-(3-methylureido)-2-Cyano-benzimidazol-1-yl, 1-methylbenzimidazol-6-yl, 1-acetylbenztriazol-7-yl, 1-methanesulfonyl-indol-3-yl, 1-Cyano-6-aza-indol-5-yl, and 1-(2,6-dichlorophenylmethyl)-benzpyrazol-3-yl.

Illustrative examples of substituted 10-membered, 6,6-fused bicyclic heteroaryl include 5,7-dichloro-quinolin-2-yl, isoquinolin-7-yl-1-Carboxylic acid ethyl ester, and 3-bromo-benzopyrimidin-2-yl.

The phrase "5- or 6-membered heteroaryl-($C_1$–$C_8$ alkylenyl)" means a 5- or 6-membered heteroaryl, as defined above, bonded through a $C_1$–$C_8$ alkylenyl, as defined above.

The phrase "Substituted 5- or 6-membered heteroaryl-($C_1$–$C_8$ alkylenyl)" means a 5- or 6-membered heteroaryl-($C_1$–$C_8$ alkylenyl), as defined above, which is substituted on 5- or 6-membered heteroaryl and/or $C_1$–$C_8$ alkylenyl with from 1 to 4 substituents independently selected from the list above.

Illustrative examples of substituted 5-membered heteroaryl-($C_1$–$C_8$ alkylenyl) groups include 2-hydroxy-oxoazol-4-ylmethyl, 4-(5-Chloro-thiophen-2-yl)-hex-1-yl, and 2-tetrazol-5-yloctyl.

Illustrative examples of substituted 6-membered heteroaryl-($C_1$–$C_8$ alkylenyl) groups include 4-acetyl-pyridin-2-ylmethyl, 7-(3-fluoro-pyridin-4-yl)-hept-2-yl, and 2-(5-hdyroxymethyl-pyrazin-2-yl)-1,1-difluoro-2-hydroxy-prop-2-yl.

The phrase "8- to 10-membered heterobiaryl-($C_1$–$C_8$ alkylenyl)" means an 8- to 10-membered heterobiaryl, as defined above, bonded through a $C_1$–$C_8$ alkylenyl, as defined above.

The phrase "Substituted 8- to 10-membered heterobiaryl-($C_1$–$C_8$ alkylenyl)" means an 8- to 10-membered heterobiaryl-($C_1$–$C_8$ alkylenyl), as defined above, which is substituted on 8- to 10-membered heterobiaryl and/or $C_1$–$C_8$ alkylenyl with from 1 to 4 substituents independently selected from the list above.

Illustrative examples of substituted 8-membered heterobiaryl-($C_1$–$C_8$ alkylenyl) include:

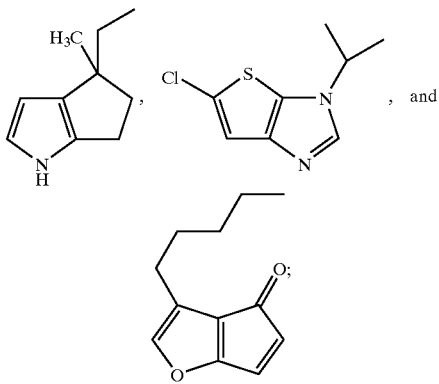

Illustrative examples of substituted 9-membered heterobiaryl-($C_1$–$C_8$ alkylenyl) include 3-(2-aminomethyl)-indol-2-ylmethyl, and 1-(1-(2,6-dichlorophenylmethyl)-benzpyrazol-3-yl)-prop3-yl.

Illustrative examples of substituted 10-membered heterobiaryl-($C_1$–$C_8$ alkylenyl) include 5,7-dichloroquinolin-2-ylmethyl, and 5-(3-bromo-benzopyrimidin-2-yl)-oct-2-yl.

The phrase "($C_1$–$C_6$ alkyl)-O" means a $C_1$–$C_6$ alkyl group, as defined above, bonded through an oxygen atom.

The phrase "($C_1$–$C_6$ alkyl)-S" means a $C_1$–$C_6$ alkyl group, as defined above, bonded through an sulfur atom.

The phrase "($C_1$–$C_6$ alkyl)-S(O)$_2$" means a $C_1$–$C_6$ alkyl group, as defined above, bonded through a sulfur atom, which sulfur atom is substituted with two oxygen atoms.

The phrase "($C_1$–$C_6$ alkyl)-N(H)" means a $C_1$–$C_6$ alkyl group, as defined above, bonded through a nitrogen atom, which is bonded to a hydrogen atom.

The phrase "($C_1$–$C_6$ alkyl)$_2$-N" means two independently selected $C_1$–$C_6$ alkyl groups, as defined above, including cyclic groups wherein the two $C_1$–$C_6$ alkyl groups are taken together with the nitrogen atom to which they are both bonded to form a 5- or 6-membered heterocycloalkyl, bonded through a nitrogen atom.

The phrase "($C_1$–$C_6$ alkyl)-OC(O)" means a $C_1$–$C_6$ alkyl, as defined above, bonded through an oxygen atom-carbonyl carbon atom.

The phase "($C_1$–$C_6$ alkyl)-C(O)O-($C_1$–$C_8$ alkylenyl)$_m$", wherein m is an integer of 0 or 1, means when, m is 0, a $C_1$–$C_6$ alkyl group, as defined above, bonded through a carbonyl carbon atom-oxygen atom, and, when m is 1, a $C_1$–$C_6$ alkyl group, as defined above, bonded through a carbonyl carbon atom-oxygen atom-($C_1$–$C_8$ alkylenyl), wherein $C_1$–$C_8$ alkylenyl is as defined above.

The phase "($C_1$–$C_6$ alkyl)-C(O)O-(1- to 8-membered heteroalkylenyl)$_m$", wherein m is an integer of 0 or 1, means, when m is 0, a $C_1$–$C_6$ alkyl group, as defined above, bonded through a carbonyl carbon atom-oxygen atom, and, when m is 1, a $C_1$–$C_6$ alkyl group, as defined above, bonded through a carbonyl carbon atom-oxygen atom-(1- to 8-membered heteroalkylenyl), wherein 1- to 8-membered heteroalkylenyl is as defined above.

The phase "($C_1$–$C_6$ alkyl)-C(O)N(H)-($C_1$–$C_8$ alkylenyl)$_m$", wherein m is an integer of 0 or 1, means, when m is 0, a $C_1$–$C_6$ alkyl group, as defined above, bonded through a carbonyl carbon atom-nitrogen atom, which is bonded to a hydrogen atom, and, when m is 1, a $C_1$–$C_6$ alkyl group, as defined above, bonded through a carbonyl carbon atom-nitrogen atom-($C_1$–$C_8$ alkylenyl), wherein $C_1$–$C_8$ alkylenyl is as defined above and the nitrogen atom is bonded to a hydrogen atom.

The phase "($C_1$–$C_6$ alkyl)-C(O)N(H)-(1- to 8-membered heteroalkylenyl)$_m$", wherein m is an integer of 0 or 1, means when, m is 0, a $C_1$–$C_6$ alkyl group, as defined above, bonded through a carbonyl carbon atom-nitrogen atom, which is bonded to a hydrogen atom, and, when m is 1, a $C_1$–$C_6$ alkyl group, as defined above, bonded through a carbonyl carbon atom-nitrogen atom-(1- to 8-membered heteroalkylenyl), wherein 1- to 8-membered heteroalkylenyl is as defined above and the nitrogen atom is bonded to a hydrogen atom.

The phrase "$H_2NS(O)_2$—($C_1$–$C_8$ alkylenyl)" means an amino bonded through a sulfur atom-($C_1$–$C_8$ alkylenyl), wherein the $C_1$–$C_8$ alkylenyl is as defined above and the sulfur atom is bonded to two oxygen atoms.

The phrase "($C_1$–$C_6$ alkyl)-N(H)S(O)$_2$—($C_1$–$C_8$ alkylenyl)$_m$", wherein m is an integer of 0 or 1, means, when m is 0, a $C_1$–$C_6$ alkyl, as defined above, bonded through a nitrogen atom-sulfur atom, and, when m is 1, a $C_1$–$C_6$ alkyl, as defined above, bonded through a nitrogen atom-sulfur atom-($C_1$–$C_8$ alkylenyl), wherein the nitrogen atom is bonded to a hydrogen atom, the sulfur atom is bonded to two oxygen atoms, and $C_1$–$C_8$ alkylenyl is as defined above.

The phrase "($C_1$–$C_6$ alkyl)$_2$—NS(O)$_2$—($C_1$–$C_8$ alkylenyl)$_m$", wherein m is an integer of 0 or 1, means, when m is 0, two $C_1$–$C_6$ alkyl groups, as defined above, including cyclic groups wherein the two $C_1$–$C_6$ alkyl groups are taken together with the nitrogen atom to which they are both bonded to form a 5- or 6-membered heterocycloalkyl, each bonded through a nitrogen atom-sulfur atom, and, when m is 1, two $C_1$–$C_6$ alkyl groups, as defined above, each bonded through a nitrogen atom-sulfur atom-($C_1$–$C_8$ alkylenyl), wherein the nitrogen atom is bonded to a hydrogen atom, the sulfur atom is bonded to two oxygen atoms, and $C_1$–$C_8$ alkylenyl is as defined above.

The phrase "3- to 6-membered heterocycloalkyl-(G)$_m$", wherein m is an integer of 0 or 1, means, when m is 0, a 3- to 6-membered heterocycloalkyl, as defined above, and, when m is 1, a 3- to 6-membered heterocycloalkyl, as defined above, bonded through a group G, as defined above.

The phrase "Substituted 3- to 6-membered heterocycloalkyl-(G)$_m$", wherein m is an integer of 0 or 1, means, when m is 0, a substituted 3- to 6-membered heterocycloalkyl, as defined above, and, when m is 1, a substituted 3- to 6-membered heterocycloalkyl, as defined above, bonded through a group G, as defined above.

The phrase "5- or 6-membered heteroaryl-(G)$_m$", wherein m is an integer of 0 or 1, means, when m is 0, a 5- or 6-membered heteroaryl, as defined above, and, when m is 1, a 5- or 6-membered heteroaryl, as defined above, bonded through a group G, as defined above.

The phrase "Substituted 5- or 6-membered heteroaryl-(G)$_m$", wherein m is an integer of 0 or 1, means, when m is 0, a substituted 5- or 6-membered heteroaryl, as defined above, and, when m is 1, a substituted 5- or 6-membered heteroaryl, as defined above, bonded through a group G, as defined above.

The term "Phenyl-O—(C$_1$-C$_8$ alkylenyl)" means a phenyl bonded through an oxygen atom, which is bonded through a C$_1$-C$_8$ alkylenyl, wherein C$_1$-C$_8$ alkylenyl is as defined above. Illustrative examples of phenyl-O—(C$_1$-C$_8$ alkylenyl) include phenoxymethyl and 2-phenoxyethyl.

The term "Substituted phenyl-O—(C$_1$-C$_8$ alkylenyl)" means a phenyl-O—(C$_1$-C$_8$ alkylenyl) group, as defined above, that is substituted with from 1 to 4 substituents as defined above for R$^2$. Illustrative examples of substituted phenyl-O—(C$_1$-C$_8$ alkylenyl) include 4-fluorophenoxymethyl and 2-phenoxy-methylcarbonyl.

The term "Phenyl-S—(C$_1$-C$_8$ alkylenyl)" means a phenyl bonded through an sulfur atom, which is bonded through a C$_1$-C$_8$ alkylenyl, wherein C$_1$-C$_8$ alkylenyl is as defined above. Illustrative examples of phenyl-S—(C$_1$-C$_8$ alkylenyl) include thiophenoxymethyl and 2-thiophenoxyethyl.

The term "Substituted phenyl-S—(C$_1$-C$_8$ alkylenyl)" means a phenyl-S—(C$_1$-C$_8$ alkylenyl) group, as defined above, that is substituted with from 1 to 4 substituents as defined above for R$^2$. Illustrative examples of substituted phenyl-S—(C$_1$-C$_8$ alkylenyl) include 4-fluorothiophenoxymethyl and 2-thiophenoxy-methylcarbonyl.

The term "Phenyl-S(O)-(C$_1$-C$_8$ alkylenyl)" means a phenyl bonded through an sulfur atom, which is bonded through a C$_1$-C$_8$ alkylenyl, wherein C$_1$-C$_8$ alkylenyl is as defined above and the sulfur atom is also bonded to an oxygen atom. Illustrative examples of phenyl-S(O)-(C$_1$-C$_8$ alkylenyl) include phenyl-S(=O)—CH$_2$ and phenyl-S(=O)—CH$_2$CH$_2$.

The term "Substituted phenyl-S(O)-(C$_1$-C$_8$ alkylenyl)" means a phenyl-S(O)-(C$_1$-C$_8$ alkylenyl) group, as defined above, that is substituted with from 1 to 4 substituents as defined above for R . Illustrative examples of substituted phenyl-S(O)-(C$_1$-C$_8$ alkylenyl) include (4-Fluoro-phenyl)-S(=O)—CH$_2$ and phenyl-S(=O)—CH$_2$C(=O).

The term "Phenyl-S(O)$_2$—(C$_1$-C$_8$ alkylenyl)" means a phenyl bonded through an sulfur atom, which is bonded through a C$_1$-C$_8$ alkylenyl, wherein C$_1$-C$_8$ alkylenyl is as defined above and the sulfur atom is also bonded to two oxygen atoms. Illustrative examples of phenyl-S(O)$_2$—(C$_1$-C$_8$ alkylenyl) include phenyl-S(=O)$_2$—CH$_2$ and phenyl-S(=O)$_2$—CH$_2$CH$_2$.

The term "Substituted phenyl-S(O)$_2$—(C$_1$-C$_8$ alkylenyl)" means a phenyl-S(O)$_2$—(C$_1$-C$_8$ alkylenyl) group, as defined above, that is substituted with from 1 to 4 substituents as defined above for R$^2$. Illustrative examples of substituted phenyl-S(O)$_2$—(C$_1$-C$_8$ alkylenyl) include (4-Fluoro-phenyl)-S(=O)$_2$—CH$_2$ and phenyl-S(=O)$_2$—CH$_2$C(=O).

The term "(C$_1$-C$_6$ alkyl)-S(O)$_2$—N(H)—C(O)-(C$_1$-C$_8$ alkylenyl)$_m$", wherein m is an integer of 0 or 1, means, when m is 0, a C$_1$-C$_6$ alkyl group, as defined above, bonded through a sulfur atom, which is bonded through a nitrogen atom, which is bonded through a carbon atom, wherein the sulfur atom is bonded to two oxygen atoms, the nitrogen atom is bonded to a hydrogen atom, and the carbon atom is doubly bonded to an oxygen atom to form a carbonyl group; and when m is 1, the term means a C$_1$-C$_6$ alkyl group, as defined above, bonded through a sulfur atom, which is bonded through a nitrogen atom, which is bonded through a carbon atom, which is bonded through a C$_1$-C$_8$ alkylenyl group, as defined above, wherein the sulfur atom is bonded to two oxygen atoms, the nitrogen atom is bonded to a hydrogen atom, and the carbon atom is doubly bonded to an oxygen atom to form a carbonyl group. Illustrative examples of (C$_1$-C$_6$ alkyl)-S(=O)$_2$—N(H)—C(O)—(C$_1$-C$_8$ alkylenyl)$_m$ include CH$_3$—S(O)$_2$—N(H)—C(=O) and CH$_3$—S(O)$_2$—N(H)—C(=O)—CH$_2$.

The term "(C$_1$-C$_6$ alkyl)—C(O)—N(H)—S(O)$_2$—(C$_1$-C$_8$ alkylenyl)$_m$", wherein m is an integer of 0 or 1, means, when m is 0, a C$_1$-C$_6$ alkyl group, as defined above, bonded through a carbon atom, which is bonded through a nitrogen atom, which is bonded through a sulfur atom, wherein the sulfur atom is bonded to two oxygen atoms, the nitrogen atom is bonded to a hydrogen atom, and the carbon atom is doubly bonded to an oxygen atom to form a carbonyl group; and when m is 1, the term means a C$_1$-C$_6$ alkyl group, as defined above, bonded through a carbon atom, which is bonded through a nitrogen atom, which is bonded through a sulfur atom, which is bonded through a C$_1$-C$_8$ alkylenyl group, as defined above, wherein the sulfur atom is bonded to two oxygen atoms, the nitrogen atom is bonded to a hydrogen atom, and the carbon atom is doubly bonded to an oxygen atom to form a carbonyl group. Illustrative examples of (C$_1$-C$_6$ alkyl)—C(O)—N(H)—S(O)$_2$—(C$_1$-C$_8$ alkylenyl)$_m$ include CH$_3$—C(=O)—N(H)—S(=O)$_2$ and CH$_3$—C(=O)—N(H)—S(=O)$_2$—CH$_2$.

Preferred substituents for substituted phenyl, substituted naphthyl (i.e., substituted 1-naphthyl or substituted 2-naphthyl), and preferred substituents at carbon atoms for substituted 5-membered, monocyclic heteroaryl, substituted 6-membered, monocyclic heteroaryl, and substituted 9- or 10-membered, fused-bicyclic heteroaryl are C$_1$-C$_4$ alkyl, halo, OH, O—C$_1$-C$_4$ alkyl, 1,2-methylenedioxy, oxo ("=O"), CN, NO$_2$, N$_3$, NH$_2$, N(H)CH$_3$, N(CH$_3$)$_2$, C(O)CH$_3$, OC(O)—C$_1$-C$_4$ alkyl, C(O)—H, CO$_2$H, CO$_2$—(C$_1$-C$_4$ alkyl), C(O)—N(H)OH, C(O)NH$_2$, C(O)NHMe, C(O)N(Me)$_2$, NHC(O)CH$_3$, N(H)C(O)NH$_2$, SH, S—C$_1$-C$_4$ alkyl, C≡CH, C(=NOH)—H, C(=NOH)—CH$_3$, CH$_2$OH, CH$_2$NH$_2$, CH$_2$N(H)CH$_3$, CH$_2$N(CH$_3$)$_2$, C(H)F—OH, CF$_2$—OH, S(O)$_2$NH2, S(O)$_2$N(H)CH$_3$, S(O)$_2$N(CH$_3$)$_2$, S(O)—CH$_3$, S(O)$_2$CH$_3$, S(O)$_2$CF$_3$, or NHS(O)$_2$CH$_3$.

Especially preferred substituents are 1,2-methylenedioxy, methoxy, ethoxy, —O—C(O)CH$_3$, carboxy, carbomethoxy, and carboethoxy.

The term "1,2-methylenedioxy" means the diradical group —O—CH$_2$—O—, wherein the substituent 1,2-methylenedioxy is bonded to adjacent carbon atoms of the group which is substituted to form a 5-membered ring. Illustrative examples of groups substituted by 1,2-methylenedioxy include 1,3-benzoxazol-5-yl of formula

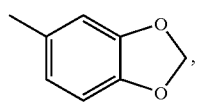

which is a phenyl group substituted by 1,2-methylenedioxy.

A fused-bicyclic group is a group wherein two ring systems share two, and only two, atoms.

It should be appreciated that the groups heteroaryl or heterocycloalkyl may not contain two ring atoms bonded to each other which atoms are oxygen and/or sulfur atoms.

The term "oxo" means =O. Oxo is attached at a carbon atom unless otherwise noted. Oxo, together with the carbon atom to which it is attached forms a carbonyl group (i.e., C=O).

The term "heteroatom" includes O, S, S(O), S(O)$_2$, N, N(H), and N(C$_1$–C$_6$ alkyl).

The term "halo" includes fluoro, chloro, bromo, and iodo.

The term "amino" means NH$_2$.

The phrase "two adjacent, substantially sp$^2$ carbon atoms" means carbon atoms that comprise a carbon-carbon double bond that is capable of being substituted on each carbon atom, wherein the carbon-carbon double bond is contained in an aromatic or nonaromatic, cyclic or acyclic, or carbocyclic or heterocyclic group.

The phrase "tertiary organic amine" means a trisubstituted nitrogen group wherein the 3 substituents are independently selected from C$_1$–C$_{12}$ alkyl, C$_3$–C$_{12}$ cycloalkyl, benzyl, or wherein two of the substituents are taken together with the nitrogen atom to which they are bonded to form a 5- or 6-membered, monocyclic heterocycle containing one nitrogen atom and carbon atoms, and the third substituent is selected from C$_1$–C$_{12}$ alkyl and benzyl, or wherein the three substituents are taken together with the nitrogen atom to which they are bonded to form a 7- to 12-membered bicyclic heterocycle containing 1 or 2 nitrogen atoms and carbon atoms, and optionally a C=N double bond when 2 nitrogen atoms are present. Illustrative examples of tertiary organic amine include triethylamine, diisopropylethylamine, benzyl diethylamino, dicyclohexylmethyl-amine, 1,8-diazabicyclo[5.4.0]undec-7-ene (DBU), 1,4-diazabicyclo[2.2.2]octane (TED), and 1,5-diazabicyclo[4.3.0]non-5-ene.

The phrase "pharmaceutical composition" means a composition suitable for administration in medical or veterinary use.

The term "admixed" and the phrase "in admixture" are synonymous and mean in a state of being in a homogeneous or heterogeneous mixture. Preferred is a homogeneous mixture.

The term "patient" means a mammal. Preferred patients are humans, cats, dogs, cows, horses, pigs, and sheep.

The term "animal" means a mammal, as defined above. Preferred animals include humans, cats, dogs, horses, pigs, sheep, cows, monkeys, rats, mice, guinea pigs, and rabbits.

The term "mammal" includes humans, companion animals such as cats and dogs, primates such as monkeys and chimpanzees, and livestock animals such as horses, cows, pigs, and sheep.

The phrase "livestock animals" as used herein refers to domesticated quadrupeds, which includes those being raised for meat and various byproducts, e.g., a bovine animal including cattle and other members of the genus *Bos,* a porcine animal including domestic swine and other members of the genus *Sus,* an ovine animal including sheep and other members of the genus *Ovis,* domestic goats and other members of the genus *Capra;* domesticated quadrupeds being raised for specialized tasks such as use as a beast of burden, e.g., an equine animal including domestic horses and other members of the family Equidae, genus *Equus,* or for searching and sentinel duty, e.g., a canine animal including domestic dogs and other members of the genus *Canis;* and domesticated quadrupeds being raised primarily for recreational purposes, e.g., members of *Equus* and *Canis,* as well as a feline animal including domestic cats and other members of the family Felidae, genus *Felis.*

The phrase "anticancer effective amount" means an amount of invention compound, or a pharmaceutically acceptable salt thereof, or a tautomer thereof, sufficient to inhibit, halt, or cause regression of the cancer being treated in a particular patient or patient population. For example in humans or other mammals, an anticancer effective amount can be determined experimentally in a laboratory or clinical setting, or may be the amount required by the guidelines of the United States Food and Drug Administration, or equivalent foreign agency, for the particular cancer and patient being treated.

The phrase "anti-arthritic effective amount" means an amount of invention compound, or a pharmaceutically acceptable salt thereof, or a tautomer thereof, sufficient to inhibit, halt, or cause regression of the arthritis being treated in a particular patient or patient population. For example in humans or other mammals, an anti-arthritic effective amount can be determined experimentally in a laboratory or clinical setting, or may be the amount required by the guidelines of the United States Food and Drug Administration, or equivalent foreign agency, for the particular arthritis and patient being treated.

The phrase "MMP-13 inhibiting amount" means an amount of invention compound, or a pharmaceutically acceptable salt thereof, or a tautomer thereof, sufficient to inhibit an enzyme matrix metalloproteinase-13, including a truncated form thereof, including a catalytic domain thereof, in a particular animal or animal population. For example in a human or other mammal, an MMP-13 inhibiting amount can be determined experimentally in a laboratory or clinical setting, or may be the amount required by the guidelines of the United States Food and Drug Administration, or equivalent foreign agency, for the particular MMP-13 enzyme and patient being treated.

It should be appreciated that determination of proper dosage forms, dosage amounts, and routes of administration, is within the level of ordinary skill in the pharmaceutical and medical arts, and is described below.

The phrases "effective amount" and "therapeutically effective amount" are synonymous and mean an amount of a compound of the present invention, a pharmaceutically acceptable salt thereof, or a solvate thereof, sufficient to effect an improvement of the condition being treated when administered to a patient suffering from a disease that is mediated by MMP-13 and optionally from 0 to 12 additional MMP enzymes.

The term "tautomer" means a form of invention compound existing in a state of equilibrium with an isomeric form of the invention compound, wherein the invention compound is able to react according to either form by virtue of the ability of the forms to interconvert by isomerization in situ, including in a reaction mixture, in an in vitro biological assay, or in vivo.

The term "(E)" means entgegen, and designates that the conformation about the double bond to which the term refers is the conformation having the two higher ranking substituent groups, as determined according to the Cahn-Ingoid-Prelog ranking system, on opposite sides of the double bond.

An (E) double bond is illustrated below by the compound of Formula (W)

(W)

wherein the two higher-ranking substituents are groups A and D.

The term "(Z)" means zusammen, and designates that the conformation about the double bond to which the term refers is the conformation having the two higher ranking substituent groups, as determined according to the Cahn-Ingold-Prelog ranking system, on the same side of the double bond. A (Z) double bond is illustrated below by the compound of Formula (X)

(X)

wherein the two higher-ranking substituents are groups A and D.

It should be appreciated that the S1' site of MMP-13 was previously thought to be a grossly linear channel which contained an opening at the top that allowed an amino acid side chain from a substrate molecule to enter during binding, and was closed at the bottom. Applicants has discovered that the S1' site is actually composed of an S1' channel angularly connected to a newly discovered pocket which applicant calls the S1" site. The S1" site is open to solvent at the bottom, which can expose a functional group of Applicants' invention compounds to solvent. For illustrative purposes, the S1' site of the MMP-13 enzyme can now be thought of as being like a sock with a hole in the toes, wherein the S1' channel is the region from approximately the opening to the ankle, and the S1" site is the foot region below the ankle, which foot region is angularly connected to the ankle region.

More particularly, the S1' channel is a specific part of the S1' site and is formed largely by Leu218, Val219, His222 and by residues from Leu239 to Tyr244. The S1" binding site which has been newly discovered is defined by residues from Tyr246 to Pro255. The S1" site contains at least two hydrogen bond donors and aromatic groups which interact with an invention compound.

Without wishing to be bound by any particular theory, the inventors believe that the S1" site could be a recognition site for triple helix collagen, the natural substrate for MMP-13. It is possible that the conformation of the S1" site is modified only when an appropriate compound binds to MMP-13, thereby interfering with the collagen recognition process. This newly discovered pattern of binding offers the possibility of greater selectivity than what is achievable with the binding pattern of known selective inhibitors of MMP-13, wherein the known binding pattern requires ligation of the catalytic zinc atom at the active site and occupation the S1' channel, but not the S1" site. The term "Thr245" means threonine 245 of an MMP-13 enzyme.

The term "Thr247" means threonine 247 of an MMP-13 enzyme.

The term "Met253" means methionine 253 of an MMP-13 enzyme.

The term "His251" means histidine 251 of an MMP-13 enzyme.

It should be appreciated that the matrix metalloproteinases include, but are not limited to, the following enzymes:

MMP-1, also known as interstitial collagenase, collagenase-1, or fibroblast-type collagenase;

MMP-2, also known as gelatinase A or 72 kDa Type IV collagenase;

MMP-3, also known as stromelysin or stromelysin-1;

MMP-7, also known as matrilysin or PUMP-1;

MMP-8, also known as collagenase-2, neutrophil collagenase or polymorphonuclear-type ("PMN-type") collagenase;

M-9, also known as gelatinase B or 92 kDa Type IV collagenase;

MMP-10, also known as stromelysin-2;

MMP-11, also known as stromelysin-3;

MMP-12, also known as metalloelastase;

MMP-13, also known as collagenase-3;

MMP-14, also known as membrane-type ("MT") 1-MMP or MT1-MMP;

MMP-15, also known as MT2-MMP;

MMP-16, also known as MT3-MMP;

MMP-17, also known as MT4-MMP;

MMP-18; and

MMP-19.

Other known MMPs include MMP-26 (Matrilysin-2).

For the purposes of this invention, the term "arthritis", which is synonymous with the phrase "arthritic condition", includes osteoarthritis, rheumatoid arthritis, degenerative joint disease, spondyloarthropathies, gouty arthritis, systemic lupus erythematosus, juvenile arthritis, and psoriatic arthritis. An allosteric compound inhibitor of MMP-13 having an anti-arthritic effect is a compound as defined above that inhibits the progress, prevents further progress, or reverses progression, in part or in whole, of any one or more symptoms of any one of the arthritic diseases and disorders listed above.

The term "$IC_{50}$" means the concentration of a compound, usually expressed as micromolar or nanomolar, required to inhibit an enzyme's catalytic activity by 50%.

The term "$ED_{40}$" means the concentration of a compound, usually expressed as micromolar or nanomolar, required to treat a disease in about 40% of a patient group.

The term "$ED_{30}$" means the concentration of a compound, usually expressed as micromolar or nanomolar, required to treat a disease in 30% of a patient group.

The phrase "pharmaceutical composition" means a composition suitable for administration in medical or veterinary use.

The term "admixed" and the phrase "in admixture" are synonymous and mean in a state of being in a homogeneous or heterogeneous mixture. Preferred is a homogeneous mixture.

As used herein, the phrase "cartilage damage" means a disorder of hyaline cartilage and subchondral bone characterized by hypertrophy of tissues in and around the involved joints, which may or may not be accompanied by deterioration of hyaline cartilage surface.

The phrase "treating", which is related to the terms "treat" and "treated", means administration of an invention combination as defined above that inhibits the progress, prevents further progress, or reverses progression, in part or in whole, of any one or more symptoms of any one of the diseases and disorders listed above.

The phrase "invention compound" means a compound of Formula I, or a pharmaceutically acceptable salt thereof, as fully defined above.

The term "nontoxic" means the efficacious dose is 10 times or greater than the dose at which a toxic effect is observed in 10% or more of a patient population.

The term "celecoxib" means the compound named 4-(5-(4-methylphenyl)-3-(trifluoromethyl)-1H-pyrazol-1-yl)-benzenesulfonamide. Celecoxib is a selective cyclooxygenase-2 ("COX-2") inhibitor currently approved by the FDA for the treatment of osteoarthritis, rheumatoid arthritis, and Polyposis-familial adenomatus. Celecoxib is marketed under the tradename "Celebrex". Celecoxib is currently in clinical trials for the treatment of bladder cancer, chemopreventative-lung cancer, and post-operative pain, and is registered for the treatment of dysmenorrhea. Celecoxib has the structure drawn below:

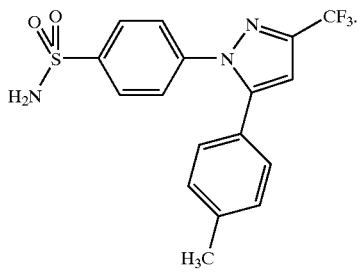

The term "valdecoxib" means the compound named 4-(5-methyl-3-phenyl-4-isoxazolyl)-benzenesulfonamide. Valdecoxib is a selective COX-2 inhibitor that has been approved by the FDA for treating osteoarthritis, rheumatoid arthritis, dysmenorrhea, and general pain, and is marketed under the tradename "Bextra". Valdecoxib is in clinical trials for the treatment of migraine. Valdecoxib has the structure drawn below:

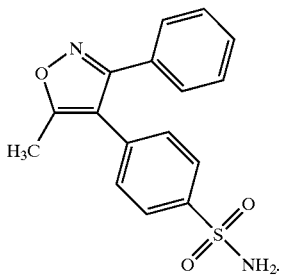

It should be appreciated that COX-2 is also known as prostaglandin synthase-2 and prostaglandin $PGH_2$ synthase.

A selective inhibitor of COX-2 means compounds that inhibit COX-2 selectively versus COX-1 such that a ratio of $IC_{50}$ for a compound with COX-1 divided by a ratio of $IC_{50}$ for the compound with COX-2 is greater than, or equal to, 5, where the ratios are determined in one or more assays. All that is required to determine whether a compound is a selective COX-2 inhibitor is to assay a compound in one of a number of well know assays in the art.

The term "NSAID" is an acronym for the phrase "non-steroidal anti-inflammatory drug", which means any compound which inhibits cyclooxygenase-1 ("COX-1") and cyclooxygenase-2. Most NSAIDs fall within one of the following five structural classes: (1) propionic acid derivatives, such as ibuprofen, naproxen, naprosyn, diclofenac, and ketoprofen; (2) acetic acid derivatives, such as tolmetin and sulindac; (3) fenamic acid derivatives, such as mefenamic acid and meclofenamic acid; (4) biphenylcarboxylic acid derivatives, such as diflunisal and flufenisal; and (5) oxicams, such as piroxim, peroxicam, sudoxicam, and isoxicam. Other useful NSAIDs include aspirin, acetominophen, indomethacin, and phenylbutazone. Selective inhibitors of cyclooxygenase-2 as described above may be considered to be NSAIDs also.

The term "drugs", which is synonymous with the phrases "active components", "active compounds", and "active ingredients", includes celecoxib, or a pharmaceutically acceptable salt thereof, valdecoxib, or a pharmaceutically acceptable salt thereof, and an allosteric inhibitor of MMP-13, and may further include one or two of the other therapeutic agents described above.

The compounds of Formula I, or pharmaceutically acceptable salts thereof, or tautomers thereof, include compounds which are invention compounds. An allosteric inhibitor of MMP-13 is any compound of Formula I that binds allosterically into the S1' site of the MMP-13 enzyme, including the S1' channel, and a newly discovered S1" site, without ligating, coordinating, or binding the catalytic zinc of the MMP-13.

An invention compound that is an allosteric inhibitor of MMP-13 may be readily identified by one of ordinary skill in the pharmaceutical or medical arts by assaying an alkyne test compound for inhibition of MMP-13 as described below in Biological Methods 1 or 2, and for allosteric inhibition of MMP-13 by assaying the test invention compound for inhibition of MMP-13 in the presence of an inhibitor to the catalytic zinc of MMP-13 as described below in Biological Methods 3 or 4.

Further, an invention compound having an anti-inflammatory, an analgesic, anti-arthritic, or a cartilage damage inhibiting effect, or any combination of these effects, may be readily identified by one of ordinary skill in the pharmaceutical or medical arts by assaying the invention compound in any number of well known assays for measuring determining the invention compound's effects on cartilage damage, arthritis, inflammation, or pain. These assays include in vitro assays that utilize cartilage samples and in vivo assays in whole animals that measure cartilage degradation, inhibition of inflammation, or pain alleviation.

For example with regard to assaying cartilage damage in vitro, an amount of an invention compound or control vehicle may be administered with a cartilage damaging agent to cartilage, and the cartilage damage inhibiting effects in both tests studied by gross examination or histopathologic examination of the cartilage, or by measurement of biological markers of cartilage damage such as, for example, proteoglycan content or hydroxyproline content. Further, in vivo assays to assay cartilage damage may be performed as follows: an amount of an invention compound or control vehicle may be administered with a cartilage damaging agent to an animal, and the effects of the invention compound being assayed on cartilage in the animal may be evaluated by gross examination or histopathologic examination of the cartilage, by observation of the effects in an acute model on functional limitations of the affected joint that result from cartilage damage, or by measurement of biological markers of cartilage damage such as, for example, proteoglycan content or hydroxyproline content.

Several methods of identifying an invention compound with cartilage damage inhibiting properties are described below. The amount to be administered in an assay is dependent upon the particular assay employed, but in any event is not higher than the well known maximum amount of a compound that the particular assay can effectively accommodate.

Similarly, invention compounds having pain-alleviating properties may be identified using any one of a number of in vivo animal models of pain.

Still similarly, invention compounds having anti-inflammatory properties may be identified using any one of a number of in vivo animal models of inflammation. For example, for an example of inflammation models, see U.S. Pat. No. 6,329,429, which is incorporated herein by reference.

Still similarly, invention compounds having anti-arthritic properties may be identified using any one of a number of in vivo animal models of arthritis. For example, for an example of arthritis models, see also U.S. Pat. No. 6,329,429.

Other mammalian diseases and disorders which are treatable by administration of an invention combination alone, or contained in a pharmaceutical composition as defined below, include: fever (including rheumatic fever and fever associated with influenza and other viral infections), common cold, dysmenorrhea, menstrual cramps, inflammatory bowel disease, Crohn's disease, emphysema, acute respiratory distress syndrome, asthma, bronchitis, chronic obstructive pulmonary disease, Alzheimer's disease, organ transplant toxicity, cachexia, allergic reactions, allergic contact hypersensitivity, cancer (such as solid tumor cancer including colon cancer, breast cancer, lung cancer and prostrate cancer; hematopoietic malignancies including leukemias and lymphomas; Hodgkin's disease; aplastic anemia, skin cancer and familiar adenomatous polyposis), tissue ulceration, peptic ulcers, gastritis, regional enteritis, ulcerative colitis, diverticulitis, recurrent gastrointestinal lesion, gastrointestinal bleeding, coagulation, anemia, synovitis, gout, ankylosing spondylitis, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), periarteritis nodosa, congestive heart failure, myocardial infarction, stroke, cerebral ischemia, head trauma, spinal cord injury, neuralgia, neuro-degenerative disorders (acute and chronic), autoimmune disorders, Huntington's disease, Parkinson's disease, migraine, depression, peripheral neuropathy, pain (including low back and neck pain, headache and toothache), gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders (such as psoriasis, eczema, scleroderma and dermatitis), myasthenia gravis, polymyositis, myositis, bursitis, bums, diabetes (including types I and II diabetes, diabetic retinopathy, neuropathy and nephropathy), tumor invasion, tumor growth, tumor metastasis, corneal scarring, scleritis, immunodeficiency diseases (such as AIDS in humans and FLV, FIV in cats), sepsis, premature labor, hypoprothrombinemia, hemophilia, thyroiditis, sarcoidosis, Behcet's syndrome, hypersensitivity, kidney disease, Rickettsial infections (such as Lyme disease, Erlichiosis), Protozoan diseases (such as malaria, giardia, coccidia), reproductive disorders (preferably in livestock), epilepsy, convulsions, and septic shock.

Other aspects of the present invention are compounds of Formula I, or a pharmaceutically acceptable salt thereof, that are $\geq 10$, $\geq 20$, $\geq 50$, $\geq 100$, or $\geq 1000$ times more potent versus MMP-13 than versus at least two of any other MMP enzyme or TACE.

Still other aspects of the present invention are compounds of Formula I, or a pharmaceutically acceptable salt thereof, that are selective inhibitors of MMP-13 versus 2, 3, 4, 5, 6, or 7 other MMP enzymes, or versus TACE and 1, 2, 3, 4, 5, 6, or 7 other MMP enzymes.

It should be appreciated that selectivity of a compound of Formula I, or a pharmaceutically acceptable salt thereof, is a multidimensional characteristic that includes the number of other MMP enzymes and TACE over which selectivity for MMP-13 inhibition is present and the degree of selectivity of inhibition of MMP-13 over another particular MMP or TACE, as measured by, for example, the $IC_{50}$ in micromolar concentration of the compound for the inhibition of the other MMP enzyme or TACE divided by the $IC_{50}$ in micromolar concentration of the compound for the inhibition of MMP-13.

As discussed above, one aspect of the present invention is novel compounds that are selective inhibitors of the enzyme MMP-13. A selective inhibitor of MMP-13, as used in the present invention, is a compound that is $\geq 5\times$ more potent in vitro versus MMP-13 than versus at least one other matrix metalloproteinase enzyme such as, for example, MMP-1, MMP-2, MMP-3, MMP-7, MMP-8, MMP-9, or MMP-14, or versus tumor necrosis factor alpha convertase ("TACE"). A preferred aspect of the present invention is novel compounds that are selective inhibitors of MMP-13 versus MMP-1.

The invention provides a compound of Formula I, or a pharmaceutically acceptable salt thereof, which has an $IC_{50}$ with any MMP enzyme that is less than or equal to 50 micromolar. Preferred are compounds of Formula I, or a pharmaceutically acceptable salt thereof, which have an $IC_{50}$ with a human full-length MMP-13 ("hMMP-13FL") or a human MMP-13 catalytic domain ("hMMP-13CD") that is less than or equal to 50 micromolar. More preferred are compounds of Formula I, or a pharmaceutically acceptable salt thereof, which have an $IC_{50}$ with a human full-length MMP-13 ("hMMP-13FL") or a human MMP-13 catalytic domain ("hMMP-13CD") that is less than or equal to 10 micromolar.

The compound named 4-[1-oxo-7-(3-[1,2,3]triazol-1-ylprop-1-ynyl)-1H-isoquinolin-2-ylmethyl]benzoic acid is excluded from the invention because it was assayed with hMMP-13CD and was found to have an $IC_{50}$ that exceeded 50 micromolar.

Examples of biological methods useful for determining $IC_{50}$s for the invention compounds with an MMP are described below in Biological Methods 1 to 4. Any compound of Formula I, or a pharmaceutically acceptable salt thereof, or any form thereof as defined above, that does not have an $IC_{50}$ with any MMP enzyme that is less than, or equal to, 10 micromolar is excluded from this invention.

Some of the invention compounds are capable of further forming nontoxic pharmaceutically acceptable salts, including, but not limited to, acid addition and/or base salts. The acid addition salts are formed from basic invention compounds, whereas the base addition salts are formed from acidic invention compounds. All of these forms are within the scope of the compounds useful in the invention.

Pharmaceutically acceptable acid addition salts of the basic invention compounds include nontoxic salts derived from inorganic acids such as hydrochloric, nitric, phosphoric, sulfuric, hydrobromic, hydroiodic, hydrofluoric, phosphorous, and the like, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, malate, tartrate, methanesulfonate, and the like. Also contemplated are salts of amino acids such as arginate and the like and gluconate, galacturonate (see, for example, Berge S. M. et al., "Pharmaceutical Salts," J. of Pharma. Sci., 1977;66:1).

An acid addition salt of a basic invention compound is prepared by contacting the free base form of the compound with a sufficient amount of a desired acid to produce a nontoxic salt in the conventional manner. The free base form of the compound may be regenerated by contacting the acid addition salt so formed with a base, and isolating the free base form of the compound in the conventional manner. The free base forms of compounds prepared according to a process of the present invention differ from their respective acid addition salt forms somewhat in certain physical properties such as solubility, crystal structure, hygroscopicity, and the like, but otherwise free base forms of the invention compounds and their respective acid addition salt forms are equivalent for purposes of the present invention.

A nontoxic pharmaceutically acceptable base addition salt of an acidic invention compound may be prepared by contacting the free acid form of the compound with a metal cation such as an alkali or alkaline earth metal cation, or an amine, especially an organic amine. Examples of suitable metal cations include sodium cation ($Na^+$), potassium cation ($K^+$), magnesium cation ($Mg^{2+}$), calcium cation ($Ca^{2+}$), and the like. Examples of suitable amines are N,N'-dibenzylethylenediamine, chloroprocaine, choline, diethanolamine, dicyclohexylamine, ethylenediamine, N-methylglucamine, and procaine (see, for example, Berge, supra., 1977).

A base addition salt of an acidic invention compound may be prepared by contacting the free acid form of the compound with a sufficient amount of a desired base to produce the salt in the conventional manner. The free acid form of the compound may be regenerated by contacting the salt form so formed with an acid, and isolating the free acid of the compound in the conventional manner. The free acid forms of the invention compounds differ from their respective salt forms somewhat in certain physical properties such as solubility, crystal structure, hygroscopicity, and the like, but otherwise the salts are equivalent to their respective free acid for purposes of the present invention.

Certain invention compounds can exist in unsolvated forms as well as solvated forms, including hydrated forms. In general, the solvated forms, including hydrated forms, are equivalent to unsolvated forms and are encompassed within the scope of the present invention.

Certain of the invention compounds possess one or more chiral centers, and each center may exist in the R or S configuration. An invention compound includes any diastereomeric, enantiomeric, or epimeric form of the compound, as well as mixtures thereof.

Additionally, certain invention compounds may exist as geometric isomers such as the entgegen (E) and zusammen (Z) isomers of 1,2-disubstituted alkenyl groups or cis and trans isomers of disubstituted cyclic groups. An invention compound includes any cis, trans, syn, anti, entgegen (E), or zusammen (Z) isomer of the compound, as well as mixtures thereof.

Certain invention compounds can exist as two or more tautomeric forms. Tautomeric forms of the invention compounds may interchange, for example, via enolization/de-enolization, 1,2-hydride, 1,3-hydride, or 1,4-hydride shifts, and the like. An invention compound includes any tautomeric form of the compound, as well as mixtures thereof.

Some compounds of the present invention have alkenyl groups, which may exist as entgegen or zusammen conformations, in which case all geometric forms thereof, both entgegen and zusammen, cis and trans, and mixtures thereof, are within the scope of the present invention.

Some compounds of the present invention have cycloalkyl groups, which may be substituted at more than one carbon atom, in which case all geometric forms thereof, both cis and trans, and mixtures thereof, are within the scope of the present invention.

The invention compounds also include isotopically-labelled compounds, which are identical to those recited above, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Compounds of the present invention and pharmaceutically acceptable salts of said compounds which contain the aforementioned isotopes and/or other isotopes of other atoms are within the scope of this invention. Certain isotopically labelled compounds of the present invention, for example those into which radioactive isotopes such as $^3H$ and $^{14}C$ are incorporated, are useful in drug and/or substrate tissue distribution assays. Tritiated, i.e., $^3H$ and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of those described above in this invention can generally be prepared by carrying out the procedures incorporated by reference above or disclosed in the Schemes and/or in the Examples and Preparations below, by substituting a readily available isotopically labelled reagent for a non-isotopically labelled reagent.

All of the above-describe forms of an invention compound are included by the phrase "invention compound", a "compound of Formula I", a "compound of Formula I, or a pharmaceutically acceptable salt thereof", or any named species thereof, unless specifically excluded therefrom.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies and TNF receptor immunoglobulin molecules (such as Enbrel®), low dose methotrexate, lefunimide, hydroxychloroquine, d-penicillamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flurbiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as etoricoxib and rofecoxib, analgesics and intraarticular therapies such as corticosteroids and hyaluronic acids such as hyalgan and synvisc.

This invention also relates to a method of or a pharmaceutical composition for treating inflammatory processes and diseases comprising administering a compound of this invention to a mammal, including a human, cat, livestock or dog, wherein said inflammatory processes and diseases are defined as above and said inhibitory compound is used in combination with one or more other therapeutically active agents under the following conditions:

A.) where a joint has become seriously inflamed as well as infected at the same time by bacteria, fungi, protozoa and/or virus, said inhibitory compound is administered in combination with one or more antibiotic, antifungal, antiprotozoal and/or antiviral therapeutic agents;

B.) where a multi-fold treatment of pain and inflammation is desired, said inhibitory compound is administered in combination with inhibitors of other mediators of inflammation, comprising one or more members independently selected from the group consisting essentially of:
  (1) NSAIDs;
  (2) $H_1$-receptor antagonists;
  (3) kinin-$B_1$- and $B_2$-receptor antagonists;
  (4) prostaglandin inhibitors selected from the group consisting of PGD-, PGF-$PGI_2$- and PGE-receptor antagonists;
  (5) thromboxane $A_2$ ($TXA_2$-) inhibitors;
  (6) 5-, 12- and 15-lipoxygenase inhibitors;
  (7) leukotriene $LTC_4$-, $LTD_4/LTE_4$- and $LTB_4$-inhibitors;
  (8) PAF-receptor antagonists;
  (9) gold in the form of an aurothio group together with one or more hydrophilic groups;
  (10) immunosuppressive agents selected from the group consisting of cyclosporine, azathioprine and methotrexate;
  (11) anti-inflammatory glucocorticoids;
  (12) penicillamine;
  (13) hydroxychloroquine;
  (14) anti-gout agents including colchicine; xanthine oxidase inhibitors including allopurinol; and uricosuric agents selected from probenecid, sulfinpyrazone and benzbromarone;

C.) where older mammals are being treated for disease conditions, syndromes and symptoms found in geriatric mammals, said inhibitory compound is administered in combination with one or more members independently selected from the group consisting essentially of:
  (1) cognitive therapeutics to counteract memory loss and impairment;
  (2) anti-hypertensives and other cardiovascular drugs intended to offset the consequences of atherosclerosis, hypertension, myocardial ischemia, angina, congestive heart failure and myocardial infarction, selected from the group consisting of:
    a. diuretics;
    b. vasodilators;
    c. β-adrenergic receptor antagonists;
    d. angiotensin-II converting enzyme inhibitors (ACE-inhibitors), alone or optionally together with neutral endopeptidase inhibitors;
    e. angiotensin II receptor antagonists;
    f. renin inhibitors;
    g. calcium channel blockers;
    h. sympatholytic agents;
    i. $\alpha_2$-adrenergic agonists;
    j. α-adrenergic receptor antagonists; and
    k. HMG-CoA-reductase inhibitors (anti-hypercholesterolemics);
  (3) antineoplastic agents selected from:
    a. antimitotic drugs selected from:
      i. vinca alkaloids selected from:
        [1] vinblastine and
        [2] vincristine;
  (4) growth hormone secretagogues;
  (5) strong analgesics;
  (6) local and systemic anesthetics; and
  (7) $H_2$-receptor antagonists, proton pump inhibitors and other gastroprotective agents.

The active ingredient of the present invention may be administered in combination with inhibitors of other mediators of inflammation, comprising one or more members selected from the group consisting essentially of the classes of such inhibitors and examples thereof which include, matrix metalloproteinase inhibitors, aggrecanase inhibitors, TACE inhibitors, leucotriene receptor antagonists, IL-1 processing and release inhibitors, ILra, $H_1$-receptor antagonists; kinin-$B_1$- and $B_2$-receptor antagonists; prostaglandin inhibitors such as PGD-, PGF-$PGI_2$- and PGE-receptor antagonists; thromboxane $A_2$ (TXA2-) inhibitors; 5- and 12-lipoxygenase inhibitors; leukotriene $LTC_4$-, $LTD_4/LTE_4$- and $LTB_4$-inhibitors; PAF-receptor antagonists; gold in the form of an aurothio group together with various hydrophilic groups; immunosuppressive agents, e.g., cyclosporine, azathioprine and methotrexate; anti-inflammatory glucocorticoids; penicillamine; hydroxychloroquine; anti-gout agents, e.g., colchicine, xanthine oxidase inhibitors, e.g., allopurinol and uricosuric agents, e.g., probenecid, sulfinpyrazone and benzbromarone.

The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine and antimetabolites such as methotrexate.

The compounds of the present invention may also be used in combination with anti-hypertensives and other cardiovascular drugs intended to offset the consequences of atherosclerosis, including hypertension, myocardial ischemia including angina, congestive heart failure and myocardial infarction, selected from vasodilators such as hydralazine, β-adrenergic receptor antagonists such as propranolol, calcium channel blockers such as nifedipine, $\alpha_2$-adrenergic agonists such as clonidine, α-adrenergic receptor antagonists such as prazosin and HMG-CoA-reductase inhibitors (anti-hypercholesterolemics) such as lovastatin or atorvastatin.

The compounds of the present invention may also be administered in combination with one or more antibiotic, antifungal, antiprotozoal, antiviral or similar therapeutic agents.

The compounds of the present invention may also be used in combination with CNS agents such as antidepressants (such as sertraline), anti-Parkinsonian drugs (such as L-dopa, requip, mirapex, MAOB inhibitors such as selegine and rasagiline, comP inhibitors such as Tasmar, A-2 inhibitors, dopamine reuptake inhibitors, NMDA antagonists, nicotine agonists, dopamine agonists and inhibitors of neuronal nitric oxide synthase) and anti-Alzheimer's drugs such as donepezil, tacrine, COX-2 inhibitors, propentofylline or metryfonate.

The compounds of the present invention may also be used in combination with osteoporosis agents such as roloxifene, lasofoxifene, droloxifene or fosomax and immunosuppressant agents such as FK-506 and rapamycin.

The present invention also relates to the formulation of a compound of the present invention alone or with one or more other therapeutic agents which are to form the intended combination, including wherein said different drugs have varying half-lives, by creating controlled-release forms of said drugs with different release times which achieves relatively uniform dosing; or, in the case of non-human patients, a medicated feed dosage form in which said drugs used in the combination are present together in admixture in the feed composition. There is further provided in accordance with the present invention co-administration in which the combination of drugs is achieved by the simultaneous administration of said drugs to be given in combination; including co-administration by means of different dosage forms and routes of administration; the use of combinations in accordance with different but regular and continuous dosing schedules whereby desired plasma levels of said drugs involved are maintained in the patient being treated, even though the individual drugs making up said combination are not being administered to said patient simultaneously.

The invention method is useful in human and veterinary medicines for treating mammals suffering from one or more of the above-listed diseases and disorders.

All that is required to practice a method of this invention is to administer a compound of Formula I, or a pharmaceutically acceptable salt thereof, in an amount that is therapeutically effective for preventing, inhibiting, or reversing the condition being treated. The invention compound can be administered directly or in a pharmaceutical composition as described below.

A therapeutically effective amount, or, simply, effective amount, of an invention compound will generally be from about 1 to about 300 mg/kg of subject body weight of the compound of Formula I, or a pharmaceutically acceptable salt thereof. Typical doses will be from about 10 to about 5000 mg/day for an adult subject of normal weight for each component of the combination. In a clinical setting, regulatory agencies such as, for example, the Food and Drug Administration ("FDA") in the U.S. may require a particular therapeutically effective amount.

In determining what constitutes a nontoxic effective amount or a therapeutically effective amount of an invention compound for treating, preventing, or reversing one or more symptoms of any one of the diseases and disorders described above that are being treated according to the invention methods, a number of factors will generally be considered by the medical practitioner or veterinarian in view of the experience of the medical practitioner or veterinarian, including the Food and Drug Administration guidelines, or guidelines from an equivalent agency, published clinical studies, the subject's (e.g., mammal's) age, sex, weight and general condition, as well as the type and extent of the disease, disorder or condition being treated, and the use of other medications, if any, by the subject. As such, the administered dose may fall within the ranges or concentrations recited above, or may vary outside them, ie, either below or above those ranges, depending upon the requirements of the individual subject, the severity of the condition being treated, and the particular therapeutic formulation being employed. Determination of a proper dose for a particular situation is within the skill of the medical or veterinary arts. Generally, treatment may be initiated using smaller dosages of the invention compound that are less than optimum for a particular subject. Thereafter, the dosage can be increased by small increments until the optimum effect under the circumstance is reached. For convenience, the total daily dosage may be divided and administered in portions during the day, if desired.

Pharmaceutical compositions, described briefly here and more fully below, of an invention combination may be produced by formulating the invention combination in dosage unit form with a pharmaceutical carrier. Some examples of dosage unit forms are tablets, capsules, pills, powders, aqueous and nonaqueous oral solutions and suspensions, and parenteral solutions packaged in containers containing either one or some larger number of dosage units and capable of being subdivided into individual doses. Alternatively, the invention compounds may be formulated separately.

Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol, glycerin; sorbitol; polyethylene glycol; water; agar; alginic acid; isotonic saline, and phosphate buffer solutions; as well as other compatible substances normally used in pharmaceutical formulations.

The compositions to be employed in the invention can also contain other components such as coloring agents, flavoring agents, and/or preservatives. These materials, if present, are usually used in relatively small amounts. The compositions can, if desired, also contain other therapeutic agents commonly employed to treat any of the above-listed diseases and disorders.

The percentage of the active ingredients of a compound of Formula I, or a pharmaceutically acceptable salt thereof, in the foregoing compositions can be varied within wide limits, but for practical purposes it is preferably present in a total concentration of at least 10% in a solid composition and at least 2% in a primary liquid composition. The most satisfactory compositions are those in which a much higher proportion of the active ingredients are present, for example, up to about 95%.

Preferred routes of administration of an invention compound are oral or parenteral. However, another route of administration may be preferred depending upon the condition being treated. For exampled, topical administration or administration by injection may be preferred for treating conditions localized to the skin or a joint. Administration by transdermal patch may be preferred where, for example, it is desirable to effect sustained dosing.

It should be appreciated that the different routes of administration may require different dosages. For example, a useful intravenous ("IV") dose is between 5 and 50 mg, and a useful oral dosage is between 20 and 800 mg, of a compound of Formula I, or a pharmaceutically acceptable salt thereof. The dosage is within the dosing range used in treatment of the above-listed diseases, or as would be determined by the needs of the patient as described by the physician.

The invention compounds may be administered in any form. Preferably, administration is in unit dosage form. A unit dosage form of the invention compound to be used in this invention may also comprise other compounds useful in the therapy of diseases described above. A further description of pharmaceutical formulations useful for administering the invention compounds and invention combinations is provided below.

The active components of the invention combinations, may be formulated together or separately and may be administered together or separately. The particular formulation and administration regimens used may be tailored to the particular patient and condition being treated by a practitioner of ordinary skill in the medical or pharmaceutical arts.

The advantages of using an invention compound in a method of the instant invention include the nontoxic nature of the compounds at and substantially above therapeutically effective doses, their ease of preparation, the fact that the compounds are well-tolerated, and the ease of topical, IV, or oral administration of the drugs.

Another important advantage is that the present invention compounds more effectively target a particular disease that is responsive to inhibition of MMP-13 with fewer undesirable side effects than similar compounds that inhibit MMP-13 that are not invention compounds. This is so because the instant invention compounds of Formula I, or a pharmaceutically acceptable salt thereof, do not directly, or indirectly via a bridging water molecule, ligate, coordinate to, or bind to the catalytic zinc cation of MMP-13, but instead bind at a different location from where natural substrate binds to MMP-13. The binding requirements of an allosteric MMP-13 binding site are unique to MMP-13, and account for the specificity of the invention compounds for inhibiting MMP-13 over any other MMP enzyme. This binding mode has not been reported in the art. Indeed, prior art inhibitors of MMP-13 bind to the catalytic zinc cations of other MMP enzymes as well as to the catalytic zinc cation of MMP-13, and are consequently significantly less selective inhibitors of MMP-13 enzyme.

The invention compounds which are invention compounds, and pharmaceutically acceptable salts thereof, are thus therapeutically superior to other inhibitors of MMP-13, or even tumor necrosis factor-alpha converting enzyme ("TACE"), because of fewer undesirable side effects from inhibition of the other MMP enzymes or TACE. For example, virtually all prior art MMP inhibitors tested clinically to date have exhibited an undesirable side effect known as muscoloskeletal syndrome ("MSS"). MSS is associated with administering an inhibitor of multiple MMP enzymes or an inhibitor of a particular MMP enzyme such as MMP-1. MSS will be significantly reduced in type and severity by administering the invention compound instead of any prior art MMP-13 inhibitor, or a pharmaceutically acceptable salt thereof. The invention compounds are superior to similar compounds that interact with the catalytic zinc cation of the MMP-13 enzyme as discussed above, even if similar compounds show some selectivity for the MMP-13.

It is expected that nearly all, if not all, compounds of Formula I, or pharmaceutically acceptable salts thereof, are invention compounds.

This advantage of the instant compounds will also significantly increase the likelihood that agencies which regulate new drug approvals, such as the United States Food and Drug Administration, will approve the instant compounds versus a competing similar compound that does not allosterically bind to MMP-13 as discussed above even in the unlikely event that the two compounds behaved similarly in clinical trials. These regulatory agencies are increasingly aware that clinical trials, which test drug in limited population groups, do not always uncover safety problems with a drug, and thus all other things being equal, the agencies will favor the drug with the lowest odds of producing undesirable side effects.

Another important advantage is that the disease modifying properties of the invention compounds provide patients suffering from cartilage damage, arthritis, preferably osteoarthritis, inflammation and/or pain with both relief of symptoms and prevention or inhibition of the underlying disease pathology such as cartilage degradation. There is no currently approved drug for disease modification of cartilage damage, including in osteoarthritis.

Any invention compound is readily available, either commercially, or by synthetic methodology, well known to those skilled in the art of organic chemistry. For specific syntheses, see the examples below and the preparations of invention compound outlined in the Schemes below.

Intermediates for the synthesis of a compound of Formula I, or a pharmaceutically acceptable salt thereof, may be prepared by one of ordinary skill in the art of organic chemistry by adapting various synthetic procedures incorporated by reference above or that are well-known in the art of organic chemistry. These synthetic procedures may be found in the literature in, for example, Reagents for Organic Synthesis, by Fieser and Fieser, John Wiley & Sons, Inc, New York, 2000; Comprehensive Organic Transformations, by Richard C. Larock, VCH Publishers, Inc, New York, 1989; the series Compendium of Organic Synthetic Methods, 1989, by Wiley-Interscience; the text Advanced Organic Chemistry, $4^{th}$ edition, by Jerry March, Wiley-Interscience, New York, 1992; or the Handbook of Heterocyclic Chemistry by Alan R. Katritzky, Pergamon Press Ltd, London, 1985, to name a few. Alternatively, a skilled artisan may find methods useful for preparing the intermediates in the chemical literature by searching widely available databases such as, for example, those available from the Chemical Abstracts Service, Columbus, Ohio, or MDL Information Systems GmbH (formerly Beilstein Information Systems GmbH), Frankfurt, Germany.

Preparations of the invention compounds may use starting materials, reagents, solvents, and catalysts that may be purchased from commercial sources or they may be readily prepared by adapting procedures in the references or resources cited above. Commercial sources of starting materials, reagents, solvents, and catalysts useful in preparing invention compounds include, for example, The Aldrich Chemical Company, and other subsidiaries of Sigma-Aldrich Corporation, St. Louis, Mo., BACHEM, BACHEM A.G., Switzerland, or Lancaster Synthesis Ltd, United Kingdom.

Syntheses of some invention compounds may utilize starting materials, intermediates, or reaction products that contain a reactive functional group. During chemical reactions, a reactive functional group may be protected from reacting by a protecting group that renders the reactive functional group substantially inert to the reaction conditions employed. A protecting group is introduced onto a starting material prior to carrying out the reaction step for which a protecting group is needed. Once the protecting group is no longer needed, the protecting group can be removed. It is well within the ordinary skill in the art to introduce protecting groups during a synthesis of a compound of Formula I, or a pharmaceutically acceptable salt thereof, and then later remove them. Procedures for introducing and removing protecting groups are known and referenced such as, for example, in Protective Groups in Organic Synthesis, $2^{nd}$ ed., Greene T. W. and Wuts P. G., John Wiley & Sons, New York: New York, 1991, which is hereby incorporated by reference.

Thus, for example, protecting groups such as the following may be utilized to protect amino, hydroxyl, and other groups: carboxylic acyl groups such as, for example, formyl, acetyl, and trifluoroacetyl; alkoxycarbonyl groups such as, for example, ethoxycarbonyl, tert-butoxycarbonyl (BOC), $\beta,\beta,\beta$-trichloroethoxycarbonyl (TCEC), and $\beta$-iodoethoxycarbonyl; aralkyloxycarbonyl groups such as, for example, benzyloxycarbonyl (CBZ), para-methoxybenzyloxycarbonyl, and 9-fluorenylmethyloxycarbonyl (FMOC); trialkylsilyl groups such as, for example, trimethylsilyl (TMS) and tert-butyldimethylsilyl (TBDMS); and other groups such as, for example, triphenylmethyl (trityl), tetrahydropyranyl, vinyloxycarbonyl, ortho-nitrophenylsulfenyl, diphenylphosphinyl, para-toluenesulfonyl (Ts), mesyl, trifluoromethanesulfonyl, and benzyl. Examples of procedures for removal of protecting groups include hydrogenolysis of CBZ groups using, for example, hydrogen gas at 50 psi in the presence of a hydrogenation catalyst such as 10% palladium on carbon, acidolysis of BOC groups using, for example, hydrogen chloride in dichloromethane, trifluoroacetic acid (TFA) in dichloromethane, and the like, reaction of silyl groups with fluoride ions, and reductive cleavage of TCEC groups with zinc metal.

A general synthesis of the compounds of Formula I is outlined below in Scheme 1. For illustration purposes, Scheme 1 describes the preparation of a compound of Formula I wherein Q is a carbon-carbon triple bond, Y is C(=O), $W^1$ is N, $R^4$, $W^2$, $W^3$, and $W^4$ are each CH, and n is 0. In principle, any compound of Formula I wherein Q is a carbon-carbon triple bond may be prepared according to the procedure outlined in Scheme 1.

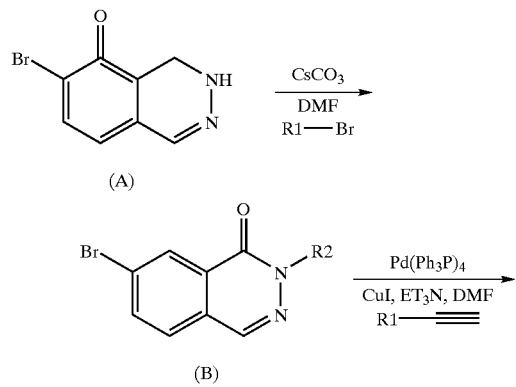

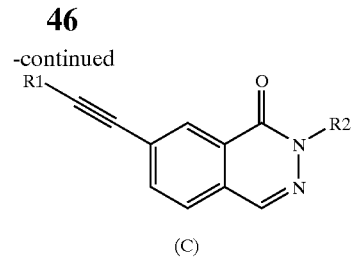

wherein $R^1$ and $R^2$ are as defined above for Formula I.

In Scheme 1, a suspension of 7-bromo-1-hydroxy-3-azaisoquinoline (A) can be alkylated in an aprotic solvent such as dimethylformamide when treated with a common alkylating agent such as an alkyl halide or benzyl halide, generally in the presence of a base such as cesium carbonate, potassium carbonate, or triethylamine.

The alkylated isoquinoline (B) can be further reacted with a variety of alkynes using standard coupling conditions known to those skilled in the art, for example, using a catalyst such as $Pd(PPh_3)_4$ or $PdCl_2((PPh_3)_2$, with or without an accompanying ligand, and in the presence of a base, such as triethylamine or diisopropylamine, to give compounds of this invention (C). Where appropriate, cleavage of t-butyl protecting groups is carried out under standard conditions, for example, moderately acidic hydrolysis, to afford the carboxylic acid.

The invention compounds can be isolated and purified by standard methods such as crystallization from solvents such as alkanes, alkyl esters and ethyl acetate, and chromatography over solid supports such as silica gel, eluting with solvents such as dichloromethane, acetonitrile, tetrahydrofuran, hexanes, ethyl acetate.

The synthesis is further illustrated in Scheme 2a below.

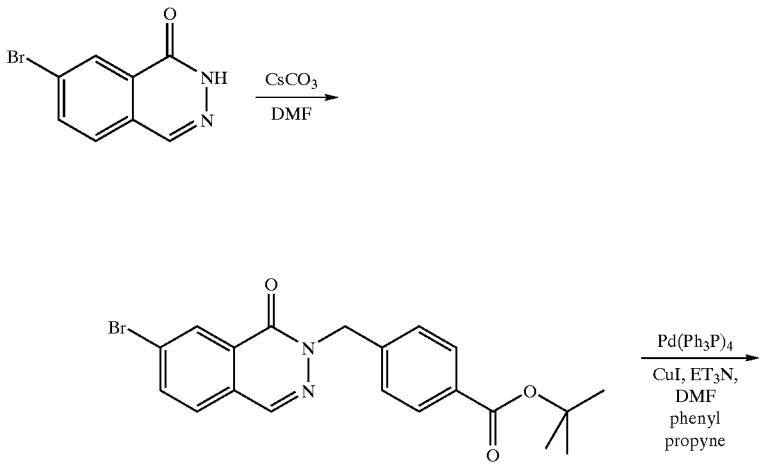

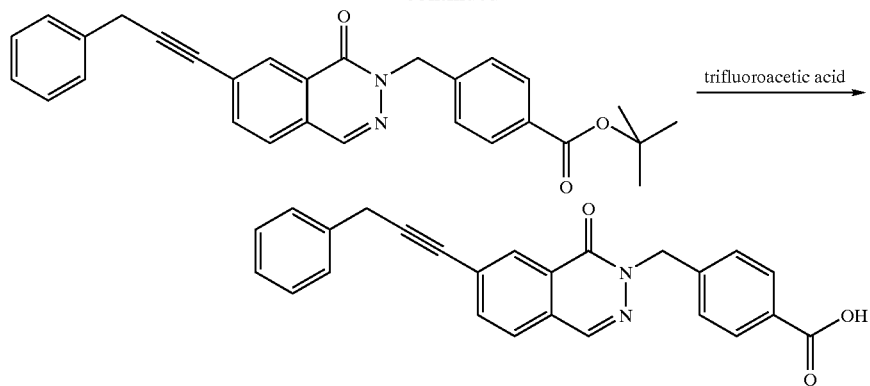

wherein R¹ and R are as defined above for Formula I.

Compounds of Formula I wherein W¹ is N and W² to W⁴ are each C—R⁷ are also known as phthalazinone derivatives. Phthalazinone derivatives may also be prepared according to the procedures referenced below for FIG. 1.

In FIG. 1, a bromo-substituted phthalazinone of formula (D) and a carboxylic acid ester of formula (E) may be prepared according to the procedure described in Chem. Pharm. Bull., 1985;33(7):2809–2820. Compounds of formulas (D) and (E) may be used to prepare compounds of Formula III, which are compounds of Formula I wherein Y is C(O) and Q is a carbon-carbon triple bond, amide, or ester linker. FIG. 1.

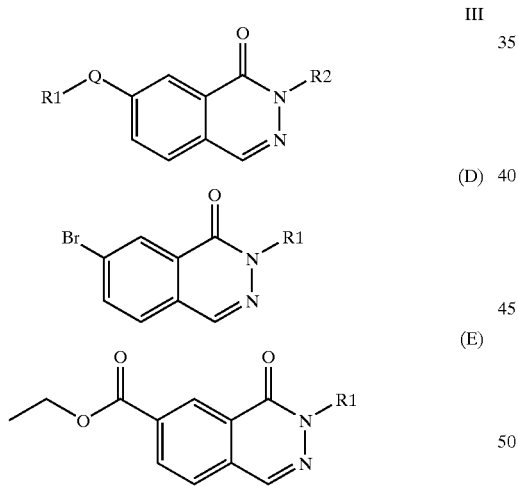

wherein R¹ and R² are as defined above for Formula I.

Compounds of Formula I wherein one of W², W³, and W⁴ is N and W¹ the other two of W², W³, and W⁴ are each C—R⁷ are also known as naphthyridine derivatives. Naphthyridine derivatives may also be prepared according to the procedures referenced below for FIG. 2.

In FIG. 2, bromo-substituted naphthyridines or carboxylic acid ester naphthyridines of formulas (F), (G), and (H), wherein R is Br or, for example, EtOC(O), respectively, may be prepared according to the procedure described in Chem. Pharm. Bull., 1985;33(2):626–633. Compounds of formulas (F), (G), and (H) may be used to prepare compounds of Formula IV, V, and VI, respectively, which are compounds of Formula I wherein Y is C(O) and Q is a carbon-carbon triple bond, amide, or ester linker.
FIG. 2.

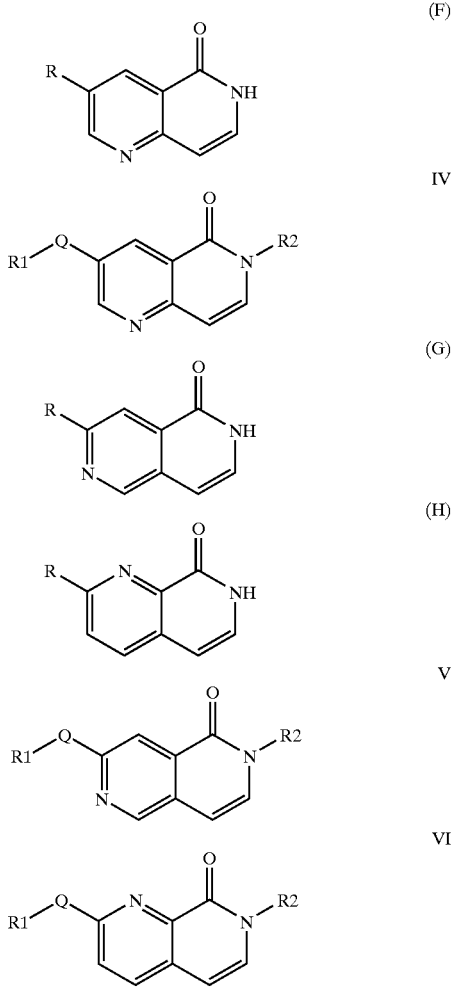

Compounds of Formula I wherein one of W¹, W², W³, and W⁴ is N, the other three of W¹, W², W³, and W⁴ are each C—R⁷, Q is a heterocyclic linker, and Y is C(O) may be prepared according to the procedures outlined below in Scheme 2b. These are compounds of Formula (VII), wherein V and X are as defined above.

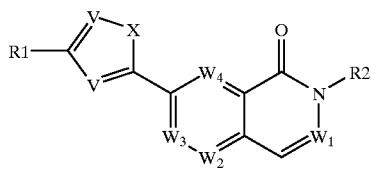

In Scheme 2b, bromo-substituted compounds of formula (I) may be converted, for example, to carboxylic acid esters of formula (J) using conventional carbonylation methods. Alkylation of the compounds of formula (J), followed by hydrolysis will afford the carboxylic acid intermediate of formula (K), which can then be used to make several of the heterocyclic linkers, including compounds of Formula (VII).

Scheme 2b.

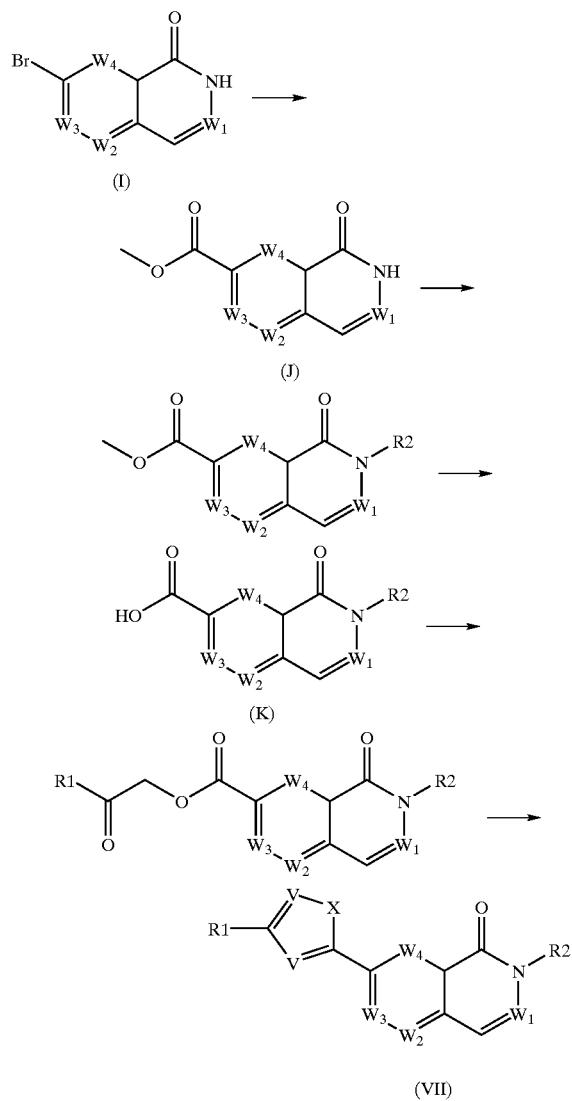

Illustrative examples of the synthesis of compounds of Formula I are described below in the Examples.

EXAMPLE 1A

4-[1-Oxo-7-(3-phenyl-prop-1-ynyl)-1H-3-azaisoquinolin-2-ylmethyl]benzoic acid tert-butyl ester Step (1): 4-(7-bromo-1-oxo-1H-3-azaisoquinolin-2-ylmethyl)benzoic acid tert-butyl ester A suspension of 7-bromo-1-hydroxy-3-azaisoquinoline (7.02 g, 28.2 mmol) in dimethylformamide (75 mL) is treated with 4-bromomethylbenzoic acid tert-butyl ester (12.5 g, 36.7 mmol) and cesium carbonate (11.94 g, 36.7 mmol), then stirred overnight at room temperature. The dimethylformamide is evaporated in vacuo, the residue is diluted with ethyl acetate, washed with 1N HCl, the organic portion washed with brine, dried over $MgSO_4$ and evaporated to dryness. The residue is triturated with hot hexanes/ethyl acetate, cooled to room temperature, and the solid is collected by filtration and dried to give the desired product.

Step (2): 4-[1-oxo-7-(3-phenyl-prop-1-ynyl)-1H-3-azaisoquinolin-2-ylmethyl]benzoic acid tert-butyl ester

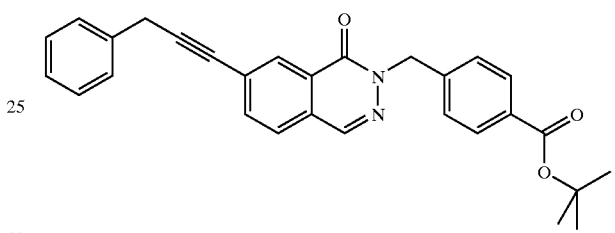

A solution of 4-(7-bromo-1-oxo-1H-3-azaisoquinolin-2-ylmethyl)benzoic acid tert-butyl ester (1.50 g, 3.62 mmol) in dimethylformamide (10 mL) is degassed with nitrogen, then treated with triethyl-amine (2.07 mL, 14.8 mmol), CuI (0.050 g, 0.26 mmol), $Pd(Ph_3P)_4$ (0.173 g, 0.15 mmol), and 3-phenyl-1-propyne (1.13 mL, 9.05 mmol). The reaction mixture is heated in an oil bath at 65° C. for 5 hours, cooled to room temperature, the DMF is evaporated, and the residue is dissolved in ethyl acetate. The solution is washed with 1N HCl, brine, dried over $MgSO_4$ and evaporated onto silica gel. Purification on a 3.5×18 cm silica gel column eluted with hexane/ethyl acetate 4:1, followed by drying, will afford the desired product.

$^1$H-NMR (CDCl$_3$); d 8.53 (d, 1H), 7.95–7.93 (d, 2H), 7.67–7.65 (dd, 1H), 7.43–7.41 (d, 3H), 7.36–7.31 (m, 4H), 7.28–7.24 (m, 1H), 7.04–7.03 (d, 1H), 6.46–6.44 (d, 1H), 5.24 (s, 2H), 3.86 (s, 2H), 1.57 (s, 9H). MS: M$^+$+1=450.2 Da

EXAMPLE 1

4-[1-Oxo-7-(3-phenyl-prop-1-ynyl)-1H-3-azaisoquinolin-2-ylmethyl]benzoic acid

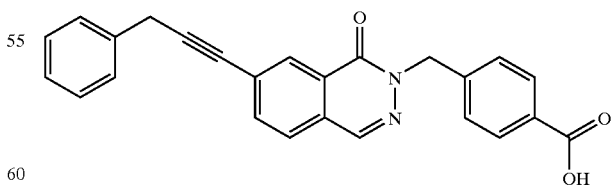

A solution of 4-[1-oxo-7-(3-phenyl-prop-1-ynyl)-1H-3-azaisoquinolin-2-ylmethyl]benzoic acid tert-butyl ester [0.20 g, 0.44 mmol, Example 1A, Step (2)] is treated with trifluoroacetic acid (5 mL) and the reaction mixture stirred at room temperature for 30 minutes. The solution is evaporated to dryness, the residue is dissolved in ethyl acetate, washed with water, brine, dried over MgSO₄ and evaporated to dryness. The brown solid is triturated with acetonitrile, the solid collected by filtration, and washed with acetonitrile. The solid is then dissolved in hot ethyl acetate, evaporated onto silica gel, and purified on a 2.5×10 cm silica gel column eluted with hexanes/ethyl acetate 1:1, followed by ethyl acetate. Drying will afford the purified product.

EXAMPLE 2

7-(3-Phenyl-prop-1-ynyl)-2-(4-trifluoromethylbenzyl)-2H-5-azaisoquinolin-1-one Step (1): 7-bromo-2-(4-triflurormethylbenzyl)-2H-5-azaisoquionlin-one The alkylation of 7-bromo-1-hydroxy-5-azaisoquinoline (1.00 g, 4.40 mmol) using 4-trifluoromethyl-benzyl bromide (1.60 g, 6.69 mmol) and cesium carbonate (2.18 g, 6.69 mmol) in dimethyl-formamide is carried out as previously described in Example 1, Step (1). Purification on a silica gel column eluted with hexanes/ethyl acetate 2:1, followed by trituration with hexanes/ethyl acetate 4:1 will afford the desired product.

Step (2): 7-(3-phenyl-prop-1-ynyl)-2-(4-trifluoromethylbenzyl)-2H-5-azaisoquinolin-1-one

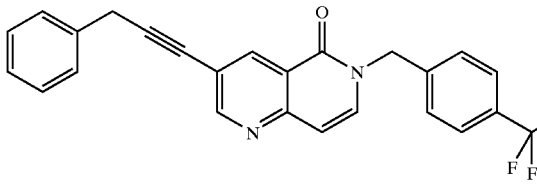

The coupling of 7-bromo-2-(4-triflurormethylbenzyl)-2H-5-azaisoquionlin-one (1.16 g, 3.04 mmol) with 3-phenyl-1-propyne (0.94 mL, 7.6 mmol) using triethylamine (0.84 mL, 6.10 mmol), CuI (0.041 g, 0.22 mmol), and Pd(Ph₃P)₄ (0.14 g, 0.12 mmol) in dimethylformamide is carried out as described in Example 1, Step (2). The compound is purified on a 3.5×18 cm silica gel column eluted with hexanes/ethyl acetate 3:1, then triturated with ether and recrystallized from hexanes/ethyl acetate to give the desired product.

EXAMPLE 3

2-(3-Fluorobenzyl)-7-(3-phenyl-prop-1-ynyl)-2H-5-azaisoquinolin-1-one

Step (1): 7-bromo-2-(3-fluorobenzyl)-2H-5-azaisoquinolin-1-one

The alkylation of 7-bromo-1-hydroxy-5-azaisoquinoline (1.00 g, 4.40 mmol) using 3-fluorobenzyl bromide (1.27 g, 6.69 mmol) and cesium carbonate (2.18 g, 6.69 mmol) in dimethylformamide is carried out as previously described in Example 1, Step (1). Purification on a silica gel column eluted with hexanes/ethyl acetate 3:1, followed by trituration with hexanes/ethyl acetate 4:1 will afford the desired product.

Step (2): 2-(3-Fluorobenzyl)-7-(3-phenyl-prop-1-ynyl)-2H-5-azaisoquinolin-1-one

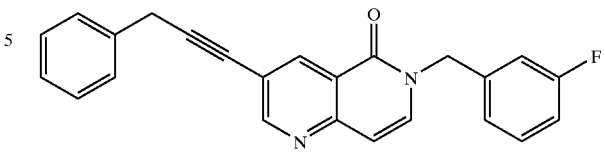

The coupling of 7-bromo-2-(3-fluorobenzyl)-2H-5-azaisoquinolin-1-one (0.60 g, 1.81 mmol) with 3-phenyl-1-propyne (0.56 mL, 4.5 mmol) using triethylamine (1.03 mL, 7.4 mmol), CuI (0.025 g, 0.13 mmol), and Pd(Ph₃P)₄ (0.087 g, 0.075 mmol) in dimethylformamide is carried out as described in Example 1, Step (2). The compound is purified by preparative HPLC to give the desired product.

EXAMPLE 4

3-[1-Oxo-7-(3-phenyl-prop-1-ynyl)-1H-6-azaisoquinolin-2-ylmethyl]benzonitrile Step (1): 3-(7-bromo-1-oxo-1H-6-azaisoquinolin-2-ylmethyl)benzonitrile The alkylation of 7-bromo-1-hydroxy-6-azaisoquinoline (1.00 g, 4.40 mmol) using 3-cyanobenzyl bromide (1.31 g, 6.69 mmol) and cesium carbonate (2.18 g, 6.69 mmol) in dimethylformamide is carried out as previously described in Example 1, Step (1). Purification on a silica gel column eluted with hexanes/ethyl acetate 3:1, followed by trituration with hexanes/ethyl acetate 4:1 will afford the desired product.

Step (2): 3-[1-oxo-7-(3-Phenyl-prop-1-ynyl)-1H-6-azaisoquinolin-2-ylmethyl]benzonitrile

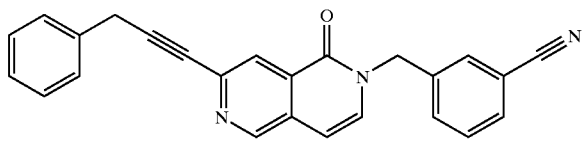

The coupling of 3-(7-bromo-1-oxo-1H-6-azaisoquinolin-2-ylmethyl)benzonitrile (0.85 g, 2.51 mmol) with 3-phenyl-1-propyne (0.78 mL, 6.3 mmol) using triethylamine (0.70 mL, 5.0 mmol), CuI (0.034 g, 0.18 mmol), and Pd(Ph₃P)₄ (0.20 g, 0.17 mmol) in dimethylformamide is carried out as described in Example 1, Step (2). Purification is carried out on a silica gel column eluted with hexanes/ethyl acetate 3:1 to give the desired product.

EXAMPLE 5

4-[1-Oxo-7-(3-phenyl-prop-1-ynyl)-1H-6-azaisoquinolin-2-ylmethyl]benzenesulfonamide Step (1): 4-(7-bromo-1-oxo-1H-6-azaisoquinolin-2-ylmethyl)benzenesulfonamide The alkylation of 7-bromo-1-hydroxy-6-azaisoquinoline (1.00 g, 4.40 mmol) using 4-bromomethyl-benzene sulfonamide (1.67 g, 6.69 mmol) and cesium carbonate (2.18 g, 6.69 mmol) in dimethyl-formamide is carried out as previously described in Example 1, Step (1). Purification on a silica gel column eluted with hexanes/ethyl acetate 3:1, followed by trituration with hexanes/ethyl acetate 4:1 will afford the desired product.

Step (2): 4-[1-oxo-7-(3-phenyl-prop-1-ynyl)-1H-6-azaisoquinolin-2-ylmethyl]benzenesulfonamide

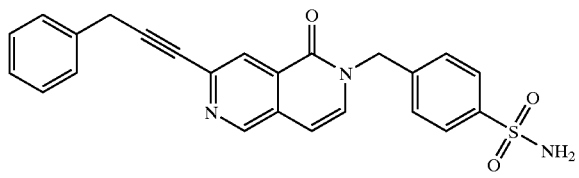

The coupling of 4-(7-bromo-1-oxo-1H-6-azaisoquinolin-2-ylmethyl)benzenesulfonamide (0.71 g, 1.81 mmol) with 3-phenyl-1-propyne (0.56 mL, 4.51 mmol) using triethylamine (0.50 mL, 3.61 mmol), CuI (0.025 g, 0.13 mmol), and Pd(Ph$_3$P)$_4$ (0.084 g, 0.07 mmol) in dimethylformamide is carried out as described in Example 1, Step (2). Purification is carried out on a silica gel column eluted with hexanes/ethyl acetate 3:1 to give the desired product.

EXAMPLE 6

4-[1-Oxo-7-(3-phenyl-prop-1-ynyl)-1H-8-azaisoquinolin-2-ylmethyl]benzoic acid Methyl Ester Step (1): 4-(7-bromo-1-oxo-1H-8-azaisoquinolin-2-ylmethyl)benzoic acid methyl ester The alkylation of 7-bromo-1-hydroxy-8-azaisoquinoline (1.00 g, 4.46 mmol) using methyl 4-(bromomethyl)benzoate (1.53 g, 6.69 mmol) and cesium carbonate (2.18 g, 6.69 mmol) in dimethylformamide is carried out as previously described in Example 1, Step (1). The solid is crystallized from hexanes/ethyl acetate 2:1, the white crystals collected by filtration and dried to give the desired product.

Step (2): 4-[1-oxo-7-(3-phenyl-prop-1-ynyl)-1H-8-azaisoquinolin-2-ylmethyl]benzoic acid methyl ester

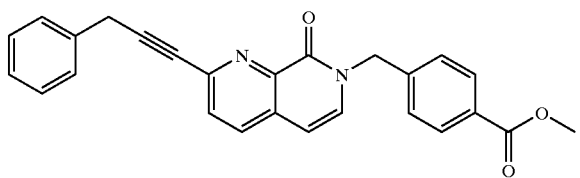

The coupling of 4-(7-bromo-1-oxo-1H-8-azaisoquinolin-2-ylmethyl)benzoic acid methyl ester (0.35 g, 0.94 mmol) with 3-phenyl-1-propyne (0.29 mL, 2.35 mmol) using triethylamine (0.54 mL, 3.86 mmol), CuI (0.013 g, 0.07 mmol), and Pd(Ph$_3$P)$_4$ (0.043 g, 0.04 mmol) in dimethylformamide is carried out as described in Example 1, Step (2). Purification on a silica gel column eluted with hexane/ethyl acetate 2:1, followed by drying, will afford the desired product.

EXAMPLE 7

3-[1-Oxo-7-(3-phenyl-prop-1-ynyl)-1H-8-azaisoquinolin-2-ylmethyl]benzoic acid Methyl Ester Step (1): 3-(7-bromo-1-oxo-1H-8-azaisoquinolin-2-ylmethyl)benzoic acid methyl ester The alkylation of 7-bromo-1-hydroxy-8-azaisoquinoline (1.00 g, 4.46 mmol) using methyl 3-(bromomethyl)benzoate (1.53 g, 6.69 mmol) and cesium carbonate (2.18 g, 6.69 mmol) in dimethyl-formamide is carried out as previously described in Example 1, Step (1). Purification on a silica gel column eluted with hexanes/ethyl acetate 3:1, followed by trituration with hexanes/ethyl acetate 4:1 will afford the desired product.

Step (2): 3-[1-oxo-7-(3-phenyl-prop-1-ynyl)-1H-8-azaisoquinolin-2-ylmethyl]benzoic acid methyl ester

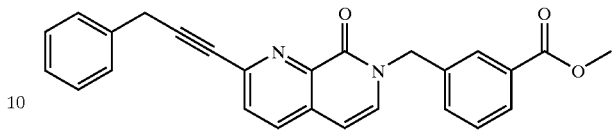

The coupling of 3-(7-bromo-1-oxo-1H-8-azaisoquinolin-2-ylmethyl)benzoic acid methyl ester (1.20 g, 3.22 mmol) with 3-phenyl-1-propyne (1.00 mL, 8.06 mmol) using triethylamine (0.92 mL, 6.60 mmol), CuI (0.044 g, 0.23 mmol), and Pd(Ph$_3$P)$_4$ (0.15 g, 0.13 mmol) in dimethylformamide is carried out as described in Example 1, Step (2). A portion of the resulting red oil is purified on the preparatory HPLC using 80:20 acetonitrile/water (0.1% TFA), evaporated to dryness, dissolved in ethyl acetate, washed with saturated aqueous sodium bicarbonate solution, dried over MgSO$_4$ and evaporated to dryness. Drying will afford the desired product.

EXAMPLE 8

2-(4-Fluorobenzyl)-7-3-phenylprop-1-ynyl-2H-3,5-diazaisoquinolin-1-one

Step (1): 7-bromo-2-(4-fluorobenzyl)-2H-3,5-diazaisoquinolin-1-one

The alkylation of 7-bromo-1-hydroxy-3,5-diazaisoquinoline (1.00 g, 4.46 mmol) using methyl 4-fluoro-benzyl bromide (1.27 g, 6.69 mmol) and cesium carbonate (2.18 g, 6.69 mmol) in dimethyl-formamide is carried out as previously described in Example 1, Step (1). Purification on a silica gel column eluted with hexanes/ethyl acetate 3:1, followed by trituration with hexanes/ethyl acetate 4:1 will afford the desired product.

Step (2): 2-(4-fluorobenzyl)-7-3-phenylprop-1-ynyl-2H-3,5-diazaisoquinolin-1-one

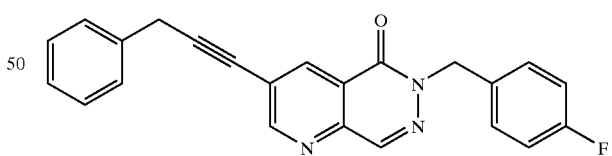

The coupling of 7-bromo-2-(4-fluorobenzyl)-2H-3,5-diazaisoquinolin-1-one (0.88 g, 2.65 mmol) with 3-phenyl-1-propyne (0.82 mL, 6.62 mmol) using triethylamine (1.51 mL, 10.8 mmol), CuI (0.036 g, 0.19 mmol), and Pd(Ph$_3$P)$_4$ (0.13 g, 0.11 mmol) in dimethylformamide is carried out as described in Example 1, Step (2). The resulting red oil is purified on the preparatory HPLC using 80:20 acetonitrile/water (0.1% TFA), evaporated to dryness, dissolved in ethyl acetate, washed with saturated aqueous sodium bicarbonate solution, dried over MgSO$_4$ and evaporated to dryness. Drying will afford the desired product.

EXAMPLE 9

7-(3-phenylprop-1-ynyl)-2-(3-trifluoromethylbenzyl)-2H-3,6-diazaisoquinolin-1-one Step (1): 7-bromo-2-(3-trifluoromethylbenzyl)-2H-3,6-diazaisoquinolin-1-one The alkylation of 7-bromo-1-hydroxy-3,6-diazaisoquinoline (1.00 g, 4.46 mmol) using 3-trifluoromethyl-benzyl bromide (1.60 g, 6.69 mmol) and cesium carbonate (2.18 g, 6.69 mmol) in dimethylformamide is carried out as previously described in Example 1, Step (1). Purification on a silica gel column eluted with hexanes/ethyl acetate 3:1, followed by trituration with hexanes/ethyl acetate 4:1 will afford the desired product.

Step (2): 7-(3-phenylprop-1-ynyl)-2-(3-trifluoromethylbenzyl)-2H-3,6-diazaisoquinolin-1-one

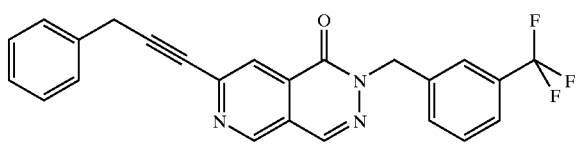

The coupling of 7-bromo-2-(3-trifluoromethyl)-2H-3,6-diazaisoquinolin-1-one (1.22 g, 3.20 mmol) with 3-phenyl-1-propyne (0.93 mL, 8.0 mmol) using triethylamine (1.82 mL, 13.1 mmol), CuI (0.043 g, 0.23 mmol), and Pd(Ph$_3$P)$_4$ (0.15 g, 0.13 mmol) in dimethylformamide is carried out as described in Example 1, Step (2). The resulting red oil is purified on the preparatory HPLC using 80:20 acetonitrile/water (0.1% TFA), washed with saturated aqueous sodium bicarbonate solution, dried over MgSO$_4$ and evaporated to dryness. Drying will afford the desired product.

EXAMPLE 10

2-(3-Chlorobenzyl)-7-(3-phenylprop-1-ynyl)-2H-3,8-diazaisoquinolin-1-one

Step (1): 7-bromo-2-(3-chlorobenzyl)-2H-3,8-diazaisoquinolin-1-one

The alkylation of 7-bromo-1-hydroxy-3,8-diazaisoquinoline (1.00 g, 4.46 mmol) using 3-Chlorobenzyl bromide (1.37 g, 6.69 mmol) and cesium carbonate (2.18 g, 6.69 mmol) in dimethyl-formamide is carried out as previously described in Example 1, Step (1). Trituration with hexanes/ethyl acetate 10:1 will afford the desired product.

Step 2): 2-(3-chlorobenzyl)-7-(3-phenylprop-1-ynyl)-2H-3,8-diazaisoquinolin-1-one

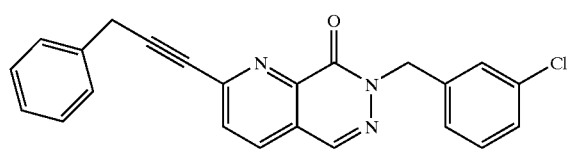

The coupling of 7-bromo-2-(3-chlorobenzyl)-2H-3,8-diazaisoquinolin-1-one (0.80 g, 2.29 mmol) with 3-phenyl-1-propyne (0.71 mL, 5.74 mmol) using triethylamine (0.64 mL, 4.59 mmol), CuI (0.031 g, 0.16 mmol), and Pd(Ph$_3$P)$_4$ (0.106 g, 0.092 mmol) in dimethylformamide (6 mL) is carried out as described in Example 1, Step (2). The resulting red oil is evaporated onto silica gel and purified on a 3.5×20 cm silica gel column eluted with hexanes/ethyl acetate 3:1. Drying will afford the desired product.

EXAMPLE 11

2-(3,4-Difluorobenzyl)-7-(3-phenylprop-1-ynyl)-2H-5,8-diazaisoquinolin-1-one Step (1): 7-bromo-2-(3,4-difluorobenzyl)-2-5,8-diazaisoquinolin-1-one The alkylation of 7-bromo-1-hydroxy-5,8-diazaisoquinoline (1.00 g, 4.46 mmol) using 3,4-difluorobenzyl bromide (1.38 g, 6.69 mmol) and cesium carbonate (2.18 g, 6.69 mmol) in dimethyl-formamide is carried out as previously described in Example 1, Step (1). Trituration with hexanes/ethyl acetate 10:1 will afford the desired product.

Step (2): 2-(3,4-difluorobenzyl)-7-(3-phenylprop-1-ynyl)-2H-5,8-diazaisoquinolin-1-one

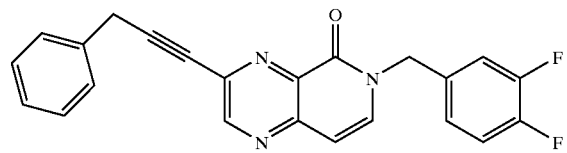

The coupling of 7-bromo-2-(3,4-difluorobenzyl)-2H-5,8-diazaisoquinolin-1-one (0.80 g, 2.28 mmol) with 3-phenyl-1-propyne (0.71 mL, 5.74 mmol) using triethylamine (0.64 mL, 4.59 mmol), CuI (0.031 g, 0.16 mmol), and Pd(Ph$_3$P)$_4$ (0.106 g, 0.092 mmol) in dimethylformamide (6 mL) is carried out as described in Example 1, Step (2). The resulting red oil is evaporated onto silica gel and purified on a 3.5×20 cm silica gel column eluted with hexanes/ethyl acetate 3:1. The resulting red solid is triturated with ethyl ether and dried. This will afford the desired product.

EXAMPLE 12

2-(3,5-Difluoro-4-hydroxybenzyl)-7-[3-(4H-[1,2,3]triazol-4-yl)prop-1-ynyl]-2H-3-azaisoquinolin-1-one Step (1): 7-bromo-2-(3,5-difluoro-4-hydroxybenzyl)-2-3-azaisoquinolin-1-one The alkylation of 7-bromo-1-hydroxy-3-azaisoquinoline (1.30 g, 5.80 mmol) using 4-bromomethyl-2,6-difluorophenol (1.68 g, 7.54 mmol) and cesium carbonate (2.46 g, 7.54 mmol) in dimethyl-formamide is carried out as previously described in Example 1, Step (1). The solid is collected by filtration, washed with water, ethyl acetate, and allowed to air dry under house vacuum. Drying will afford the desired product.

Step (2): 2-(3,5-difluoro-4-hydroxybenzyl)-7-[3-(4H-[1,2,3]triazol-4-yl)prop-1-ynyl]-2H-3-azaisoquinolin-1-one

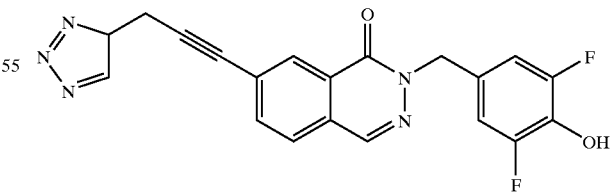

The coupling of 7-bromo-2-(3,5-difluoro-4-hydroxybenzyl)-1H-3-azaisoquinolin-1-one (0.57 g, 1.56 mmol) with 4-prop-2-ynyl-4H-triazole (0.41 g, 3.90 mmol) using triethylamine (0.43 mL, 3.1 1 mmol), CuI (0.021 g, 0.11 mmol), and Pd(Ph$_3$P)$_4$ (0.073 g, 0.06 mmol) in dimethylformamide is carried out as described in Example 1,

EXAMPLE 13A

4-[7-(3-Imidazol-1-ylprop-1-ynyl)-1-oxo-1H-5-azaisoquinolin-2-ylmethyl]benzoic acid tert-butyl ester

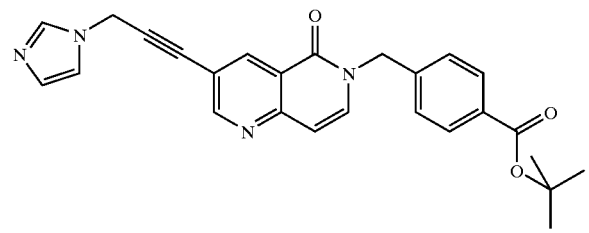

The coupling of 4-(7-bromo-1-oxo-1H-5-azaisoquinolin-2-ylmethyl)benzoic acid tert-butyl ester (0.80 g, 1.93 mmol) with 4-prop-2-ynyl-4H-triazole (0.41 g, 3.86 mmol) using triethylamine (1.08 mL, 7.22 mmol), CuI (0.026 g, 0.14 mmol), and Pd(Ph$_3$P)$_4$ (0.15 g, 0.13 mmol) in dimethyl-formamide is carried out as described in Example 1, Step (2). Purification on a silica gel column eluted with hexane/ethyl acetate 2:1, ethyl acetate, and methylene chloride/THF 4:1, followed by drying, will afford the desired product.

EXAMPLE 13

4-[7-(3-Imidazol-1-ylprop-1-ynyl)-1-oxo-1H-5-azaisoquinolin-2-ylmethyl]benzoic acid

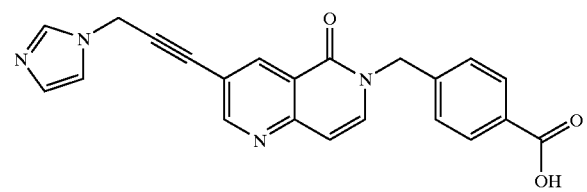

A solution of 4-[7-(3-imidazol-1-ylprop-1-ynyl)-1-oxo-1H-5-azaisoquinolin-2-ylmethyl]benzoic acid tert-butyl ester (0.38 g, 0.86 mmol, Example 13A) is treated with trifluoroacetic acid (6 mL) and stirred at room temperature for 30 minutes. The reaction mixture is evaporated to dryness, triturated with ethyl acetate, the solid is collected by filtration, washed with water, washed with ethyl acetate, and dried under house vacuum. This will afford the desired product.

EXAMPLE 14A

4-[1-Oxo-7-(3-[1,2,3]triazol-1-ylprop-1-ynyl)-1H-6-azaisoquinolin-2-ylmethyl]benzoic acid tert-butyl ester

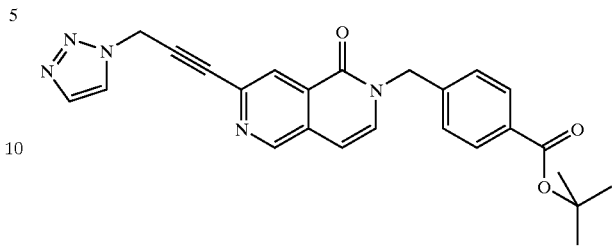

The coupling of 4-(7-bromo-1-oxo-1H-6-azaisoquinolin-2-ylmethyl)benzoic acid tert-butyl ester (0.70 g, 1.69 mmol) with 1-prop-2-ynyl-1H-imidazole (0.45 g, 4.22 mmol) using triethylamine (0.94 mL, 6.76 mmol), CuI (0.023 g, 0.12 mmol), and Pd(Ph$_3$P)$_4$ (0.08 g, 0.07 mmol) in dimethyl-formamide is carried out as described in Example 1, Step (2). The silica gel mesh is purified on a 3.5×18 cm silica gel column eluted with hexanes/ethyl acetate 1:1, methylene chloride/THF 7:1, then methylene chloride/THF 4:1. Evaporation and drying will afford the desired product.

EXAMPLE 14

4-[1-Oxo-7-(3-[1,2,3]triazol-1-ylprop-1-ynyl)-1H-6-azaisoquinolin-2-ylmethyl]benzoic acid

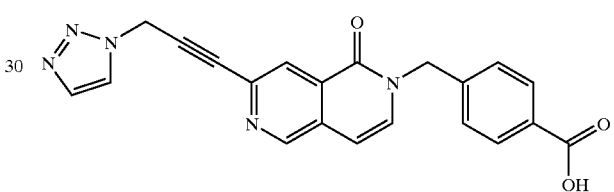

A solution of 4-[1-oxo-7-(3-[1,2,3]triazol-1-ylprop-1-ynyl)-1H-6-azaisoquinolin-2-ylmethyl]benzoic acid tert-butyl ester (0.29 g, 0.66 mmol, Example 14A) is treated with trifluoroacetic acid (10 mL) and stirred at room temperature for 40 minutes. The reaction mixture is evaporated to dryness, triturated with ethyl acetate, the solid collect by filtration, washed with water, washed with ethyl acetate, and dried under house vacuum. This will afford the desired product.

EXAMPLE 15A

4-[1-Oxo-7-(3-[1,2,4]triazol-1-ylprop-1-ynyl)-1H-3,5,8-triazaisoquinolin-2-ylmethyl]benzoic acid tert-butyl ester

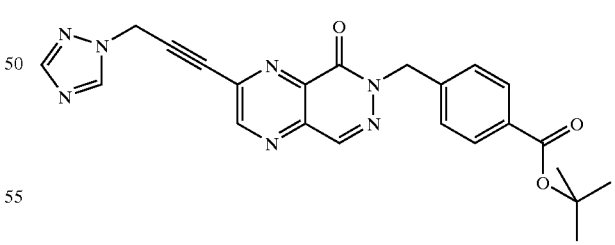

The coupling of 4-(7-bromo-1-oxo-1H-3,5,8-triazaisoquinolin-2-ylmethyl)benzoic acid tert-butyl ester (0.70 g, 1.69 mmol) with 1-prop-2-ynyl-1H-imidazole (0.45 g, 4.22 mmol) using triethylamine (0.94 mL, 6.76 mmol), CuI (0.023 g, 0.12 mmol), and Pd(Ph$_3$P)$_4$ (0.08 g, 0.07 mmol) in dimethyl-formamide is carried out as described in Example 1, Step (2). The silica gel mesh is purified on a 3.5×18 cm silica gel column eluted with hexanes/ethyl acetate 1:1, methylene chloride/THF 7:1, then methylene chloride/THF 4:1. Evaporation and drying will afford the desired product.

EXAMPLE 15

4-[1-Oxo-7-(3-[1,2,4]triazol-1-ylprop-1-ynyl)-1H-3,5,8-triazaisoquinolin-2-ylmethyl]benzoic acid

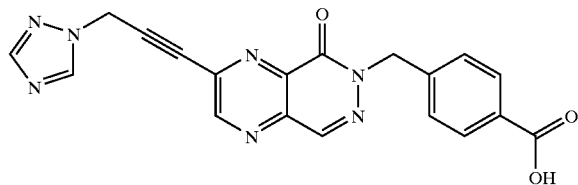

A solution of 4-[1-oxo-7-(3-[1,2,4]triazol-1-ylprop-1-ynyl)-1H-3,5,8-triazaisoquinolin-2-ylmethyl]benzoic acid tert-butyl ester (0.46 g, 1.04 mmol, Example 15A) is treated with trifluoroacetic acid (10 mL) and stirred at room temperature for 40 minutes. The reaction mixture is evaporated to dryness, triturated with ethyl acetate, the solid is collected by filtration, washed with water, washed with ethyl acetate, and dried under house vacuum. This will afford the desired product.

It should be appreciated that when Q is trans-(H)C=C(H), cis-(H)C=C(H), C≡C, CH$_2$C≡C, or CF$_2$C≡C and is bonded to a sp$^2$ carbon atom in Formula I, a palladium catalyzed coupling of the corresponding terminal olefin or alkyne of formulas R$^1$-(trans-(H)C=CH$_2$), R$^1$-(cis-(H)C=CH$_2$), R$^1$—C≡CH, R$^1$—CH$_2$C≡CH, or R$^1$—CF$_2$C≡CH, wherein R$^1$ is as defined above, with a bromo- or iodo-substituted sp$^2$ carbon atom of formula:

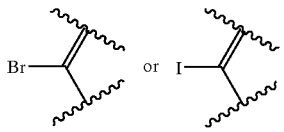

in the presence of a suitable base will yield a compound of Formula I wherein Q is trans-(H)C=C(H), cis-(H)C=C(H), C≡C, CH$_2$C≡C, or CF$_2$C≡C and D is a group that is bonded to Q at a sp$^2$ carbon atom, and R$^1$, V, and R$^2$ are as defined above for Formula I. Illustrative examples of the coupling reagents and catalysts include palladium tetrakis(triphenylphosphine) or palladium(II) acetate as catalyst, a tertiary organic amine base such as triethylamine or diisopropylethylamine, a suitable solvent such as dimethylformamide ("DMF") or tetrahydrofuran ("THF"), and optionally a co-catalyst such as copper(I)iodide, at a suitable temperature such as from 0° C. to 100° C., for a suitable time such as from 30 minutes to 2 days, and under an inert atmosphere such as an atmosphere of nitrogen or argon gas.

Alternatively, a corresponding aldehyde of formula

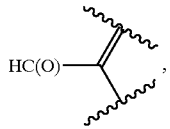

prepared as described below, may be coupled with a phosphonium ylide under Wittig olefination, or Horner-Emmons olefination, conditions to give a compound of Formula I wherein Q is trans-(H)C=C(H).

The bromo or iodo intermediates described above may be converted by conventional means to the corresponding carboxylic acid of formula

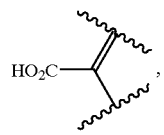

and the carboxylic acid converted by conventional means to compounds of Formula I wherein Q is OC(O), CH(R$^6$)C(O), OC(NR$^6$), CH(R$^6$)C(NR$^6$), N(R$^6$)C(O), N(R$^6$)C(S), N(R$^6$)C(NR$^6$), SC(O), CH(R$^6$)C(S), or SC(NR$^6$). Illustrative examples include coupling of the carboxylic acid with an amine to provide a compound of Formula I wherein Q is N(R$^6$)C(O), and optionally sulfurating the resulting amide with, for example P$_2$S$_5$ to provide a compound of Formula I wherein Q is N(R$^6$)C(S). Alternatively, the carboxylic acid may be coupled with an alcohol to provide a compound of Formula I wherein Q is OC(O).

Alternatively, the carboxylic acid may be reduced to the corresponding hydroxymethyl compound of formula

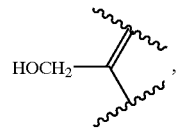

and the hydroxymethyl converted to a compound of Formula I wherein Q is OCH$_2$ or N(R$^6$)CH$_2$ by conventional means.

Alternatively, the hydroxymethyl compound may be oxidized to the corresponding aldehyde of formula

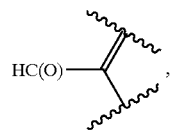

and the aldehyde coupled with hydroxylamine to give a corresponding oxime. The oxime may be chlorinated, and the chlorooxime cyclized with an olefin or alkyne to give a compound of Formula I wherein Q is a 5-membered heteroarylene.

Alternatively, the aldehyde may be prepared from the corresponding carboxylic acid by coupling the carboxylic acid with N,O-dimethylhydroxylamine and reducing the resulting dimethylhydroxamide with a suitable hydride reducing agent such as sodium borohydride or lithium aluminum hydride.

Alternatively, the above-described carboxylic acid intermediate may be converted by conventional means to the corresponding methyl ketone of formula

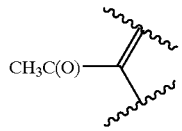

and the methyl ketone may be halogenated on methyl and coupled with various amines, alcohols, or other halogenated compounds to give a compound of Formula I wherein Q is CH(R$^6$)C(O).

Alternatively, the above-described carboxylic acid intermediate or bromo- or iodo-intermediates may be converted by conventional means to the corresponding nitrile of formula

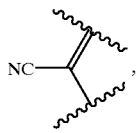

and the nitrile condensed with an amine or alcohol under non-nucleophilic basic conditions (e.g., 1,8-diazaundecane) to give a compound of Formula I wherein Q is $N(R^6)C(NR^6)$ or $OC(NR^6)$, respectively.

Alternatively, compounds of Formula I wherein Q is a lactam diradical may be prepared by conventional means by cyclizing the corresponding gamma-amino acids.

The compounds of Formula I can be evaluated in standard assays for their ability to inhibit the catalytic activity of MMP enzymes. The assays used to evaluate the MMP biological activity of the invention compounds are well-known and routinely used by those skilled in the study of MMP inhibitors and their use to treat clinical conditions. For example, compounds of Formula I may be readily identified by assaying a test compound for inhibition of MMP-13 according to Biological Methods 1 or 2, and further assaying the test compound for allosteric inhibition of MMP-13 according to Biological Methods 3 or 4, as described below.

The compounds of Formula I, as illustrated by the compounds of Examples 1, 2–12, 13A, 13, 14A, 14, 15A, and 15 will be shown to be potent inhibitors of MMP-13 catalytic domain. Potencies, as measured by $IC_{50}$'s, with MMP-13 catalytic domain for the invention compounds will typically range from about 0.001 $\mu$M to about 30 $\mu$M.

Invention compounds can be further screened with full-length MMP-2, full-length MMP-7, full-length MMP-9, and MMP-14 catalytic domain to determine selectivity of the inhibitors with MMP-13 versus the other MMP enzymes also. Selectivities of the invention compounds for MMP-13 catalytic domain versus another MMP enzyme (full-length or catalytic domain), as determined by dividing the $IC_{50}$ for the inhibitor with a comparator MMP enzyme by the $IC_{50}$ of the inhibitor with MMP-13 catalytic domain, are expected to range from 5 to 50,000 fold.

To determine the inhibitory profiles, the compounds of Formula I may be evaluated in standard assays for their ability to inhibit the catalytic activity of various MMP enzymes. The assays used to evaluate the MMP biological activity of the invention compounds are well-known and routinely used by those skilled in the study of MMP inhibitors and their use to treat clinical conditions.

The assays measure the amount by which a test compound reduces the hydrolysis of a thiopeptolide substrate catalyzed by a matrix metalloproteinase enzyme. Such assays are described in detail by Ye et al., in Biochemistry, 1992;31 (45):11231–11235, which is incorporated herein by reference. One such assay is described below in Biological Method 1.

Some of the particular methods described below use the catalytic domain of the MMP-13 enzyme, namely matrix metalloproteinase-13 catalytic domain ("MMP-13CD"), rather than the corresponding full-length enzyme, MMP-13. It has been shown previously by Ye Qi-Zhuang, Hupe D., and Johnson L. (*Current Medicinal Chemistry*, 1996;3:407–418) that inhibitor activity against a catalytic domain of an MMP is predictive of the inhibitor activity against the respective full-length MMP enzyme.

Biological Method 1

Thiopeptolide substrates show virtually no decomposition or hydrolysis at or below neutral pH in the absence of a matrix metalloproteinase enzyme. A typical thiopeptolide substrate commonly utilized for assays is Ac-Pro-Leu-Gly-thioester-Leu-Leu-Gly-OEt. A 100 $\mu$L assay mixture will contain 50 mM of N-2-hydroxyethylpiperazine-N'-2-ethanesulfonic acid buffer ("HEPES," pH 7.0), 10 mM $CaCl_2$, 100 $\mu$M thiopeptolide substrate, and 1 mM 5,5'-dithio-bis-(2-nitro-benzoic acid) (DTNB). The thiopeptolide substrate concentration may be varied, for example from 10 to 800 $\mu$M to obtain $K_m$ and $K_{cat}$ values. The change in absorbance at 405 nm is monitored on a Thermo Max microplate reader (molecular Devices, Menlo Park, Calif.) at room temperature (22° C.). The calculation of the amount of hydrolysis of the thiopeptolide substrate is based on $E_{412}$= 13600 $M^{-1}$ $cm^{-1}$ for the DTNB-derived product 3-carboxy-4-nitrothiophenoxide. Assays are carried out with and without matrix metalloproteinase inhibitor compounds, and the amount of hydrolysis is compared for a determination of inhibitory activity of the test compounds.

Test compounds were evaluated at various concentrations in order to determine their respective $IC_{50}$ values, the micromolar concentration of compound required to cause a 50% inhibition of catalytic activity of the respective enzyme.

It should be appreciated that the assay buffer used with MMP-3CD was 50 mM N-morpholinoethane sulfonate ("MES") at pH 6.0 rather than the HEPES buffer at pH 7.0 described above.

The test described above for the inhibition of MMP-13 may also be adapted and used to determine the ability of the compounds of Formula I to inhibit the matrix metalloproteases MMP-1, MMP-2, MMP-3, MMP-7, MMP-9, MMP-12 and MMP-14.

Biological Method 2

Some representative compounds of Formula I have been evaluated for their ability to inhibit MMP-13. Inhibitor activity versus other MMPs with the compounds may be determined using, for example, MMP-1FL, which refers to full length interstitial collagenase; MMP-2FL, which refers to full length Gelatinase A; MMP-3CD, which refers to the catalytic domain of stromelysin; MMP-7FL, which refers to full length matrilysin; MMP-9FL, which refers to full length Gelatinase B; MMP-13CD, which refers to the catalytic domain of collagenase 3; and MMP-14CD, which refers to the catalytic domain of MMP-14. Test compounds can be evaluated at various concentrations in order to determine their respective $IC_{50}$ values, the micromolar concentration of compound required to cause a 50% inhibition of the hydrolytic activity of the respective enzyme.

The results of the above assays with other MMPs will establish that the compounds of Formula I are potent inhibitors of MMP enzymes, and are especially useful due to their selective inhibition of MMP-13. Because of this potent and selective inhibitory activity, the compounds are especially useful to treat diseases mediated by the MMP enzymes.

Allosteric inhibitors of MMP-13 which are compounds of Formula I may be readily identified by assaying a test compound for inhibition of MMP-13 according to the methods described below in Biological Methods 3 and 4.

Biological Method 3

Fluorigenic Peptide-1 Substrate Based Assay for Identifying compounds of Formula I as Allosteric Inhibitors of MMP-13:
Final assay conditions:
50 mM HEPES buffer (pH 7.0)
10 mM CaCl$_2$
10 μM fluorigenic peptide-1 ("FP1") substrate
0 or 15 mM acetohydroxamic acid (AcNHOH)=1 K$_d$
2% DMSO (with or without inhibitor test compound)
0.5 nM MMP-13CD enzyme
Stock solutions:
1) 10×assay buffer: 500 mM HEPES buffer (pH 7.0) plus 100 mM CaCl$_2$
2) 10 mM FP1 substrate: (Mca)-Pro-Leu-Gly-Leu-(Dnp)-Dpa-Ala-Arg-NH$_2$ (Bachem, M-1895; "A novel coumarin-labeled peptide for sensitive continuous assays of the matrix metalloproteinases," Knight C. G., Willenbrock F., and Murphy, G., FEBS Lett., 1992;296:263–266). Is prepared 10 mM stock by dissolving 5 mg FP1 in 0.457 mL DMSO.
3) 3 M AcNHOH: Is prepared by adding 4 mL H$_2$O and 1 mL 10×assay buffer to 2.25 g AcNHOH (Aldrich 15,903-4). Adjusting pH to 7.0 with NaOH. Diluting volume to 10 mL with H$_2$O. Final solution will contain 3 M AcNHOH, 50 mM HEPES buffer (pH 7.0), and 10 mM CaCl$_2$.
4) AcNHOH dilution buffer: 50 mM HEPES buffer (pH 7.0) plus 10 mM CaCl$_2$
5) MMP-13CD enzyme: Stock concentration=250 nM.
6) Enzyme dilution buffer: 50 mM HEPES buffer (pH 7.0), 10 mM CaCl$_2$, and 0.005% BRIJ 35 detergent (Calbiochem 203728; Protein Grade, 10%)
Procedure (for one 96-well microplate):
A. Prepared assay mixture:
    1100 μL 10×assay buffer
    11 μL 10 mM FP1
    55 μL 3 M AcNHOH or 55 μL AcNHOH dilution buffer
    8500 μL H$_2$O
B. Diluted MMP-13CD to 5 nM working stock:
    22 μL MMP-13CD (250 nM)
    1078 μL enzyme dilution buffer
C. Ran kinetic assay:
1. Dispense 2 μL inhibitor test sample (in 100% DMSO) into well.
2. Add 88 μL assay mixture and mix well, avoiding bubbles.
3. Initiate reactions with 10 μL of 5 nM MMP-13CD; mix well, avoid bubbles.
4. Immediately measure the kinetics of the reactions at room temperature.
    Fluorimeter: F$_{max}$ Fluorescence Microplate Reader & SOFTMAX PRO Version 1.1 software (Molecular Devices Corporation; Sunnyvale, Calif. 94089).

| Protocol menu: | |
| --- | --- |
| excitation: | 320 nm |
| run time: | 15 min |
| RFU min: | −10 |
| V$_{max}$ points: | 32/32 |
| emission: | 405 nm |
| interval: | 29 sec |
| RFU max: | 200 |

D. Compared % of control activity and/or IC$_{50}$ with inhibitor test compound ±AcNHOH.

Hydrolysis of the fluorigenic peptide-1 substrate, [(Mca) Pro-Leu-Gly-Leu-Dpa-Ala-Arg-NH$_2$; Bachem, catalog number M-1895], wherein "Mca" is (7-methoxy-coumarin-4-yl)acetyl and "Dpa" is (3-[2,4-dinitrophenyl]-L-2,3-diaminopropionyl), is used to screen for MMP-13 catalytic domain (CD) inhibitors. (Dpa may also be abbreviated as "Dnp".) Reactions (100 μL) contain 0.05 M Hepes buffer (pH 7), 0.01 M calcium chloride, 0.005% polyoxyethylene (23) lauryl ether ("Brij 35"), 0 or 15 mM acetohydroxamic acid, 10 μM FP1, and 0.1 mM to 0.5 nM inhibitor in DMSO (2% final).

After recombinant human MMP-13CD (0.5 nM final) is added to initiate the reaction, the initial velocity of FP1 hydrolysis is determined by monitoring the increase in fluorescence at 405 nm (upon excitation at 320 nm) continuously for up to 30 minutes on a microplate reader at room temperature. Alternatively, an endpoint read can also be used to determine reaction velocity provided the initial fluorescence of the solution, as recorded before addition of enzyme, is subtracted from the final fluorescence of the reaction mixture. The inhibitor is assayed at different concentration values, such as, for example, 100 μM, 10 μM, 1 μM, 100 nM, 10 nM, and 1 nM. Then the inhibitor concentration is plotted on the X-axis against the percentage of control activity observed for inhibited experiments versus uninhibited experiments (i.e., (velocity with inhibitor) divided by (velocity without inhibitor)×100) on the Y-axis to determine IC$_{50}$ values. This determination is done for experiments done in the presence, and experiments done in the absence, of acetohydroxamic acid. Data are fit to the equation: percent control activity=$100/[1+(([I]/IC_{50})^{slope})]$, where [I] is the inhibitor concentration, IC$_{50}$ is the concentration of inhibitor where the reaction rate is 50% inhibited relative to the control, and slope is the slope of the IC$_{50}$ curve at the curve's inflection point, using nonlinear least-squares curve-fitting equation regression.

Results may be expressed as an IC$_{50}$ Ratio (+/−) ratio, which means a ratio of the IC$_{50}$ of the inhibitor with MMP-13 and an inhibitor to the catalytic zinc of MMP-13, divided by the IC$_{50}$ of the inhibitor with MMP-13 without the inhibitor to the catalytic zinc of MMP-13. Compounds of Formula I which are allosteric inhibitors of MMP-13 are expected to have an IC$_{50}$ Ratio (+/−) ratio of less than 1, and are expected to be synergistic with the inhibitor to the catalytic zinc of MMP-13 such as, for example, AcNHOH. Compounds of Formula I which are not allosteric inhibitors of MMP-13 will be inactive in the assay or will have an IC$_{50}$ Ratio (+/−) of greater than 1, unless otherwise indicated. Results can be confirmed by kinetics experiments which are well known in the biochemical art.

Biological Method 4

Fluorigenic Peptide-1 Based Assay for Identifying Allosteric Inhibitors of Matrix Metalloproteinase-13 Catalytic Domain ("MMP-13CD"):

In a manner similar to Biological Method 3, an assay is run wherein 1,10-phenanthroline is substituted for acetohydroxamic acid to identify compounds of Formula I.

Animal models may be used to establish that the instant compounds of Formula I, or a pharmaceutically acceptable salt thereof, would be useful for preventing, treating, and inhibiting cartilage damage, and thus for treating osteoarthritis, for example. Examples of such animal models are described below in Biological Methods 5 and 6.

Biological Method 5

Monosodium Iodoacetate-induced Osteoarthritis in Rat Model of Cartilage Damage ("MIA Rat"):

One end result of the induction of osteoarthritis in this model, as determined by histologic analysis, is the development of an osteoarthritic condition within the affected joint, as characterized by the loss of Toluidine blue staining and formation of osteophytes. Associated with the histologic changes is a concentration-dependent degradation of joint cartilage, as evidenced by affects on hind-paw weight distribution of the limb containing the affected joint, the presence of increased amounts of proteoglycan or hydroxyproline in the joint upon biochemical analysis, or histopathological analysis of the osteoarthritic lesions.

Generally, In the MIA Rat model on Day 0, the hind-paw weight differential between the right arthritic joint and the left healthy joint of male Wistar rats (150 g) are determined with an incapacitance tester, model 2KG (Linton Instrumentation, Norfolk, United Kingdom). The incapacitance tester has a chamber on top with an outwardly sloping front wall that supports a rat's front limbs, and two weight sensing pads, one for each hind paw, that facilitates this determination. Then the rats are anesthetized with isofluorine, and the right, hind leg knee joint is injected with 1.0 mg of mono-iodoacetate ("MIA") through the infrapatellar ligament. Injection of MIA into the joint results in the inhibition of glycolysis and eventual death of surrounding chondrocytes. The rats are further administered either an invention compound or vehicle (in the instant case, water) daily for 14 days or 28 days. The invention compound is typically administered at a dose of 30 mg per kilogram of rat per day (30 mg/kg/day), but the invention compound may be administered at other doses such as, for example, 10 mg/kg/day, 60 mg/kg/day, 90-mg/kg/day, or 100 mg/kg/day according to the requirements of the compound being studied. It is well within the level of ordinary skill in the pharmaceutical arts to determine a proper dosage of an invention compound in this model. Administration of the invention compound in this model is optionally by oral administration or intravenous administration via an osmotic pump. After 7 and 14 days for a two-week study, or 7, 14, and 28 days for a four-week study, the hind-paw weight distribution is again determined. Typically, the animals administered vehicle alone place greater weight on their unaffected left hind paw than on their right hind paw, while animals administered an invention compound show a more normal (i.e., more like a healthy animal) weight distribution between their hind paws. This change in weight distribution was proportional to the degree of joint cartilage damage. Percent inhibition of a change in hind paw joint function is calculated as the percent change in hind-paw weight distribution for treated animals versus control animals. For example, for a two week study, Percent inhibition of a change in hind paw joint function =

$$\left\{1 - \left[\frac{(\Delta W_G)}{(\Delta W_C)}\right]\right\} \times 100$$

wherein $\Delta W_C$ is the hind-paw weight differential between the healthy left limb and the arthritic limb of the control animal administered vehicle alone, as measured on Day 14; and $\Delta W_G$ is the hind-paw weight differential between the healthy left limb and the arthritic limb of the animal administered an invention compound, as measured on Day 14.

In order to measure biochemical or histopathological end points in the MIA Rat model, some of the animals in the above study may be sacrificed, and the amounts of free proteoglycan in both the osteoarthritic right knee joint and the contralateral left knee joint may be determined by biochemical analysis. The amount of free proteoglycan in the contralateral left knee joint provides a baseline value for the amount of free proteoglycan in a healthy joint. The amount of proteoglycan in the osteoarthritic right knee joint in animals administered an invention compound, and the amount of proteoglycan in the osteoarthritic right knee joint in animals administered vehicle alone, are independently compared to the amount of proteoglycan in the contralateral left knee joint. The amounts of proteoglycan lost in the osteoarthritic right knee joints are expressed as percent loss of proteoglycan compared to the contralateral left knee joint control. The percent inhibition of proteoglycan loss, may be calculated as { [(proteoglycan loss from joint (%) with vehicle)−(proteoglycan loss from joint with an invention compound)]÷(proteoglycan loss from joint (%) with vehicle)}×100.

The MIA Rat data that are expected from the analysis of proteoglycan loss would establish that an invention compound is effective for inhibiting cartilage damage and inflammation and/or alleviating pain in mammalian patients, including human.

The results of these studies with oral dosing may be presented in tabular format in the columns labelled "IJFL (%+/− SEM)", wherein IJFL means Inhibition of Joint Function Limitation, "SDCES", wherein SDCES means Significant Decrease In Cartilage Erosion Severity, and "SIJWHLE", wherein SIJWHLE means Significant Increase in Joints Without Hind Limb Erosion.

The proportion of subjects without hind limb erosions may be analyzed via an *Exact Sequential Cochran-Armitage Trend* test (SAS® Institute, 1999). The Cochran-Armitage Trend test is employed when one wishes to determine whether the proportion of positive or "Yes" responders increases or decreases with increasing levels of treatment. For the particular study, it is expected that the number of animals without joint erosions increased with increasing dose.

The ridit analysis may be used to determine differences in overall erosion severity. This parameter takes into account both the erosion grade (0=no erosion, I=erosion extending into the superficial or middle layers, or II=deep layer erosion), and area (small, medium and large, quantified by dividing the area of the largest erosion in each score into thirds) simultaneously. The analysis recognizes that each unit of severity is different, but does not assume a mathematical relationship between units.

Another animal model for measuring effects of an invention compound on cartilage damage and inflammation and/or pain is described below in Biological Method 6.

Biological Method 6

Induction of Experimental Osteoarthritis in Rabbit ("EOA in Rabbit"):

Normal rabbits are anaesthetized and anteromedial incisions of the right knees performed. The anterior cruciate ligaments are visualized and sectioned. The wounds are closed and the animals are housed in individual cages, exercised, and fed ad libitum. Rabbits are given either vehicle (water) or an invention compound dosed three times per day with 30-mg/kg/dose or 10-mg/kg/dose. The invention compound may be administered at other doses such as, for example, 3 times 20 mg/kg/day or 3 times 60 mg/kg/day according to the requirements of the invention compound being studied. The rabbits are euthanized 8 weeks after surgery and the proximal end of the tibia and the distal end of the femur are removed from each animal.

Macroscopic Grading

The cartilage changes on the femoral condyles and tibial plateaus are graded separately under a dissecting microscope (Stereozoom, Bausch & Lomb, Rochester, N.Y.). The depth of erosion is graded on a scale of 0 to 4 as follows: grade 0=normal surface; Grade 1=minimal fibrillation or a slight yellowish discoloration of the surface; Grade 2=erosion extending into superficial or middle layers only; Grade 3=erosion extending into deep layers; Grade 4=erosion extending to subchondral bone. The surface area changes are measured and expressed in $mm^2$. Representative specimens may also be used for histologic grading (see below).

Histologic Grading

Histologic evaluation is performed on sagittal sections of cartilage from the lesional areas of the femoral condyle and tibial plateau. Serial sections (5 um) are prepared and stained with safranin-O. The severity of OA lesions is graded on a scale of 0–14 by two independent observers using the histologic-histochemical scale of Mankin et al. This scale evaluates the severity of OA lesions based on the loss of safranin-O staining (scale 0–4), cellular changes (scale 0–3), invasion of tidemark by blood vessels (scale 0–1) and structural changes (scale 0–6). On this latter scale, 0 indicates normal cartilage structure and 6 indicates erosion of the cartilage down to the subchondral bone. The scoring system is based on the most severe histologic changes in the multiple sections.

Representative specimens of synovial membrane from the medial and lateral knee compartments are dissected from underlying tissues. The specimens are fixed, embedded, and sectioned (5 um) as above, and stained with hematoxylin-eosin. For each compartment, two synovial membrane specimens are examined for scoring purposes and the highest score from each compartment is retained. The average score is calculated and considered as a unit for the whole knee. The severity of synovitis is graded on a scale of 0 to 10 by two independent observers, adding the scores of 3 histologic criteria: synovial lining cell hyperplasia (scale 0–2); villous hyperplasia (scale 0–3); and degree of cellular infiltration by mononuclear and polymorphonuclear cells (scale 0–5): 0 indicates normal structure.

Statistical Analysis

Mean values and SEM is calculated and statistical analysis was done using the Mann-Whitney U-test.

The results of these studies would be expected to show that an invention compound would reduce the size of the lesion on the tibial plateaus, and perhaps the damage in the tibia or on the femoral condyles. In conclusion, these results would show that an invention compound would have significant inhibition effects on the damage to cartilage.

The foregoing studies would establish that an invention compound is effective for the inhibition of cartilage damage and inflammation and/or alleviating pain, and thus useful for the treatment of osteoarthritis or rheumatoid arthritis in human, and other mammalian disorders. Such a treatment offers a distinct advantage over existing treatments that only modify pain or inflammation or and other secondary symptoms. The effectiveness of an invention compound in this model would indicate that the invention compound will have clinically useful effects in preventing and/or treating cartilage damage, pain and/or inflammation.

Administration according to the invention method of an invention compound to a mammal to treat the diseases listed above is preferably, although not necessarily, accomplished by administering the compound, or a salt thereof, in a pharmaceutical dosage form.

The compounds of Formula I, or a pharmaceutically acceptable salt thereof, can be prepared and administered according to the invention method in a wide variety of oral and parenteral pharmaceutical dosage forms. Thus, the compounds of Formula I, or a pharmaceutically acceptable salt thereof, can be administered by injection, that is, intravenously, intramuscularly, intracutaneously, subcutaneously, intraduodenally, or intraperitoneally. Also, the compounds of Formula I, or a pharmaceutically acceptable salt thereof, can be administered by inhalation, for example, intranasally. Additionally, the compounds of Formula I, or a pharmaceutically acceptable salt thereof, can be administered transdermally. It will be obvious to those skilled in the art that the following dosage forms may comprise as the active component an invention compound. The invention compounds generally are present in a concentration of about 5% to about 95% by weight of the formulation.

For preparing pharmaceutical compositions from the compounds of Formula I, or a pharmaceutically acceptable salt thereof, (i.e., the active component) pharmaceutically acceptable carriers can be either solid or liquid. Solid form preparations are preferred. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component. Powders suitable for intravenous administration or administration by injection may be lyophilized.

In tablets, the active component is mixed with the carrier having the necessary binding properties in suitable proportions and compacted in the shape and size desired.

The powders and tablets preferably contain from about 5% to about 70%, total, of the active component. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active component with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing an appropriate quantity of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.01 to 1000 mg, preferably 1 to 500 mg according to the particular application and the potency of the active components. The composition can, if desired, also contain other compatible therapeutic agents.

In therapeutic use as agents to treat the above-listed diseases, the compounds of Formula I, or a pharmaceutically acceptable salt thereof, are administered at a dose that is effective for treating at least one symptom of the disease or disorder being treated. The initial dosage of about 1 mg/kg to about 100 mg/kg daily of the active component will be effective. A daily dose range of about 25 mg/kg to about 75 mg/kg of the active component is preferred. The dosages, however, may be varied depending upon the requirements of the patient, the severity of the condition being treated, and the particular invention compound being employed in the invention combination. Determination of the proper dosage for a particular situation is within the skill of the art as described above. Typical dosages will be from about 0.1 mg/kg to about 500 mg/kg, and ideally about 25 mg/kg to about 250 mg/kg, such that it will be an amount that is effective to treat the particular disease or disorder being treated.

A preferred composition for dogs comprises an ingestible liquid peroral dosage form selected from the group consisting of a solution, suspension, emulsion, inverse emulsion, elixir, extract, tincture and concentrate, optionally to be added to the drinking water of the dog being treated. Any of these liquid dosage forms, when formulated in accordance with methods well known in the art, can either be administered directly to the dog being treated, or may be added to the drinking water of the dog being treated. The concentrate liquid form, on the other hand, is formulated to be added first to a given amount of water, from which an aliquot amount may be withdrawn for administration directly to the dog or addition to the drinking water of the dog.

A preferred composition provides delayed-, sustained- and/or controlled-release of an invention compound. Such preferred compositions include all such dosage forms which produce $\geq 40\%$ inhibition of cartilage degradation, and result in a plasma concentration of the active component of at least 3 fold the active component's $ED_{40}$ for at least 2 hours; preferably for at least 4 hours; preferably for at least 8 hours; more preferably for at least 12 hours; more preferably still for at least 16 hours; even more preferably still for at least 20 hours; and most preferably for at least 24 hours. Preferably, there is included within the above-described dosage forms those which produce $\geq 40\%$ inhibition of cartilage degradation, and result in a plasma concentration of the active component of at least 5 fold the active component's $ED_{40}$ for at least 2 hours, preferably for at least 2 hours, preferably for at least 8 hours, more preferably for at least 12 hours, still more preferably for at least 20 hours and most preferably for at least 24 hours. More preferably, there is included the above-described dosage forms which produce $\geq 50\%$ inhibition of cartilage degradation, and result in a plasma concentration of the active component of at least 5 fold the active component's $ED_{40}$ for at least 2 hours, preferably for at least 4 hours, preferably for at least 8 hours, more preferably for at least 12 hours, still more preferably for at least 20 hours and most preferably for at least 24 hours.

The following Formulation Examples 1 to 8 illustrate the invention pharmaceutical compositions. When the formulations comprise the invention compound and a pharmaceutically acceptable carrier, diluent, or excipient, they contain a cartilage damage treating effective amount or a therapeutically effective amount such as, for example, an anti-osteoarthritic effective amount of the invention compound. The examples are representative only, and are not to be construed as limiting the invention in any respect.

Tablet Formulation:

| Ingredient | Amount (mg) |
| --- | --- |
| An invention compound | 25 |
| Lactose | 50 |
| Cornstarch (for mix) | 10 |
| Cornstarch (paste) | 10 |
| Magnesium stearate (1%) | 5 |
| Total | 100 |

The invention compound, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for inhibiting cartilage damage or treating osteoarthritis.

Formulation Example 2

Coated Tablets:

The tablets of Formulation Example 1 are coated in a customary manner with a coating of sucrose, potato starch, talc, tragacanth, and colorant.

Formulation Example 3

Injection Vials:

The pH of a solution of 500 g of an invention compound and 5 g of disodium hydrogen phosphate is adjusted to pH 6.5 in 3 L of double-distilled water using 2 M hydrochloric acid. The solution is sterile filtered, and the filtrate is filled into injection vials, lyophilized under sterile conditions, and aseptically sealed. Each injection vial contains 25 mg of the invention compound.

Formulation Example 4

Suppositories:

A mixture of 25 g of an invention compound, 100 g of soya lecithin, and 1400 g of cocoa butter is fused, poured into molds, and allowed to cool. Each suppository contains 25 mg of the invention compound.

Formulation Example 5

Solution:

A solution is prepared from 1 g of an invention compound, 9.38 g of $NaH_2PO_4.12H_2O$, 28.48 g of $Na_2HPO_4.12H_2O$, and 0.1 g benzalkonium chloride in 940 mL of double-distilled water. The pH of the solution is adjusted to pH 6.8 using 2 M hydrochloric acid. The solution is diluted to 1.0 L with double-distilled water, and sterilized by irradiation. A 25 mL volume of the solution contains 25 mg of the invention compound.

Formulation Example 6

Ointment:

500 mg of an invention compound is mixed with 99.5 g of petroleum jelly under aseptic conditions. A 5 g portion of the ointment contains 25 mg of the invention compound.

Formulation Example 7

Capsules:

2 kg of an invention compound are filled into hard gelatin capsules in a customary manner such that each capsule contains 25 mg of the invention compound.

Formulation Example 8

Ampoules:

A solution of 2.5 kg of an invention compound is dissolved in 60 L of double-distilled water. The solution is sterile filtered, and the filtrate is filled into ampoules. The ampoules are lyophilized under sterile conditions and aseptically sealed. Each ampoule contains 25 mg of the invention compound.

The following Formulation Examples 9 to 16 illustrate the invention pharmaceutical compositions containing an invention combination in a single formulation with a pharmaceutically acceptable carrier, diluent, or excipient. The examples are representative only, and are not to be construed as limiting the invention in any respect.

Formulation Example 9

| Tablet Formulation: | |
| --- | --- |
| Ingredient | Amount (mg) |
| An invention compound | 25 |
| A COX-2 inhibitor | 20 |
| Lactose | 50 |
| Cornstarch (for mix) | 10 |
| Cornstarch (paste) | 10 |
| Magnesium stearate (1%) | 5 |
| Total | 120 |

The invention compound or COX-2 inhibitor, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for treatment of one of the above-listed diseases.

Formulation Example 10

Coated Tablets:

The tablets of Formulation Example 9 are coated in a customary manner with a coating of sucrose, potato starch, talc, tragacanth, and colorant.

Formulation Example 11

Injection Vials:

The pH of a solution of 250 g of a COX-2 inhibitor, 500 g of an invention compound, and 5 g of disodium hydrogen phosphate is adjusted to pH 6.5 in 3 L of double-distilled water using 2 M hydrochloric acid. The solution is sterile filtered, and the filtrate is filled into injection vials, lyophilized under sterile conditions, and aseptically sealed. Each injection vial contains 12.5 mg of COX-2 inhibitor and 25 mg of the invention compound.

Formulation Example 12

Suppositories:

A mixture of 50 g of a COX-2 inhibitor, 25 g of an invention compound, 100 g of soya lecithin, and 1400 g of cocoa butter is fused, poured into molds, and allowed to cool. Each suppository contains 50 mg of the COX-2 inhibitor and 25 mg of the invention compound.

Formulation Example 13

Solution:

A solution is prepared from 0.5 g of a COX-2 inhibitor, 1 g of an invention compound, 9.38 g of $NaH_2PO_4.12H_2O$, 28.48 g of $Na_2HPO_4.12H_2O$, and 0.1 g benzalkonium chloride in 940 mL of double-distilled water. The pH of the solution is adjusted to pH 6.8 using 2 M hydrochloric acid. The solution is diluted to 1.0 L with double-distilled water, and sterilized by irradiation. A 25 mL volume of the solution contains 12.5 mg of the COX-2 inhibitor and 25 mg of the invention compound.

Formulation Example 14

Ointment:

100 mg of a COX-2 inhibitor, 500 mg of an invention compound is mixed with 99.4 g of petroleum jelly under aseptic conditions. A 5 g portion of the ointment contains 5 mg of the COX-2 inhibitor and 25 mg of the invention compound.

Formulation Example 15

Capsules:

2 kg of a COX-2 inhibitor and 20 kg of an invention compound are filled into hard gelatin capsules in a customary manner such that each capsule contains 25 mg of the COX-2 inhibitor and 250 mg of the invention compound.

Formulation Example 16

Ampoules:

A solution of 2.5 kg of a COX-2 inhibitor and 2.5 kg of an invention compound is dissolved in 60 L of double-distilled water. The solution is sterile filtered, and the filtrate is filled into ampoules. The ampoules are lyophilized under sterile conditions and aseptically sealed. Each ampoule contains 25 mg each of the COX-2 inhibitor and the invention compound.

While it may be desirable to formulate a COX-2 inhibitor and an invention compound together in one capsule, tablet, ampoule, solution, and the like, for simultaneous administration, it is not necessary for the purposes of practicing the invention methods. A COX-2 inhibitor and an invention compound alternatively can each be formulated independently in any form such as, for example, those of any one Formulation Examples 1 to 16, and administered to a patient either simultaneously or at different times.

The following examples illustrate the invention pharmaceutical compositions containing discrete formulations of the active components of an invention combination and a pharmaceutically acceptable carrier, diluent, or excipient. The examples are representative only, and are not to be construed as limiting the invention in any respect.

Formulation Example 17

Tablet Formulation of an invention compound:

| Ingredient | Amount (mg) |
|---|---|
| An invention compound | 25 |
| Lactose | 50 |
| Cornstarch (for mix) | 10 |
| Cornstarch (paste) | 10 |
| Magnesium stearate (1%) | 5 |
| Total | 100 |

An invention compound, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Injection Vial Formulation of a COX-2 Inhibitor:

The pH of a solution of 500 g of a COX-2 inhibitor and 5 g of disodium hydrogen phosphate is adjusted to pH 6.5 in 3 L of double-distilled water using 2 M hydrochloric acid. The solution is sterile filtered, and the filtrate is filled into injection vials, lyophilized under sterile conditions, and aseptically sealed. Each injection vial contains 25 mg of the COX-2 inhibitor.

Such tablets containing the invention compound can be administered to a human from one to four times a day for treatment of the above-listed diseases, and the injection solutions containing the COX-2 inhibitor can be administered to a human 1 or 2 times per day, wherein the administration by injection is optionally simultaneous with administration of the tablets or at different times, for the treatment of one of the above-listed diseases.

Formulation Example 18

Coated Tablets Containing an Invention Compound:

The tablets of Formulation Example 17 are coated in a customary manner with a coating of sucrose, potato starch, talc, tragacanth, and colorant.
Capsules Containing Valdecoxib or Celecoxib:

2 kg of a COX-2 inhibitor are filled into hard gelatin capsules in a customary manner such that each capsule contains 25 mg of the COX-2 inhibitor.

Such coated tablets containing the invention compound can be administered to a human from one to four times a day for treatment of the above-listed diseases, and the capsules containing the COX-2 inhibitor can be administered to a human 1 or 2 times per day, wherein the administration of the capsules is optionally simultaneous with administration of the tablets or at different times, for the treatment of one of the above-listed diseases.

Still further, it should be appreciated that the invention methods comprising administering an invention combination to a mammal to treat diseases or disorders listed above may be used to treat different diseases simultaneously. For example, administration of a COX-2 inhibitor in accordance with the invention combination may be carried out as described above to treat inflammation, arthritic pain, pain associated with menstrual cramping, and migraines, while an invention compound may be administered to treat OA or inhibit cartilage damage.

As shown above, the invention methods comprising administering an invention compound offer a distinct advantage over existing treatments for diseases such as OA that comprise cartilage damage, wherein the existing treatments modify pain or secondary symptoms, but do not show a disease modifying effect.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

All references cited above are hereby incorporated by reference herein.

Having described the invention method, various embodiments of the invention are hereupon claimed.

What is claimed is:

1. A compound of Formula I

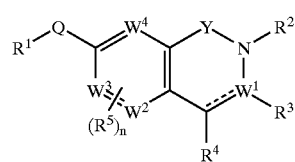

or a pharmaceutically acceptable salt thereof,
wherein:
$R^1$ is independently selected from:
$C_5$ or $C_6$ cycloalkyl-($C_1$-$C_8$ alkylenyl);
Substituted $C_5$ or $C_6$ cycloalkyl-($C_1$-$C_8$ alkylenyl);
$C_8$-$C_{10}$ bicycloalkyl-($C_1$-$C_8$ alkylenyl);
Substituted $C_8$-$C_{10}$ bicycloalkyl-($C_1$-$C_8$ alkylenyl);
5- or 6-membered heterocycloalkyl-($C_1$-$C_8$ alkylenyl);
Substituted 5- or 6-membered heterocycloalkyl-($C_1$-$C_8$ alkylenyl);
8-to 10-membered heterobicycloalkyl-($C_1$-$C_8$ alkylenyl);
Substituted 8- to 10-membered heterobicycloalkyl-($C_1$-$C_8$ alkylenyl);
Phenyl-($C_1$-$C_8$ alkylenyl);
Substituted phenyl-($C_1$-$C_8$ alkylenyl);
Naphthyl-($C_1$-$C_8$ alkylenyl);
Substituted naphthyl-($C_1$-$C_8$ alkylenyl);
5- or 6-membered heteroaryl-($C_1$-$C_8$ alkylenyl);
Substituted 5- or 6-membered heteroaryl-($C_1$-$C_8$ alkylenyl);
8- to 10-membered heterobiaryl-($C_1$-$C_8$ alkylenyl);
Substituted 8- to 10-membered heterobiaryl-($C_1$-$C_8$ alkylenyl);
Phenyl;
Substituted phenyl;
Naphthyl;

Substituted naphthyl;
5- or 6-membered heteroaryl;
Substituted 5- or 6-membered heteroaryl;
8- to 10-membered heterobiaryl; and
Substituted 8- to 10-membered heterobiaryl;
R² is independently selected from:
  H;
  C₁–C₆ alkyl;
  Phenyl-(C₁–C₈ alkylenyl);
  Substituted phenyl-(C₁–C₈ alkylenyl);
  Naphthyl-(C₁–C₈ alkylenyl);
  Substituted naphthyl-(C₁–C₈ alkylenyl);
  5- or 6-membered heteroaryl-(C₁–C₈ alkylenyl);
  Substituted 5- or 6-membered heteroaryl-(C₁–C₈ alkylenyl);
  8- to 10-membered heterobiaryl-(C₁–C₈ alkylenyl);
  Substituted 8- to 10-membered heterobiaryl-(C₁–C₈ alkylenyl);
  Phenyl-O—(C₁–C₈ alkylenyl);
  Substituted phenyl-O—(C₁–C₈ alkylenyl);
  Phenyl-S—(C₁–C₈ alkylenyl);
  Substituted phenyl-S—(C₁–C₈ alkylenyl);
  Phenyl-S(O)-(C₁–C₈ alkylenyl);
  Substituted phenyl-S(O)-(C₁–C₈ alkylenyl);
  Phenyl-S(O)₂—(C₁–C₈ alkylenyl); and
  Substituted phenyl-S(O)₂—(C₁–C₈ alkylenyl);

Each substituted R¹ and R² group contains from 1 to 4 substituents, each independently on a carbon or nitrogen atom, independently selected from:
  C₁–C₆ alkyl;
  CN;
  CF₃;
  HO;
  (C₁–C₆ alkyl)-O;
  (C₁–C₆ alkyl)-S(O)₂;
  H₂N;
  (C₁–C₆ alkyl)-N(H);
  (C₁–C₆ alkyl)₂—N;
  (C₁–C₆ alkyl)-C(O)O—(C₁–C₈ alkylenyl)_m;
  (C₁–C₆ alkyl)-C(O)O-(1- to 8-membered heteroalkylenyl)_m;
  (C₁–C₆ alkyl)-C(O)N(H)—(C₁–C₈ alkylenyl)_m;
  (C₁–C₆ alkyl)-C(O)N(H)-(1- to 8-membered heteroalkylenyl)_m;
  H₂NS(O)₂—(C₁–C₈ alkylenyl);
  (C₁–C₆ alkyl)-N(H)S(O)₂—(C₁–C₈ alkylenyl)_m;
  (C₁–C₆ alkyl)₂—NS(O)₂—(C₁–C₈ alkylenyl)_m;
  3- to 6-membered heterocycoalkyl-(G)_m;
  Substituted 3- to 6-membered heterocycloalkyl-(G)_m;
  5- or 6-membered heteroaryl-(G)_m;
  Substituted 5-or 6-membered heteroaryl-(G)_m;
  (C₁–C₆ alkyl)-S(O)₂N(H)—C(O)—(C₁–C₈ alkylenyl)_m; and
  (C₁–C₆ alkyl)-C(O)—N(H)—S(O)₂—(C₁–C₈ alkylenyl)_m;

wherein each substituent on a carbon atom may further be independently selected from:
  Halo; and
  HO₂C;
wherein 2 substituents may be taken together with a carbon atom to which they are both bonded to form the group C=O;
wherein two adjacent, substantially sp² carbon atoms may be taken together with a diradical substituent to form a cyclic diradical selected from;

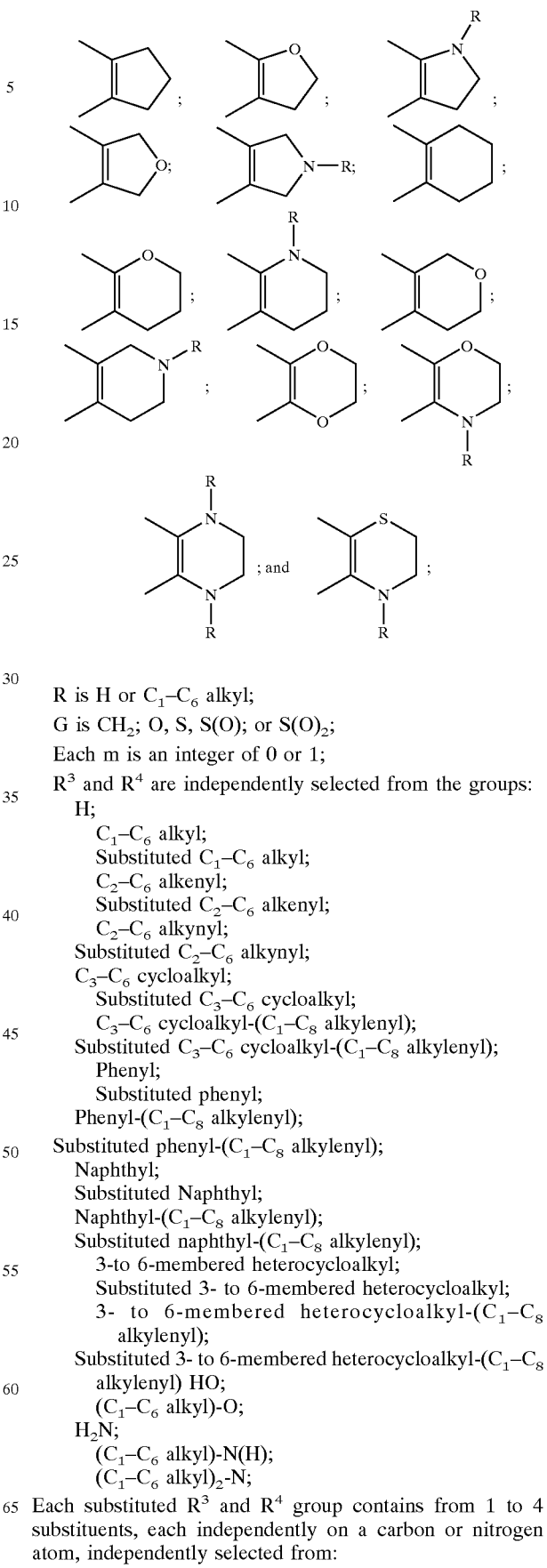

R is H or C₁–C₆ alkyl;
G is CH₂; O, S, S(O); or S(O)₂;
Each m is an integer of 0 or 1;
R³ and R⁴ are independently selected from the groups:
  H;
    C₁–C₆ alkyl;
    Substituted C₁–C₆ alkyl;
    C₂–C₆ alkenyl;
    Substituted C₂–C₆ alkenyl;
    C₂–C₆ alkynyl;
    Substituted C₂–C₆ alkynyl;
    C₃–C₆ cycloalkyl;
    Substituted C₃–C₆ cycloalkyl;
    C₃–C₆ cycloalkyl-(C₁–C₈ alkylenyl);
    Substituted C₃–C₆ cycloalkyl-(C₁–C₈ alkylenyl);
    Phenyl;
    Substituted phenyl;
    Phenyl-(C₁–C₈ alkylenyl);
  Substituted phenyl-(C₁–C₈ alkylenyl);
  Naphthyl;
  Substituted Naphthyl;
  Naphthyl-(C₁–C₈ alkylenyl);
  Substituted naphthyl-(C₁–C₈ alkylenyl);
    3-to 6-membered heterocycloalkyl;
    Substituted 3- to 6-membered heterocycloalkyl;
    3- to 6-membered heterocycloalkyl-(C₁–C₈ alkylenyl);
    Substituted 3- to 6-membered heterocycloalkyl-(C₁–C₈ alkylenyl) HO;
    (C₁–C₆ alkyl)-O;
  H₂N;
    (C₁–C₆ alkyl)-N(H);
    (C₁–C₆ alkyl)₂-N;
Each substituted R³ and R⁴ group contains from 1 to 4 substituents, each independently on a carbon or nitrogen atom, independently selected from:

H₂N;
C₁–C₆ alkyl;
CN;
CF₃;
(C₁–C₆ alkyl)-OC(O);
HO;
(C₁–C₆ alkyl)-O;
HS; and
(C₁–C₆ alkyl)-S;
  wherein each substituent on a carbon atom may further be independently selected from:
  Halo; and
  HO₂C;
wherein 2 substituents may be taken together with a carbon atom to which they are both bonded to form the group C=O;
R⁵ is H, C₁–C₆ alkyl, H₂N, HO, or halo;
n is an integer of from 0to 3;
Q is selected from:
  C≡C;
  CH₂C≡C;
  C≡CCH₂;
  CF₂C≡C; and
  C≡CCF₂;
R⁶ is H, C₁–C₆ alkyl, C₃–C₆ cycloalkyl; 3- to 6-membered heterocycloalkyl;
  phenyl; benzyl; or 5- or 6-membered heteroaryl;
Y is C(=O), CH₂; or C(H)(R⁷);
Each R⁷ is independently C₁–C₆ alkyl, H₂N; HO; or halo;
—means a bond which is optionally present or absent;
W¹ is independently C(H)R⁵ when—is absent, wherein R⁵ is as defined above;
W¹ is independently C—R⁵ when—is a bond, wherein R⁵ is as defined above;
Each W², W³, and W⁴ is independently N or C-R⁵, wherein R⁵ is as defined above;
wherein 1 of W², W³, and W⁴ is N and the other two of W², W³, and W⁴ is C—R⁵;
wherein each C₈–C₁₀ bicycloalkyl is a bicyclic carbocyclic ring that contains 8-, 9- or 10-member carbon atoms which are 5,5-fused, 6,5-fused, or 6,6-fused bicyclic rings, respectively, and wherein the ring is saturated or optionally contains one carbon-carbon double bond;
wherein each 8- to 10-membered heterobicycloalkyl is a bicyclic ring that contains carbon atoms and from 1 to 4 hetaroatoms independently selected from 2O, 1 S, 1 S(O), 1 S(O)₂, 1 N, 4 N(H), and 4 N(C₁–C₆ alkyl), and wherein when two O atoms or one O atom and one S atom are present, the two O atoms or one O atom and one S atom are not bonded to each other, and wherein the ring is saturated or optionally contains one carbon-carbon or carbon-nitrogen double bond, and wherein the heterobicycloalkyl is a 5,5-fused, 6,5-fused, or 6,6-fused bicyclic ring, respectively,
wherein each heterocycloalkyl is a ring that contains carbon atoms and from 1 to 4 heteroatoms independently selected from 2O, 1 S, 1 S(O), 1 S(O)₂, 1 N, 4 N(H), and 4 N(C₁–C₆ alkyl), and wherein when two O atoms or one O atom and one S atom are present, the two O atoms or one O atom and one S atom are not bonded to each other, and wherein the ring is saturated or optionally contains one carbon-carbon or carbon-nitrogen double bond;

wherein each 5-membered heteroaryl contains carbon atoms and from 1 to 4 heteroatoms independently selected from 1 O, 1 S, 1 N(H), 1 N(C₁–C₆ alkyl), and 4 N, and each 6-membered heteroaryl contains carbon atoms and 1 or 2 heteroatoms independently selected from N, N(H), and N(C₁–C₆ alkyl), and 5- and 6-membered heteroaryl are monocyclic rings;

wherein each heterobiaryl contains carbon atoms and from 1 to 4 heteroatoms independently selected from 1 O, 1 S, 1 N(H), 1 N(C₁–C₆ alkyl), and 4 N, and where the 8-, 9-, and 10-membered heterobiaryl are 5,5-fused, 6,5-fused, and 6,6-fused bicyclic rings, respectively, and wherein at least 1 of the 2 fused rings of a bicyclic ring is aromatic, and wherein when the O and S atoms both are present, the O and S atoms are not bonded to each other;

wherein with any (C₁–C₆ alkyl)₂-N group, the C₁–C₆ alkyl groups may be optionally taken together with the nitrogen atom to which they are attached to form a 5- or 6-membered heterocycloalkyl;

wherein each group and each substituent recited above is independently selected.

2. The compound according to claim 1, or a pharmaceutically acceptable salt thereof, wherein Y is C(=O) or CH₂.

3. The compound according to claim 1, or a pharmaceutically acceptable salt thereof, wherein Q is N(R⁶)C(O).

4. The compound according to claim 1, or a pharmaceutically acceptable salt thereof, wherein Q is C≡C, CH₂C≡C, C≡CCH₂, CF₂C≡C, or C≡CCF₂.

5. The compound according to claim 1, wherein W³ or W⁴ is N and Q is N(H)C(O).

6. The compound according to any one of claims 1, 2, or 3 to 5, inclusive wherein R¹ and R² are independently selected from:
  5- or 6-membered heteroaryl-(C₁–C₈ alkylenyl);
  Substituted 5- or 6-membered heteroaryl-(C₁–C₈ alkylenyl);
  8- to 10-membered heterobiaryl-(C₁–C₈ alkylenyl);
  Substituted 8- to 10-membered heterobiaryl-(C₁–C₈ alkylenyl);
  Phenyl-(C₁–C₈ alkylenyl); and
  Substituted phenyl-(C₁–C₈ alkylenyl).

7. The compound according to claim 1, selected from:
4-[1-Oxo-7-(3-phenyl-prop-1-ynyl)-1H-3-azaisoquinolin-2-ylmethyl]benzoic acid tert-butyl ester;
4-[1-Oxo-7-(3-phenyl-prop-1-ynyl)-1H-3-azaisoquinolin-2-ylmethyl]benzoic acid;
2-(3,5-Difluoro-4-hydroxybenzyl)-7-[3-(4H-[1,2,3]triazol-4-yl)prop-1-ynyl]-2H-3-azaisoquinolin-1-one;
7-(3-phenyl-prop-1-ynyl)-2-(4-trifluoromethylbenzyl)-2H-5-azaisoquinolin-1-one;
2-(3-Fluorobenzyl)-7-(3-phenyl-prop-1-ynyl)-2H-5-azaisoquinolin-1-one;
4-[7-(3-Imidazol-1-ylprop-1-ynyl)-1-oxo-1H-5-azaisoquinolin-2-ylmethyl]benzoic acid tert-butyl ester;
4-[7-(3-Imidazol-1-ylprop-1-ynyl)-1-oxo-1H-5-azaisoquinolin-2-ylmethyl]benzoic acid;
3-[1-Oxo-7-(3-phenyl-prop-1-ynyl)-1H-6-azaisoquinolin-2-ylmethyl]benzonitrile;
4-[1-Oxo-7-(3-phenyl-prop-1-ynyl)-1H-6-azaisoquinolin-2-ylmethyl]benzenesulfonamide;
4-[1-Oxo-7-(3-[1,2,3]triazol-1-ylprop-1-ynyl)-1H-6-azaisoquinolin-2-ylmethyl]benzoic acid tert-butyl ester;
4-[1-Oxo-7-(3-[1,2,3]triazol-1-ylprop-1-ynyl)-1H-6-azaisoquinolin-2-ylmethyl]benzoic acid;
4-[1-Oxo-7-(3-phenyl-prop-1-ynyl)-1H-8-azaisoquinolin-2-ylmethyl]benzoic acid methyl ester; and 3-[1-Oxo-7-(3-phenyl-prop-1-ynyl)-1H-8-azaisoquinolin-2-ylmethyl]benzoic acid methyl ester;
a pharmaceutically acceptable salt thereof.

8. A pharmaceutical composition, comprising a compound according to claim 1, or a pharmaceutically acceptable salt thereof, admixed with a pharmaceutically acceptable carrier, excipient, or diluent.

9. The pharmaceutical composition according to claim 8, comprising a compound selected from:
4-[1-Oxo-7-(3-phenyl-prop-1-ynyl)-1H-3-azaisoquinolin-2-ylmethyl]benzoic acid tert-butyl ester;
4-[1-Oxo-7-(3-phenyl-prop-1-ynyl)-1H-3-azaisoquinolin-2-ylmethy]benzoic acid;
2-(3,5-Difluoro-4-hydroxybenzyl)-7-[3-(4H-[1,2,3]triazol-4-yl)prop-1-ynyl]-2H-3azaisoquinolin-1-one;
7-(3-phenyl-prop-1-ynyl)-2-(4-trifluoromethylbenzyl)-2H-5-azaisoquinulin-1-one;
2-(3-Fluorobenzyl)-7-(3-phenyl-prop-1-ynyl)-2 H-5-azaisoquinolin-1-one;
4-[7-(3-Imidazol-1-ylprop-1-ynyl)-1-oxo-1H-5-azaisoquinolin-2-ylmethyl]benzoic acid tert-butyl ester;
4-[7-(3-Imidazol-1-ylprop-1-ynyl)-1 oxo-1H-5-azaisoquinolin-2-ylmethyl]benzoic acid;
3-[1-Oxo-7-(3-phenyl-prop-1-ynyl)-1H-6-azaisoquinolin-2-ylmethyl]benzonitrile;
4-[1-Oxo-7-(3-phenyl-prop-1-ynyl)-1H-6-azaisoquinolin-2-ylmethyl]benzenesulfonamide;
4-[1-Oxo-7-(3-[1,2,3]triazol-1-ylprop-1ynyl)-1H-6-azaisoquinolin-2-ylmethyl]benzoic acid tert-butyl ester;
4-[1-Oxo-7-(3-[1,2,3]triazol-1-ylprop-1-ynyl)-1H-6-azaisoquinolin-2-ylmethyl]benzoic acid;
4-[1-Oxo-7-(3-phenyl-prop-1-ynyl)-1H-8-azaisquinolin-2-ylmethyl]benzoic acid methyl ester; and
3-[1-Oxo-7-(3-phenyl-prop-1-ynyl)-1H-8-azaisoquinolin-2-ylmethyl]benzoic acid methyl ester;
or a pharmaceutically acceptable salt thereof, admixed with a pharmaceutically acceptable carrier, excipient, or diluent.

10. A method for treating osteoarthritis or rheumatoid arthritis, comprising administering to a patient suffering from osteoarthritis a nontoxic effective amount of a compound according to claim 1, or a pharmaceutically acceptable salt thereof.

11. The method according to claim 10, wherein the compound administered is a compound selected from:
4-[1-Oxo-7-(3-phenyl-prop-1-ynyl)-1H-3-azaisoquinolin-2ylmethy]benzoic acid tert-butyl ester;
4-[1-Oxo-7-(3-phenyl-prop-1-ynyl)-1H-3-azaisoquinolin-2ylmethy]benzoic acid;
2-(3,5-Difluoro-4-hydroxybenzyl)-7-[3-(4H-[1,2,3]triazol-4-yl)prop-1-ynyl]-2H-3-azaisoquinolin-1-one;
7-(3-phenyl-prop-1-ynyl)-2-(4-trifluoromethylbenzyl)-2H-5-azaisoquinulin-1-one;
2-(3-Fluorobenzyl)-7-(3-phenyl-prop-1-ynyl)-2 H-5-azaisoquinolin-1-one;
4-[7-(3-Imidazol-1-ylprop-1-ynyl)1 -oxo-1H-5-azaisoquinolin-2-ylmethyl]benzoic acid tert-butyl ester;
4-[7-(3-Imidazol-1-ylprop-1-ynyl)1 -oxo-1H-5-azaisoquinolin-2-ylmethyl]benzoic acid;
3-[1-Oxo-7-(3-phenyl-prop-1-ynyl)-1H-6-azaisoquinolin-2-ylmethyl]benzonitrile;
4-[1-Oxo-7-(3-phenyl-prop-1-ynyl)-1H-6-azaisoquinolin-2-ylmethyl]benzenesulfonamide;
4-[1-Oxo-7-(3-[1,2,3]triazol-1-ylprop-1-ynyl)-1H-6-azaisoquinolin-2-ylmethyl]benzoic acid tert-butyl ester;
4-[1-Oxo-7-(3-[1,2,3]triazol-1-ylprop-1-ynyl)-1H-6-azaisoquinolin-2-ylmethyl]benzoic acid;
4-[1-Oxo-7-(3-phenyl-prop-1-ynyl)-1H-8-azaisquinolin-2-ylmethyl]benzoic acid methyl ester; and
3-[1-Oxo-7-(3-phenyl-prop-1-ynyl)-1H-8-azaisoquinolin-2-ylmethyl]benzoic acid methyl ester; or
a pharmaceutically acceptable salt thereof.

* * * * *